US007018627B1

(12) United States Patent
Gray et al.

(10) Patent No.: US 7,018,627 B1
(45) Date of Patent: Mar. 28, 2006

(54) MACROPHAGE DERIVED CHEMOKINE (MDC), MDC ANALOGS, MDC INHIBITOR SUBSTANCES, AND USES THEREOF

(75) Inventors: Patrick W. Gray, Seattle, WA (US); David H. Chantry, Seattle, WA (US); Michael C. Deeley, Edmonds, WA (US); Carol J. Raport, Bothell, WA (US); Ronald Godiska, Verona, WI (US)

(73) Assignee: Icos Corporation, Bothell, WA (US)

( * ) Notice: Subject to any disclaimer, the term of this patent is extended or adjusted under 35 U.S.C. 154(b) by 0 days.

(21) Appl. No.: 09/509,165

(22) PCT Filed: Sep. 28, 1998

(86) PCT No.: PCT/US98/20270

§ 371 (c)(1),
(2), (4) Date: Jun. 12, 2000

(87) PCT Pub. No.: WO99/15666

PCT Pub. Date: Apr. 1, 1999

Related U.S. Application Data

(63) Continuation-in-part of application No. 09/067,447, filed on Apr. 28, 1998, now Pat. No. 6,737,513, and a continuation-in-part of application No. 08/939,107, filed on Sep. 26, 1997, now Pat. No. 6,498,015, and a continuation-in-part of application No. 08/660,542, filed on Jun. 7, 1996, now Pat. No. 5,932,703, and a continuation-in-part of application No. 08/558,658, filed on Nov. 16, 1995, now abandoned, and a continuation-in-part of application No. 08/479,620, filed on Jun. 7, 1995, now Pat. No. 6,790,947.

(51) Int. Cl.
G01N 33/55 (2006.01)
C07K 16/22 (2006.01)
C07K 16/24 (2006.01)
C07K 16/26 (2006.01)
C07K 17/00 (2006.01)

(52) U.S. Cl. ............... 424/93.1; 424/2; 424/134.1; 424/138.1; 424/141.1; 424/142.1; 424/152.1; 424/153.1; 530/387.1; 530/388.23; 530/388.1; 530/388.24; 530/388.25; 435/7.1; 435/7.2

(58) Field of Classification Search ............... 435/2, 435/3, 7.1, 7.03, 7.21, 325, 336, 343.1; 424/9.1, 424/85.1, 131.1, 141.1, 134.1, 135.1, 143.1, 424/93.1; 530/350
See application file for complete search history.

(56) References Cited

U.S. PATENT DOCUMENTS

| 4,965,392 A | 10/1990 | Fritzberg et al. ............ 558/254 |
| 5,013,739 A | 5/1991 | Bihari et al. ................ 514/282 |
| 5,037,630 A | 8/1991 | Fritzberg et al. ............ 424/1.1 |
| 5,179,078 A | 1/1993 | Rollins et al. ................ 514/2 |
| 5,241,049 A | 8/1993 | Goodman et al. ........... 530/350 |
| 5,278,287 A | 1/1994 | Rollins et al. ............. 530/351 |
| 5,413,778 A | 5/1995 | Kunkel et al. ............. 424/1.41 |
| 5,459,128 A | 10/1995 | Rollins et al. ................ 514/8 |
| 5,688,927 A | 11/1997 | Godiska et al. ......... 530/388.23 |
| 5,705,360 A | 1/1998 | Rollins et al. ............. 435/69.1 |
| 5,932,703 A | 8/1999 | Godiska et al. ............. 530/351 |
| 6,245,332 B1 | 6/2001 | Butcher et al. ........... 424/484.1 |
| 6,265,184 B1 | 7/2001 | Gray et al. ................ 435/69.1 |
| 6,268,477 B1 | 7/2001 | Gray et al. ................ 530/350 |
| 6,320,023 B1 | 11/2001 | Godiska et al. ............. 530/324 |
| 6,498,015 B1 | 12/2002 | Godiska et al. |
| 2002/0055147 A1 | 5/2002 | Li et al. |
| 2002/0098545 A1 | 7/2002 | Li et al. |

FOREIGN PATENT DOCUMENTS

| EP | 0 153 678 | 9/1985 |
| EP | 0 310 136 A | 4/1989 |
| EP | 0 317 053 | 5/1989 |
| EP | 0 462 960 | 12/1991 |
| EP | 0 647 447 | 4/1995 |
| EP | 0 666 257 | 8/1995 |
| EP | 0 725 059 | 8/1996 |
| EP | 0 860 446 | 8/1998 |
| WO | WO 89/01046 | 2/1989 |
| WO | WO 91/09955 | 7/1991 |
| WO | WO 92/20808 | 11/1992 |
| WO | WO 94/12650 | 6/1994 |
| WO | WO 95/17092 | 6/1995 |
| WO | WO 96/39521 | 12/1996 |
| WO | WO 96/40923 | 12/1996 |
| WO | WO 97/11969 | 4/1997 |
| WO | WO 96/23068 | 8/1997 |

(Continued)

OTHER PUBLICATIONS

Schaniel et al. J. Exp. Med. 1998, vol. 188, pp. 451-463.*

(Continued)

Primary Examiner—James Housel
Assistant Examiner—Bao Qun Li
(74) Attorney, Agent, or Firm—Marshall, Gerstein & Borun LLP

(57) ABSTRACT

The present invention provides purified and isolated polynucleotide sequences encoding a novel macrophage-derived C—C chemokine designated "Macrophage Derived Chemokine" (MDC), and polypeptide fragments and analogs thereof. Also provided are materials and methods for the recombinant or synthetic production of the chemokine, fragments, and analogs; and purified and isolated chemokine protein, and polypeptide fragments and analogs thereof. Also provided are antibodies reactive with the chemokine and methods of making and using all of the foregoing. Also provided are assays for identifying modulators of MDC chemokine activity.

8 Claims, 12 Drawing Sheets

FOREIGN PATENT DOCUMENTS

| WO | WO 97/29192 | 8/1997 |
| --- | --- | --- |
| WO | WO 97/44055 | 11/1997 |
| WO | WO 97/44462 | 11/1997 |
| WO | WO 98/11226 | 3/1998 |
| WO | WO 95/13295 | 5/1998 |
| WO | WO 98/24907 | 6/1998 |
| WO | WO 98/24908 | 6/1998 |
| WO | WO 01/32128 A3 | 5/2001 |

OTHER PUBLICATIONS

Vicari et al. Immunity 1997, vol. 7, pp. 291-301.*
Bochner et al. J. Allergy Clinical Immunology 1999, vol. 103, pp. 527-532.*
Conrey et al. J Leukoc Biol. 2003, vol. 74, No. 4, pp. 558-563.*
Aalbers et al., "Dynamics of Eosinophil Infiltration in the Bronchial Mucosa Before and After the Late Asthmatic Reaction," *Eur. Respir. J.*, 6:840 (1993).
Abi-Younes, S. et al., "The CC Chemokines MDC and TARC Induce Platelet Activation Via CCR4," *Thromb. Res.* 101 (4): 278-89 (2001).
Adema, G.J. et al., "A Dendritic-cell-derived C-C Chemokine That Preferentially Attracts Naive T Cells," *Nature*, 387 :713-717 (Jun. 12, 1997).
Adams, D.O., "The Granulomatous Inflammatory Response, " *Am. J. Pathol.*, 84 (1):164-191 (Jul., 1976).
Ahuja et al., "Molecular Evolution of the Human Interleukin-8 Receptor Gene Cluster," *Nature Genetics*, 2: 31-36 (Sep., 1992).
Amakawa, R. et al., "Impaired Negative Selection of T cells in Hodgekins Disease Antigen CD30-Deficient Mice," *Cell* 84: 551-62 (1996).
Aujame, L. et al., "High Affinity Human Antibodies By Phage Display," *Human Antibodies*, 8(4):155-168 (1997).
Austrup, F., et al., "P-and E-selectin Mediate Recruitment of T-helper-1 But Not T-helper-2 Cells Into Inflamed Tissues," *Nature 385*, 81-83 (1997).
Baba, M. et al., "Identification of CCR6, the Specific Receptor for a Novel Lymphocyte-directed CC Chemokine LARC, " *J. Biological Chemistry*, 272(23):14893-14898 (Jun. 6, 1997).
Bagglioni et al., "CC Chemokines in Allergic Inflammation," *Immunol. Today 15*: 127 (1994).
Baggiolini et al., "Interleukin-8 and Related Chemotactic Cytokines-CXC and CC Chemokines," *Advances in Immunology*, 55:97-179 (1994).
Baggiolini, M. et al., "Human Chemokines: An Update," *Annu. Rev. Immunol.*, 15:675-705 (1997).
Baggiolini, M., et al., "Chemokines and Leukocyte Traffic," Nature (London), 392:565-68 (1998).
Bai et al., "IL-10 Suppresses Experimental Autoimmune Neuritis and Down-regulates $T_H1$-Type Immune Responses, " *Clin. Immunol. Immunopathol.*, 83(2):117-126 (1997).
Barker et al., "Effects of $T_H1$ and $T_H2$ cytokines on $CD8^+$cell response against human immunodeficiency virus: Implications for long-term survival," *Proc. Natl. Acad. Sci., USA*, 92(24 ):11135-11139 (1995).
Baumer et al., "Th1/Th2 Cell Distribution in Pulmonary Sarcoidosis," *Am. J. Respir. Cell Mol. Biol.*, 16(2):171-177 (1997).
Beck, L. A., et al., "Cutaneous Injection of RANTES Causes Eosinophil Recruitment: Comparison of Nonallergic and Allergic Human Subjects," *J. Immunol. 159*:2962.

Becker et al., "Constitutive and Stimulated MCP-1, GROα, β, and γ Expression in Human Airway Epithelium and Bronchoalveolar Macrophages," *Am. J. Physiol.*, 266:L278-L288 (1994).
Ben-Baruch, A. et al., "Monocyte Chemotactic Protein-3 (MCP3) Interacts with Multiple Leukocyte Receptors," *J. Biological Chemistry*, 270(38):22123-22128 (Sep. 22, 1995).
Berger et al., "Distinct Antigen-induced Cytokine Pattern Upon Stimulation With Antibody-complexed Antigen Consistent With a Th1→Th2-shift," *Res. Virol.*, 147(2-3): 103-108 (1996).
Berin, M.C. et al., "Production of MDC/CCL22 by Human Intestinal Epithelial Cells," Am. J. Physiol. Gastrointest. Liver Physiol. 280: G1217-G1226 (2001).
Bertoletti et al., "Different Cytokine Profiles of Intrahepatic T Cells in Chronic Hepatitis B and Hepatitis C Virus Infections," *Gastroenterol.*, 112(1):193-199 (1997).
Bleul, C.C et al., "The Lymphocyte Chemoattractant SDF-1 Is a Ligand for LESTR/fusin and Blocks HIV-1 Entry," *Nature*, 382:829-833 (Aug. 29, 1996).
Bochner, B. S., et al., "Adhesion of Human Basophils, Eosinophils and Neutrophils to IT-1-Activated Human Vascular Endothelial Cells: Contributions of Endothelial Cell Adhesion Molecules," J. Exp. Med. 173: 1553 (1991).
Bombardier et al., "Derivation of the SLEDAI: a Disease Activity Index for Lupus Patients," *Arthritis Rheum*, 35: 630-40 (1992).
Bonecchi, R. et al., "Differential Expression of Chemokine Receptors and Chemotactic Responsiveness of Type 1 T Helper Cells (Th1s) and Th2s," *J. Exp. Med.*, 187(1):129-134 (Jan. 5, 1998).
Bowie et al., "Deciphering the Message in Protein Sequences: Tolerance to Amino Acid Substitutions," *Science, 247*:1306-1310 (1990).
Brown et al., "A Family of Small Inducible Proteins Secreted by Leukocytes are Members of a New Superfamily that Includes Leukocyte and Fibroblast-Derived Inflammatory Agents, Growth Factors, and Indicators of Various Activation Processes," *J. Immunol.*, 142(2):679-687 (Jan. 15, 1989).
Brown, A.F., "Anaphylactic Shock: Mechanisms and Treatment," *J. Accid. Emerg. Med.*, 12(2):89-100 (1995).
Brüggemann, M. and Neuberger, "Strategies for expressing human antibody repertoires in transgenic mice," *Immunol. Today*, 17(8):391-397 (1996).
Brüggemann, M. and Taussig, "Production of human antibody repertoires in transgenic mice," *Current Opinion Biotechnology*, 8:455-458 (1997).
Carballido, J.M. et al., "The Intensity of T Cell Receptor Engagement Determines the Cytokine Pattern of Human Allergen-specific T Helper Cells," *Eur. J. Immunol.*, 27(2): 515-521 (1997).
Cenci et al., "T Helper Cell Type 1 (Th1)-and Th2-like Responses Are Present in Mice with Gastric Candidiasis but Protective Immunity Is Associated with Th1 Development," *J. Infect. Dis.*, 171(5):1279-1288 (1995).
Chang et al., "Cloning and expression of a γ-interferon-inducible gene in monocytes: a new member of a cytokine gene family," *International Immunology*, 1(4):388-397 (1989).

Chang, M-S et al., "Molecular Cloning and Functional Characterization of a Novel CC Chemokine, Stimulated T Cell Chemotactic Protein (STCP-1) That Specifically Acts on Activated T Lymphocytes," *J. Biological Chemistry*, 272(40):25229-25237 (Oct. 1, 1997).

Chantry, D., et al., "Profile of Human Macrophage Transcripts: Insights into Macrophage Biology and Identification of Novel Chemokines," *J. Leuk. Biol.*, 64(1): 49-54 (1998).

Chantry, D. et al., Macrophage-derived Chemokine is Localized to Thymic Medullary Epithelial Cells and is a Chemoattractant for CD3(+), CD4(+), CD8(low) Thymocytes, *Blood*, 94(6): 1890-98 (1999).

Charo et al., "Molecular Cloning and Functional Expression of Two Monocyte Chemmoattractant Protein 1 Receptors Reveals Alternative Splicing of the Carboxyl-terminal Tails, " *Proc. Nat'l. Acad. Sci., USA*, 91:2752-2756 (Mar., 1994).

Chemokines, In R&D Systems 1995 catalog, R&D Systems, Minneapolis, MN, pp. 79-85.

Cheung et al., "Modulation of Lymphocyte Motility by Macrophages," *Cell. Immunol.*, 109(2):295-305 (1987).

Clapham, P.R., "HIV and Chemokines: Ligands Sharing Cell Surface Receptors," *Trends in Cell Biol.* 7, 264-268 (1997).

Clark-Lewis et al., "Structure-Activity Relationships of Interleukin-8 Determined Using Chemically Synthesized Analogs," *J. Biol. Chem.*, 266(34):23128-23134 (Dec. 5, 1991).

Co, M.S. et al, "Humanized antibodies for therapy," *Nature*, 351:501-502 (Jun. 6, 1991).

Cocchi et al., "Identification of RANTES, MIP-1α, and MIP-1β as the Major HIV-Suppressive Factors Produced by $CD8^+T$ Cells," *Science*, 270:1811-1815 (Dec. 15, 1995).

Combadiere et al., "Cloning and Functional Expression of a Human Eosinophil CC Chemokine Receptor," *J. Biol. Chem.*,270(27):16491-16494 (Jul. 14, 1995).

Corrigan et al., "T-cell/eosinophil Interactions in the Induction of Asthma," *Eur. Respir. J. Suppl.* 22, 72s-78s (1996).

Cota, M. et al., "Selective Inhibition of HIV Replication in Primary Macrophages but not T Lymphocytes by Macrophage-derived Chemokine," *PNAS*, 97(16): 9162-67.(2000).

Daikh et al., J. Immunol., "Long-term Inhibition of Murine Lupus By Brief Simultaneous Blockade of the B7/CD28 and CD40/gp39 Costimulation Pathways," 159(7): 3104-08 (1997).

Daly et al., "High Activity Suppression of Myeloid Progenitor Proliferation by Chimeric Mutants of Interleukin 8 and Platelet Factor 4," *J. Biol. Chem.*, 270(40):23282-23292 (Oct. 6, 1995).

Danoff et al., "Cloning, Genomic Organization, and Chromosomal Localization of the Scya5 Gene Encoding the Murine Chemokine RANTES," *J. Immunol.*, 152:1182-1189 (1994).

Daugherty, B.L. et al., "Cloning, Expression, and Characterization of the Human Eosinophil Eotaxin Receptor," *J. Exp. Med.*, 183:2349-2354 (May 1996).

Davis, C.B. et al., "Signal Transduction Due to HIV-1 Envelope Interactions with Chemokine Receptors CXCR4 or CCR5," *J. Exp. Med.*, 186:1793-1798 (1997).

Dean, M. et al., "Genetic Restriction of HIV-1 Infection and Progression to AIDS by a Deletion Allele of the CKR5 Structural Gene," *Science*, 273:1856-1862 (Sep. 27, 1996).

Decker et al., "Surgical Stress Induces a Shift in the Type-1/type-2 T-helper Cell Balance, Suggesting Down-regulation of Cell-mediated and Up-regulation of Antibody-mediated Immunity Commensurate to the Trauma," *Surgery*, 119(3):316-325 (1996).

Denholm et al., "Secretion of Monocyte Chemotactic Activity by Alveolar Macrophages," *Amer. J. Pathol.*, 135(3):571-580 (Sep., 1989).

Denholm and Lewis, "Monocyte Chemoattractants in Pigeon Aortic Atherosclerosis," *Amer. J. Pathol.*, 126:464-475 (1987).

Denholm and Phan, "The Effects of Bleomycin on Alveolar Macrophage Growth Factor Secretion," *Amer. J. Pathol.*, 134(2):355-363 (Feb., 1989).

Denholm and Stankus, "Differential Effects of Two Fluorescent Probes on Macrophage Migration as Assessed by Manual and Automated Methods," *Cytometry*, 19:366-369 (1995).

Denholm and Stankus., "Changes in the Expression of MCP-1 Receptors on Monocyte THP-1 Cells Following Differentiation to Macrophages with Phorbol Myristate Acetate," *Cytokine*, 7(5):436-440 (Jul., 1995).

Denizot et al., "PAF-Acether and Acetylhydrolase in Stool of Patients with Crohn's Disease," *Digestive Diseases and Sciences*, 37(3):432-437 (1992).

De Pitá et al., "T-helper 2 Involvement in the Pathogenesis of Bullous Pemphigoid: Role of Soluble CD30 (sCD30)," *Arch. Dermatol. Res.*, 289(12):667-670 (1997).

Depita et al., [needs title] *Arch. Dermatol Res.*, 289(12): 667-70 (1997).

Devergne et al., Production of the Rantes Chemokine by Macrophages and Endothelial Cells in Delayed-Type Hypersensitivity Reactions, *Challenges Mod. Med.*, 8:59-62 (1994).

Devi et al., "Biologic Activities of the Beta-chemokine TCA3 on Neutrophils and Macrophages," *J. Immunol.*, 154(10):5376-5383 (1995).

Dijkstra et al., "Multiple Sclerosis: Some Possible Therapeutic Opportunities," *Trends in Pharm. Rev.*, 14(4): 124-128 (1993).

Driscoll, K.E., "Macrophage Inflammatory Proteins: Biology and Role in Pulmonary Inflammation," *Exp. Lung Res.*, 20(6):473-490 (1994).

Dunlop et al., "Demonstration of Stem Cell Inhibition and Myeloprotective Effects of SCI/rhMIPIα In Vivo," *Blood*, 79(9):2221-2225 (May 1, 1992).

Ebisawa, M. T., et al., "Eosinophil Transendothelial Migration Induced by Cytokines III. Effect of the Chemokine RANTES," *J. Immunol.* 153: 2153 (1994).

Elghazali et al., "Elevated Plasma Levels of IgE in Plasmodium Falciparum-primed Individuals Reflect an Increased Ration of IL-4 to Interferon-gamma (IFN-γ)-producing Cells," *Clin. Exp. Immunol.*, 109(1):84-89 (1997).

Elstad et al., "Synthesis and Release of Platelet-Activating Factor by Stimulated Human Mononuclear Phagocytes," *J. Immunol.*, 140(5):1618-1624 (Mar. 1, 1988).

Endres et al., "CD4 Independent Infection by HIV-2 Is Mediated By Fusin/CXCR4," *Cell*, 87, 745-756 (1996).

Falk and Leonard., "Specificity and Reversibility of Chemotactic Deactivation of Human Monocytes," *Infection and Immunity*, 32(2):464-468 (May, 1981).

Farzan, M. et al., "HIV-1 Entry and Macrophage Inflammatory Protein-1β-mediated Signaling Are Independent Functions of the Chemokine Receptor CCR5*," *J. Biol. Chem.*, 272:6854-6857 (1997).

Federsppiel, B. et al., "Molecular Cloning of the cDNA and Chromosomal Localization of the Gene for a Putative Seven-Transmembrane Segment (7-TMS) Receptor Isolated from Human Spleen," *Genomics*, 16:707-712 (1993).

Fidel et al., "Vaginal-Associated Immunity in Women with Recurrent Vulvovaginal Candidiasis: Evidence for Vaginal Th1-Type Responses Following Intravaginal Challenge with *Candida* Antigen," *J. Infect. Dis.*, 176(3):728-739 (1995).

Foote et al., "Antibody Framework Residues Affecting the Conformation of the Hypervariable Loops," *J. Mol. Biol.*, 224:487-499 (1992).

Forssman et al., "Eotaxin-2, a Novel CC Chemokine that is Selective for the Chemokine Receptor CCR3, and Acts Like Eotaxin or Human Eosinophil and Basophil Leukocytes," *J. Exp. Med.*, 185 2171(1997).

Frigas et al., "The Eosinophil and the Pathophysiology of Asthma," *J. Allergy Clin. Immunol.*, 77:527 (1986).

Frömmel et al., "An Estimate on the Effect of Point Mutation and Natural Selection on the Rate of Amino Acid Replacement in Proteins," *J. Mol. Evol.*, 21:233-257 (1985).

Furukawa et al., "The Mechanism of Rabbit Platelet Aggregation Induced by 2,5-Di-(tert-butyl)-1,4-benzohydroquinone, an Inhibitor of Endoplasmic Reticulum $Ca^2$-ATPase," *Jpn. J. Pharmacol.*, 75(3):295-298 (1997).

Furakawa, et al., [needs title] *Jpn. J. Pharmacol.*, 75(3):295-298 (1997).

Gallatin, W.M. et al., "A cell-surface molecule involved in organ-specific homing of lymphocytes," *Nature*, 304:30-34 (1983).

Galli, C. et al., "Macrophage-derived Chemokine Production by Activated Human T Cells in Virto and In Vivo: Preferential Association with the Production of Type 2 Cytokines," *Eur. J. Immunol. 30(1)*: 204-10.(2000).

Gallucci et al., "Natural Adjuvants: Endogenous Activators of Dendritic Cells," *Nature Medicine*, 5(11):1249-1255 (1999).

Gao et al., "Structure and Functional Expression of the Human Macrophage Inflammatory Protein 1α/Rantes Receptor," *J. Exp. Med.*, 177:1421-1427 (May, 1993).

Garcia-Zepeda et al., "Human Monocyte Chemoattractant Protein (MCP)-4 Is a Novel CC Chemokine With Activities on Monocytes, Eosinophils, and Basophils Induced in Allergic and Nonallergic Inflammation That Signals Through the CC Chemokine Receptors (CCR)-2 and -3," *J. Immunol.*, 157:5613-26 (1996).

Garlisi et al., "T Cells Are Necessary For $Th_2$ Cytokine Production and Eosinophil Accumulation in Airways of Antigen-Challenged Allergic Mice," *Clin. Immunol. Immunopathol.*, 75:75-83 (1995).

Genbank D43767, "Molecular Cloning of a Novel T Cell-directed CC Chemokine Expressed in Thymus By Signal Sequence Trap Using Epstein-Barr Virus Vector," deposited by Imai, T et al., dated Sep. 11, 1996.

Genbank X85740, "Molecular Cloning and Functional Expression of a Novel CC Chemokine Receptor cDNA From a Human Basophilic Call Line," deposited by Power, C.A. et al., dated Jun. 4, 1996.

GenBank X90862, Molecular Cloning of Murine CC CKR-4 and High Affinity Binding of Chemokines to Murine and Human CC CKR-4 Deposited by Hoogewerf, A. J., dated Aug. 16, 1995.

Gerard et al., "Human Chemotaxis Receptor Genes Cluster at 19q13.3-13.4 Characterization of the Human C5a Receptor Gene," *Biochemistry*, 32:1243-1250 (1993).

Ghia, P. et al., "Chemoattractants MDC and TARC are Secreted By Malignant B-cell Precursors Following CD40 Ligation and Support the Migration of Leukemia-Specific T Cells," *Blood*, 98:533-40 (2001).

Godiska, R. et al., "Human Macrophage-derived Chemokine (MDC), a Novel Chemoattractant for Monocytes, Monocyte-derived Dendritic Cells, and Natural Killer Cells, " *J. Exp. Med.*, 185(9):1595-1604 (May 5, 1997).

Gray, "Inflammatory Bowel Disease," in *Scientific American Medicine*, Dale & Federman, (Eds.), New York, Scientific American , Inc., vol. 1, Chapter 4, Part IV, pp. 10-16 (1991).

Greiner et al., "Low-Grade B Cell Lymphomas of Mucosa-Associated Lymphoid Tissue (MALT-Type) Require CD40-Mediated Signaling and Th2-Type Cytokines for in Vitro Growth and Differentiation," *Am. J. Pathol.*, 150(5):1583-1593 (1997).

Gruss, H. J. et al., "Pleiotropic Effects of CD30 Ligand on CD30-expressing Cells and Lymphoma Cell Lines," Blood 83: 2045-56 (1994).

Handley et al., "Platelet Activating Factor and Inflammation in Atherogenesis: Targets for Drug Development," *Drug Dev. Res.*, 7:361-375 (1986).

Harada et al., "Essential Involvement of Interleukin-8 (IL-8) in acute inflammation," *J. leukocyte Biology*, 56:559-564 (Nov., 1994).

Hayashi et al., "Production and Function of Monocyte Chemoattractant Protein-1 and Other β-chemokine in Murine Glial Cells," *J. Neuroimmunol.*, 60(1-2):143-150 (1995).

Heath, H. et al., "Chemokine Receptor Usage by Human Eosinophils-the Importance of CCR3 Demonstrated Using An Antagonistic Monoclonal Antibody," *J. Clin. Invest.* 99: 178.

Herault et al., "Effect of SR121566A, a Patent GP llb-llla Antagonist on Platelet-mediated Thrombin Generation In Vitro and In Vivo," *Thromb. Haemost 79(2)*:383-388 (1988).

Hieshima, K. et al., "A Novel Human CC Chemokine PARC That Is Most Homologous to Macrophage-Inflammatory Protein, 1α/LD78α and Chemotactic for T Lymphocytes, but Not for Monocytes," *J. Immunology*, 159:1140-1149 (1997).

Hoffman et al., "Detection of platelet-activating factor in amniotic fluid of complicated pregnancies," *Am. J. Obstet Gynecol.*, 162(2):525-528 (1990).

Holmes et al., Structure and Functional Expression of a Human Interleukin-8 Receptor, *Science*, 253:1278-1280 (Sep. 13, 1991).

Holt, P.G., "Immunoregulation of the allergic reaction in the respiratory tract," *Eur. Respir. J. Suppl.*, 22:85s-89s (1996).

Hoogenboom, H.R., "Designing and optimizing library selection strategies for generating high-affinity antibodies," *TIBTECH*, 15:62-70 (1997).

Hoogewerf, A.J. et al., "Molecular Cloning of Murine CC CKR-4 and High Affinity Binding of Chemokines to Murine and Human CC CKR-4," *Biochem. Biophys. Res. Comm.*, 218(1):337-343.

Horuk et al., "Purification, Receptor, Binding Analysis, and Biological Characterization of Human Melanoma Growth Stimulating Activity (MGSA)," *J. Biol. Chem.*, 268(1):541-546 (Jan. 5, 1993).

Howard et al., "Chemokines: Progress Toward Identifying Molecular Targets for Therapeutic Agents," *TIBTECH*, 14(2):46-51 (1996).

Hsieh et al., "Increased Plasma Platelet-activating Factor in Children With Acute Asthmatic Attacks and Decreased in Vivo and in Vitro Production of Platelet-activating Factor After Immunotherapy," *J. Allergy Clin. Immunol.*, 91:650-657 (1993).

Hsueh, W. et al., "Platelet-activating Factor, Tumor Necrosis Factor, Hypoxia and Necrotizing Enterocolitis," *Acta Pediat. Suppl.*, 396:11-17 (1994).

Huang et al., "Th2 Responses Induce Humorally Mediated Injury in Experimental Anti-Glomerular Basement Membrane Glomerulonephritis," *J. Am. Soc. Neprol.*, 8(7): 1101-1108 (1997).

Hussell et al., "CD8$^+$T Cells Control Th2-driven Pathology During Pulmonary Respiratory Syncytial Virus Infection," *Eur. J./ Immunol.*, 27(12);3341-3349 (1997).

Imai, T. et al., "Molecular Cloning of a Novel T Cell-directed CC Chemokine Expressed in Thymus by Signal Sequence Trap Using Epstein-Barr Virus Vector," *Journal of Biological Chemistry*, 271(35):21514-21521 (Aug. 30, 1996).

Imai, T. et al., "The T Cell-directed CC Chemokine TARC Is a Highly Specific Biological Ligand for CC Chemokine Receptor 4," *Journal of Biological Chemistry*, 272(23): 15036-15036 (Jun. 6, 1997).

Imai, T. et al., "Identification and Molecular Characterization of Fractalkine Receptor CX$_3$CR1, which Mediates Both Leukocyte Migration and Adhesion," *Cell*, 91:521-530 (Nov. 14, 1997).

Imai, T. et al., "Macrophage-derived Chemokine (MDC) is a Functional Ligand for the CC Chemokine Receptor CCR4," *J. Biological Chemistry*, 273(3):1764-68 (1998).

Imai, T. et al., "Selective Recruitment of CCR4-bearing Th2 Cells Toward Antigen-Presenting Cells by the CC Chemokines Thymus and Activation-regulated Chemokine and Macrophage-derived Chemokine," *Int. Immunol.* 11(1): 81-88 (1999).

Inngjerdigen, M. et al., "Human NK Cells Express CC Chemokine Receptors 4 and 8 and Respond to Thymus and Activation-regulated Chemokine, Macrophage-derived Chemokine and I-309," *J. Immunol.* 164(8): 4048-54 (2000).

"In Vitro Assays of Lymphocyte Functions," in *Current Protocols Immunology*, Sections 3-4, Wiley and Sons (1992).

Jason et al., "Evidence for a Shift from a Type I Lymphocyte Pattern with HIV Disease Progression," *J. Acquir. Immune Defic. Syndrome Retrovirol.*, 10(4):471-476 (1995).

Jeske et al., "Effect of Glycoprotein Iib/IIIa Antagonists on the HIT Serum Induced Activation of Platelets," *Thromb. Res.*, 88(3):271-281 (1997).

Johansen et al., "Vaccination Promotes TH1-like Inflammation and Survival in Chronic *Pseudomonas aeruginosa* Pneumonia. A New Prophylactic Principle," *Behring Inst. Mitt.*, 98:269-273 (1997).

Jones, P.T. et al., "Replacing the Complementarity-determining Regions in a Human Antibody With Those From a Mouse," *Nature*, 321:522-525 (1986).

Kald et al., "Release of Platelet-Activating Factor in Acute Experimental Pancreatitis," *Pancreas*, 8(4):440-442 (1993).

Kanazawa, N. et al., "Fractalkine and Macrophage-derived Chemokine: T Cell-Attracting Chemokines Expressed in T Cell Area Dendritic Cells," *Eur. J. Immunol.* 29(6): 1925-32 (1999).

Karban et al., "TH1/TH2 Cytokine Profile In Celiac Disease," *Isr. J. Med. Sci.*, 33(3):209-214 (1997).

Katou, F. et al., "Macrophage-derived Chemokine (MDC/CCL22( and CCR 4 are involved in the formation of T lymphocte-dendritic cell clusters in Human Inflamed Skin and Seconary Lymphoid Tissue," *Am. J. Pathol.* 158(4): 1243-70 (2001).

Kelly, M.D. et al., "Cutting Edge: Dichotomous Effects of β-Chemokines on HIV Replication in Monocytes and Monocyte-Derived Macrophages," *J. Immunol.*, 160:3091-3095 (1998).

Kelner, G.S. et al., "Lymphotactin: A Cytokine That Represents a New Class of Chemokine," *Science*, 266:1395-1399 (Nov. 25, 1994).

Kelvin et al., "Chemokines and Serpentines: The Molecular Biology of Chemokine Receptors," *J. Leukocyte Biology*, 54:604-612 (Dec., 1993).

Kenney et al., "Splenic Cytokine Responses in Indian Kala-Azar Before and After Treatment," *J. Infect. Dis.*, 177:815-819 (1998).

Kettleborough et al., "Humanization of a Mouse Monoclonal Antibody by CDR-grafting: The Importance of Framework Residues on Loop Conformation," *Protein Engin.*, 4:773-783 (1991).

Khar et al., "AK-5 Tumor-induced Modulation of Host Immune Function: Upregulation of Th-1-type Cytokine Response Mediates Early Tumor Regression," *Cytokines Mol. Ther.*, 2(1)39-46 (1996).

Kikuchi,T. And Crystal, R. G., "Antigen-pulsed Dendritic Cells Expressing Macrophage-derived Chemokine Elicit Th2 Responses and Promote Specific Humoral Immunity," *J. Clin. Invest.*, 108: 917-27 (2001).

Kitching et al., "Interleukin-4 Deficiency Enhances Th1 Responses and Crescentic Glomerulonephritis in Mice," *Kidney Int.*, 53(1):112-118 (1998).

Klein, L. et al., "CD4 T Cell Tolerance to Human C-reactive Protein, an Inducible Serum Protein, is Mediated by Medullary Thymic Epithelium," *J. Exp. Med.* 188(1): 5-16 (1998).

Kowalska, M.A. et al., "Stromal Cell-derived factor-1 and Macrophage-derived Chemokine; 2 Chemokines that Activate Platelets," *Blood*, 96(1): 50-57. (2000).

Krishnan et al., "T Helper 1 Response Against *Leishmania major* in Pregnant C57BL/6 Mice Increases Implantation Failure and Fetal Resorptions," *J. Immunol.*, 156(2):653-662 (1996).

Kuby J., (Ed.), *Immunology*, W.H. Freeman and Co., New York, New York, pp. 304-306, 420-425, 488-490, 495-497, and 499-500 (1992).

Kuna et al., "RANTES, a Monocyte and T Lymphocyte Chemotactic Cytokine Releases Histamine from Human Basophils," *J. Immunology*, 149(2):636-642 (Jul. 15, 1992).

Kunkel et al., "Th1 and Th2 Responses Regulate Experimental Lung Granuloma Development," *Sarcoidosis Vasc. Diffuse Lung Dis.*, 13:120-128 (1996).

Laning et al., "Inhibition of In Vivo Tumor Growth by the β Chemokine, TCA3," *J. Immunology*, 153:4625-4635 (1994).

Li et al., "In Vivo Alterations in Cytokine Production following Interleukin-12 (IL-12) and Anti-IL-4 Antibody Treatment of CB6F1 Mice with Chronic Cutaneous Leishmaniasis," *Infect. Immunol.*, 64:5248-5254 (1996).

Liang et al., "Measurement of Systemic Lupus Erythematosus Activity in Clinical Research," *Arthritis Rheum.*, 31: 817-825 (1988).

Linder, M.E. et al., "G Proteins," *Scientific American, 267*: 56-65 (Jul. 1992).

Lindsberg et al., "Platelet-activating Factor in Stroke and Brain Injury," *Stroke, 21*:1452-1457 (1990).

Lindsberg et al., "Evidence for Platelet-Activating Factor as a Novel Mediator in Experimental Stroke in Rabbits," *Ann. Neurol., 30(2)*:117-129 (1991).

Lloyd, C. M. et al., "CC Chemokine Receptor (CCR)3/ Eotaxin Is Followed By CCR4/Monocyte-derived Chemokine in Mediating Pulmonary T Helper Lymphocyte Type 2 Recruitment After Serial Antigen Challenge In Vivo," J. Exp. Med. 191(2): 265-73 (2000).

Luo et al., Biologic Activities of the Murine β-Chemokine TCA3, *J. Immunology, 153*:4616-4624 (1994).

Luster, A.D. et al., "The IP-10 Chemokine Binds to a Specific Cell Surface Heparan Sulfate Site Shared with Platelet Factor 4 and Inhibits Endothelial Cell Proliferation," *J. Exp. Med., 182*:219-231 (Jul. 1995).

MacGlashan, D.W., Jr., and Guo, C.-B., "Oscillations in Free Cytosolic Calcium During IgE-mediated Stimulation Distinguish Human Basophils from Human Mast Cells," J. Immunol. 147: 2259 (1991).

Maggi E. et al., "Ability of HIV to Promote a $T_H1$ to $T_H0$ Shift and to Replicate Preferentially in $T_H2$ and $T_H0$ Cells," *Science, 265*:244-248 (1994).

Maggi et al., CD8+ T Lymphocytes Producing Th2-type Cytokines (Tc2) in HIV-infected Individuals, *J. Biol. Regul. Homeost. Agents, 9(3)*:78-81 (1995).

Major et al., "Oxidized LDL Selectively Potentiates LPS-Induced Chemokine mRNA Expression in Murine Peritoneal Macrophages," Thirty-first National Meeting of the Society for Leukocyte Biology on Host Defense Against Infections and Cancer, Marco Island, Florida, USA, Sep. 13-16, 1995. *Journal of Leukocyte Biology, 0(Supplement)*: 14 (1995) (ABSTRACT 47).

Malden et al., "The Influence of Oxidatively Modified Low Density Lipoproteins on Expression of Platelet-derived Growth Factor by Human Monocyte-derived Macrophages, " *J. Biol. Chem., 266(21)*:13901-13907 (Jul. 25, 1991).

Mantovani, A. et al., "Macrophage-derived Chemokine (MDC)," *J. Leukoc. Biol. 68(3)*: 400-4 (2000).

Matsukawa, A. et al., Pivotal Role of the CC Chemokine, Macrophage-Derived Chemokine, in the Innate Immune Response, *J. Immunol., 164(10)*:5362-8 (2000).

Matsumoto et al., "Platelet-Activating Factor in Broncholaveolar Lavage Fluid of Patients with Adult Respiratory Distress Syndrome," *Clin. Exp. Pharmocol. Physiol., 19*:509-515 (1992).

Matsumoto, K. et al., "Induction of Apoptosis in Human Eosinophils by Anti-fas Antibody Treatment in Vitro," *Blood*, 86: 1437 (1995).

Matsushima et al., "Purification and Characterization of a Novel Monocyte Chemotactic and Activating Factor Produced by a Human Myelomonocytic Cell Line," *J. Exp. Med., 169*:1485-1490 (Apr., 1989).

Matsuzaki et al., "PAF Acetylhydrolase Activities in Human Systemic Lupus Erythematosus and Lupus-prone Mice," *Clinica Chimica Acta, 210*:139-144 (1992).

Maze et al., "Myelosuppressive Effects in Vivo of Purified Recombinant Murine Macrophage Inflammatory Protein-1α," *J. Immunol., 149(3)*:1004-1009 (Aug. 1, 1992).

McColl, S., et al. Uncoupling of Early Signal Transduction Events From Effector Function in Human Peripheral Blood Neutrophils in Response to Recombinant Macrophage Inflammatory Proteins-1 Alpha and -1 Beta, *J. Immunol.* 150: 4550 (1993).

McCune et al., "The SCID-hu Mouse: A Small Animal Model for HIV Infection and Antiviral Testing," in *Progress in Immunol.*, vol. VII, Melchers et al.(Eds.), Springer-Verlag Berlin-Heidelberg, pp. 1046-1049 (1989).

McCune et al., "The Hematophtology of HIV-1 Disease: Experimental Analysis In Vivo," in *Human Hematopoiesis in SCID Mice*, M Roncarlo et al., (Eds.), Landes Publishing Co., New York New York, pp. 129-156 (1995).

Meurer et al. "Formation of Eosinophilic and Monocytic Intradermal Inflammatory Sites in the Dog by Injection of Human RANTES but not Human Monocyte Chemottractant Protein 1, Human Macrophage Inflammatory Protein 1α, or Human Interleukin 8," J. Exp. Med., 178: 1913-1921 (Dec., 1993).

Mezzano et al., "Detection of Platelet-Activating Factor in Plasma of Patients with Streptococcal Nephritis[1]," *J. Am. Soc. Nephrol., 4*:235-242 (1993).

Middleton, J. et al., "Transcytosis and Surface Presentation of IL-8 by Venular Endothelial Cells," *Cell*: 385-95 (1997).

Miller et al., "A Novel Polypeptide Secreted by Activated Human T Lymphocytes," *J. Immunology, 143(9)*:2907-2916 (Nov. 1, 1989).

Miossec, P., "Th1Th2 Cytokine Balance in Arthritits," *Arthritis Rheum, 40(12)*:2105-2115 (1997).

Moore, J.P., "Coreceptors: Implications for HIV Pathogenesis and Therapy," *Science, 276*:51-52 (Apr. 4, 1997).

Morrison and Oi, "Genetically Engineered Antibody Molecules," *Adv. Immunol., 44*:65-92 (1989).

Moser et al., "Chronic *Pseudomonas aeruginosa* lung infection is more severe in $Th_2$ responding BALB/c mice compared to $Th_1$ responding C3H/HeN mice," *APMIS, 105 (11)*:838-842. (1997).

Mosmann et al., "The Expanding Universe of T-cell Subsets: Th1, Th2 and More," *Immunol. Today, 17*:138-146 (1996).

Müller, F. et al., "Enhanced Interleukin-10 Production in Response to *Mycobacterium avium* Productsin Mononuclear Cells from Patients with Human Immunodeficiency Virus Infection," *Journal Infectious Diseases, 177*:586-594 (1998).

Murphy et al., "Cloning of Complimentary DNA Encoding a Functional Human Interleukin-8 Receptor," *Science, 253*: 1280-1283 (Sep. 13, 1991).

Murphy, P.M., "Chemokine Receptors: Structure, Function and Role in Microbial Pathogenesis," *Cytokine Growth Factor Rev., 7*: 47 (1996).

Nagira et al., "Molecular Cloning of a Novel Human CC Chemokine Secondary Lymphoid-Tissue Chemokine That Is a Potent Chemoattractant for Lymphocytes and Mapped to Chromosome 9p13*," *J. Biol. Chem., 272*:19518-19524 (1997).

Nakamura T. et al., "Roles of IL-4 and IFN-γ in Stabilizing the T Helper Cell Type 1 and 2 Phenotype," *J. Immunol., 158(6)*:2648-2653 (1997).

Nakao et al., "Structures of Human Genes Coding for Cytokine LD78 and Their Expression," *Mol. Cell. Biol., 10(7)*:3646-3658 (Jul., 1990).

Nakogawa et al., "Cytokine-Induced Neutrophil Chemoattractant (CINC)-2 α, a Novel Member of Rat G RO/CINCs, Is a Predominant Chemokine Produced by Lipopolysaccharide-Stimulated Rat Macrophages in Culture," *Biochem. Biophys. Res. Commun.*, 220(3):945-948 (1996).

Napolitano, M. et al., "Molecular Cloning of TER1, a Chemokine Receptor-Like Gene Expressed by Lymphoid Tissues," *Journal of Immunology*, 157:2759-2763 (1996).

Neote et al., Molecular Cloning, Functional Expression, and Signaling Characteristics of a C-C Chemokine Receptor, *Cell*, 72:415-425 (Feb. 12, 1993).

Ngo et al., "Computational Complexity, Protein Structure Prediction, and the Levinthal Paradox," *The Protein Folding Problem and Tertiary Structure Prediction*, K. Merz, Jr. and S. Le Grand, Editors, Birkhäuser Boston, pp. 433 and 492-495 (1994).

Nomiyama, H. et al., "Assignment of the Human CC Chemokine Gene TARC (SCYA17) to Chromosome 16q13," *Genomics*, 40:211-213 (1997).

Nomura, H. et al., "Molecular cloning of cDNAs encoding a LD78 receptor and putative leukocyte chemotactic peptide receptors," *International Immunology*, 5(10):1239-1249 (1993).

Oberlin E. et al., "The CXC chemokine SDF-1 is the ligand for LESTR/fusin and prevents infection by T-cell-line-adapted HIV-1," *Nature*, 382:833-835 (Aug. 29, 1996).

Oravecz et al., "Regulation of the Receptor Specificity and Function of the Chemokine RANTES (Regulated on Activation, Normal T Cell Expressed and Secreted) by Dipeptidyl Peptidase IV (CD26)-mediated Cleavage," *J. Exp. Med.*, 186:1865-1872 (1997).

Padlan, E.A., "A Possible Procedure for Reducing the Immunogenicity of Antibody Variable Domains While Preserving Their Ligand-binding Properties," *Molecular Immunology*, 28(4/5):489-498 (1991).

Paganelli et al., "Th2-type Cytokines, Hypereosinophilia, and Interleukin-5 in HIV Disease," *Allergy*,52(1):110-111 (1997).

Pal, R. et al., "Inhibition of HIV-1 Infection by the β-Chemokine MDC," *Science*, 278:695-698 (Oct. 24, 1997).

Panina-Bordignon, P. et al., "The C-C Chemokine Receptors CCR4 and CCR8 Identify Airway T Cells of Allergen-Challenged Atopic Asthmatics," *J. Clin. Invest.* 107(11): 1357-64 (2001).

Pellegrini et al., "Disregulation in TH1 and TH2 Subsets of CD4+ T Cells in Peripheral Blood of Colorectal Cancer Patients and Onvolvement in Cancer Establishment and Progression," *Cancer Immunol., Immunother.*, 43(1):1-8 (1996).

Peri et al., "A new monoclonal antibody (5D3-F7) which recognizes human monocyte-chemotactic protein-1 but not related chemokines. Development of a sandwich ELISA and in situ detection of producing cells," *J. Immunological Methods*, 174:249-257 (1994).

Perussia et al., "Terminal Differentiation Surface Antigens of Myelomoncytic Cells are Expressed in Human Promyelocytic Leukemia Cells (HL60) treated with Chemical Inducers," *Blood*, 58(4):836-843 (Oct., 1981).

Pettoello-Mantovani et al., "thy/liv-SCID-hu Mice: A System for Investigating the In Vivo Effects of Multidrug therapy on Plasma Viremia and Human Immunodeficiency Virus Replication in Lymphoid Tissues," *J. Infect. Diseases*, 177: 337 (1998).

Phan et al., "Fibrotic Mechanisms in Lung Disease," in *Immunology of Inflammation*, Chapter 4, Elsiever, pp. 121-162 (1983).

Phan and Fantome, "Inhibition of Bleomycin-induced Pulmonary Fibrosis By Lipopolysaccharide," *Lab. Invest.*, 50(5): 587-591 (May, 1984).

Picker et al., "Physiological and Molecular Mechanisms of Lymphocyte Homing," *Annu. Rev. Immunol.*, 10:561-591 (1992).

Ponath et al., "Cloning of the Human Eosinophil Chemoattractant, Eotaxin-Expression, Receptor Binding, and Functional Properties Suggest a Mechanism for the Selective Recruitment of Eosinophils," *J. Clin. Invest.*, 97:604-612 (1996).

Ponath et al., "Molecular Cloning and Characterization of a Human Eotaxin Receptor Expressed Selectively on Eosinophils," J. Exp. Med. 183: 2437 (1996).

Ponath, P.D. et al., "Molecular Cloning and Characterization of a Human Eotaxin Receptor Expressed Selectively on Eosinophils," *J. Exp. Med.*, 183:2437-2448 (Jun. 1996).

Pope et al., "Resistance of Naive Mice to Murine Hepatitis Virus Strain 3 Requires Development of a Th1, but not a Th2, Response, Whereas Pre-Existing Antibody Partially Protects Against Primary Infection[1]," *J. Immunol.*, 156(9): 3342-3349 (1996).

Power et al., "Molecular Cloning and Functional Expression of a Novel CC Chemokine Receptor cDNA from a Human Basophil Cell Line," *J. Biol. Chem.*, 270(33):19495-19500 (Aug. 18, 1995).

Price et al., "Expression, Purification, Characterization, of Recombinant Murine Granulocyte-macrophage Colony-stimulating Factor and Bovine Interleukin-2 From Yeast," *Gene*, 55:287-293 (1987).

Proost et al., "Amino-terminal Truncation of Chemokines by CD26/Dipeptidyl-peptidase IV," *J. Biol. Chem.*, 273(13): 7222-7227 (1998).

Proost et al., "Truncation of Macrophage-Derived Chemokine by CD26/Dipeptidy-Peptidase IV Beyond Its Predicted Cleavage Site Affects Chemotactic Activity and CC Chemokine Receptor 4 Interaction," J. Biol. Chem., 274(7): 3988-93 (1999).

Proudfoot et al., "Extension of Recombinant Human RANTES by the Retention of the Initiating Methionine Produces a Potent Antagonist*," *J. Biol. Chem.*, 271:2599-2603 (1996).

Punt, J. A. et al., "T Cell Receptor (TCR) Induced Death of Immature CD4+CD8+ Thymocytes by Two Distinct Mechanisms Differing in Their Requirements for CD28 Co-stimulation: Implications for Negative Selection in the Thymus," J. Exp. Med. 186: 1911-22 (1997).

Rabinovichi et al., "Platelet Activating Factor Mediates Interleukin-2-induced Lung Injury in the Rat," *J. Clin. Invest.*, 89:1669-1673 (1992).

Rabinovichi et al., "ARDS-like lung injury produced by endotoxin in platelet-activating factor-primed rats," *J. Appl. Physiol.*, 74(4):1791-1802 (1993).

Rader, C. et al., "Phage display of combinatorial antibody libraries," *Current Opinion Biotechnology*, 8:503-508 (1997).

Raport et al., "The Orphan G-Protein-Coupled Receptor-Encoding Gene V28 is Closely Related to Genes for Chemokine Receptors and is Expressed in Lymphoid and Neural Tissues," *Gene*, 163:295-299 (1995).

Raport, C.J., et al., "Molecular Cloning and Functional Characterization of a Novel Human CC Chemokine Receptor (CCR5) for RANTES, MIP-1β, MIP-1α," *J. Biological Chemistry, 271(29)*:17161-17166 (Jul. 19, 1996).

Reeves, J.D. et al., "CD4-Independent Infection by HIV-2 (ROD/B): Use of the 7-Transmembrane Receptors CXCR-4, CCR-3 and V28 for Entry," *Virology, 231*:130-134 (1997).

Ribeiro et al., "Partial Characterization of the RNA From LPS-stimulated Macrophages That Induces the Release of Chemotactic Cytokines by Resident Macrophages," *Mol. Cell. Biochem., 148(2)*:105-113 (1995).

Riechmann et al., "Reshaping Human Antibodies for Therapy," *Nature, 332*:323-327 (1988).

Robey, E. and Fowlkes, B. J., "Selective Events in T cell development," *Ann. Rev. Immunol. 12*:675-705 (1994).

Rodriguez-Roisin et al., "Platelet-activating Factor Causes Ventilation-Perfusion Mismatch in Humans," *J. Clin. Invest., 93*:188-194 (1994).

Roederer et al., "HIV Does Not Replicate in Naive CD4T Cells Stimulated with CD3/CD28," *J. Clin. Invest., 99(7)*:1555-1564 (1997).

Romagnani et al., "An Alternative View of the Th1/Th2 Switch Hypothesis in HIV Infection", *AIDS Res. Hum. Retroviruses, 10*: iii-ix (1994).

Romagnani, P., et al., "High CD30 Ligand Expression by Epithelial Cells and Hassal's Corpuscles in the Medulla of Human Thymus," Blood, 91: 3323-32 (1998).

Rook et al., "Gulf War syndrome: is it due to a systemic shift in cytokine balance towards a Th2 profile?," *Lancet, 349 (9068)*:1831-1833 (1997).

Roos, R.S. et al., "Identification of CCR8, the Receptor for the Human CC Chemokine I-309," *The Journal of Biological Chemistry, 272(28)*:17251-17254 (1997).

Ryan et al., "*Bordetella pertussis* Respiratory Infection in Children Is Associated with Preferential Activation of Type 1 T Helper Cells," *J. Infect. Dis., 175(5)*:1246-1250 (1997).

Sallusto, F. et al. "Selective Expression of the Eotaxin Receptor CCR3 by Human T Helper 2 Cells," Science 277: 2005 (1997).

Sambrook et al., *Molecular Cloning: A Laboratory Manual*, Cold Spring Harbor Laboratory, Cold Spring Harbor, New York, pp. 1.74-1.84, 1.90-1.104, 6.1-6.35, and Chapter 15 (1989).

Samson, M. et al., "Molecular Cloning and Chromosomal Mapping if a Novel Human Gene, ChemR1, Expressed in T Lymphocytes and Polymorphonuclear Cells and Encoding a Putative Chemokine Receptor," *Eur. J. Immunol., 26*:3021-3028, (1996).

Samson et al., "Molecular Cloning and Functional Expression of a New Human CC-Chemokine Receptor Gene," *Biochemistry, 35*:3362-3367 (1996).

Sarris et al., "Human Interferon-inducible Protein 10: Expression and Purification of Recombinant Protein Demonstrate Inhibition of Early Human Hematopoietic Progenitors," *J. Exp. Med., 178*:1127-1132 (Sep., 1993).

Satoh et al., "Platelet-Activating Factor Acetylhydrolase in Plasma Lipoproteins From Patients With Ischemic Stroke," *Stroke, 23*:1090-1092 (1992).

Schall et al., "A Human T Cell Specific Molecules a Member of a New Gene Family," *J. Immunology, 141(3)*:1018-1025 (Aug. 1, 1988).

Schall, T. J. et al., "Chemokines, Leukocyte Trafficking, and Inflammation," *Current Opinion in Immunology 6*:865-873 (1994).

Simmons G. et al., "Potent Inhibition of HIV-1 Infectivity in Macrophages and Lymphocytes by a Novel CCR5 Antagonist," *Science 276(5310)*: 276-279 (Apr. 11, 1997).

Smith, M. W. et al., "Contrasting Genetic Influence of CCR2 and CCR5 Variants on HIV-1 Infection and Disease Progression," *Science, 277*:959-965 (Aug. 15, 1997).

Sozzani, S. et al., "Receptor Expression and Responsiveness of Human Dendritic Cells to a Defined Set of CC and CXC Chemokines," J. Immunol. 159: 1993 (1997).

Sprent, J. et al., "T Cell Selection in the Thymus," *Immunol. Rev. 101*: 173-90 (1988).

Springer, "Traffic Signals for Lymphocyte Recirculation and Leukocyte Emigration: The Multistep Paradigm," *Cell, 76*: 301-314 (Jan. 28, 1994).

Spruance et al., "Th1/Th2-like Immunity and Resistance to Herpes Simplex Labialis," *Antiviral Res., 28(1)*:39-55 (1995).

Stafforini et al., "Human Macrophages Secrete Platelet-activating Factor Acetylhydrolase," *J. Biol. Chem., 265(17)*: 9682-9687 (Jun. 15, 1990).

Stanciu et al., "Increased Levels of IL-4 in CD8+ T Cells in Atopic Asthma," *J. Allergy Clin. Immunol., 100(3)*:373-378 (1997).

Staton, G. W. Jr. et al., "II ASTHMA," 14 Resp. Scientific American, Inc., pp. 1-20 (Mar. 1997).

Steinman, R.M., "The Dendritic Cell System and Its Role In Immunogenicity[1]," *Annu. Rev. Immunol., 9*:271-296 (1991).

Stellato et al., "Production of the Novel C-C Chemokine MCP-4 By Airway Cells and Comparison of Its Biological Activity to Other C-C Chemokines," *J. Clin. Invest., 99*: 926 (1997).

Stenberg et al., "Structural Analysis of the Major Immediate Early Gene of Human Cytomegalovirus," *J. Virology, 49(1)*: 190-199 (Jan., 1984).

Surh, C. D. and Sprent, J., "T-cell Apoptosis Detected in Situ During Positive and Negative Selection in the Thymus," Naute 372: 100-103 (1994).

Swanborg et al., "Experimental Autoimmune Encephalomyelitis in Rodents as a Model for Human Demyelinating Disease," *Clin. Immunol. Pathol. 77(1)*:4-13 (1995).

Szabo et al., "Chemokine Class Differences in Binding to the Duffy Antigen-Erythrocyte Chemokine Receptor," *J. Biol. Chem., 270(43)*:25348-25351 (1995).

Tanaka, Y., et al., "T-cell Adhesion Induced by Proteoglycan-immobilized cytokine MIP-1 beta," *Nature 361*: 79-82 (1993).

Tang, L. H. and Cyster, J. G., "Chemokine Up-Regulation and Activated T Cell Attraction by Maturing Dendritic Cells," *Science, 284*: 819-22 (1999).

Taub et al., "Chemokines, Inflammation, and the Immune System," *Therapeutic Immunology, 1*:229-246 (1994).

Taylor, M.L. et al., "Monocyte-derived Chemokine (MDC) Induces Human Eosinophil (EOS) Chemotaxis (CTX) and Shape Change in a CCR3-independent Manner," (Bruce Brodnur's Abstract) AAAA1 (Nov. 1998) (Abstract).

Tempest et al., Reshaping A Human Monoclonal Antibody To Inhibit Human Respiratory Syncytial Virus Infection In Vivo, *Bio/Technology, 9*:266-271 (1991).

Tiffany, H.L. et al., "Identification of CCR8: A Human Monocyte and Thymus Receptor for the CC Chemokine I-309," *Journal of Experimental Medicine, 186(1)*:165-170 (Jul. 7, 1997).

Tjoelker et al., "Anti-inflammatory Properties of a Platelet Activating Factor Acetylhydrolase," *Nature*, 374:549-553 (Apr. 6, 1995).

Tomioka, K., et al., "GM-CSF Regulates Human Eosinophil Responses to F-Met Peptide and Platelet Activating Factor," *J. Immunol.* 151: 4989 (1993).

Tuschil et al., "Interleukin-8 Stimulates Calcium Transients and Promotes Epidermal Cell Proliferation," *J. Invest. Dermatol.*, 99:294-298 (1992).

Uccini, S., et al., "Kaposi's Sarcoma Cells Express the Macrophage Associated Antigen Mannose Receptor and Develop in Peripheral Blood Cultures of Kaposi's Sarcoma Patients," *Am. J. Pathol.* 150: 929-38 (1997).

Uguccioni, M. et al., "Monocyte Chemotactic Protein 4 (MCP-4), a Novel Structural and Functional Analogue of MCP-3 and Eotaxin," J. Exp. Med. 183: 2379 (1996).

Uguccioni, M. et al., "High Expression of the Chemokine Receptor CCR3 in Human Blood Basophils-Role in Activation by Eotaxin, MCP-4, and other Chemokines," J. Clin. Invest. 100: 1137 (1997).

Umetsu, D.T. et al., "Th1 and Th2 CD4+ Cells in the Pathogenesis of Allergic Diseases," *Proc. Soc. Exp. Biol. Med.*, 215:11-20 (1997).

Van Damme et al., "Structural and Functional Identification of Two Human, Tumor-derived Monocyte Chemotactic Proteins (MPC-2 and MCP-3) Belonging to the Chemokine Family," *J. Exp. Med.*, 176:59-65 (Jul., 1992).

Van Kimmenade et al., "Expression, Renaturation and Purification of Recombinant Human Interleukin 4 From *Escherichia coli*," *Eur. J. Biochem.*, 173:109-114 (1988).

Van Roon et al., "Decrease in Peripheral Type 1 Over Type 2 T Cell Cytokine Production in Patients With Rheumatoid Arthritis Correlates With an Increase in Severity of Disease, " *Ann. Rheum. Dis.*, 56(11):656-660 (1997).

Van Snick, J., et al., "I-309/T Cell Activation Gene-3 Chemokine Protects Murine T cell Lymphomas Against Dexamethason Inuded Apoptosis," *J. Immunol.* 157: 25750-76 (1996).

Verhoeyen, M. et al., "Reshaping Human Antibodies: Grafting an Antilysozyme Activity," *Science*, 239:1534-1536 (1988).

Vicari, A. P., "TECK: a Novel CC Chemokine Specifically Expressed by Thymic Dendritic Cells and Potentially Involved in T cell Development," Immunity, 7: 291-301 (1997).

von Boehmer, H., "T-cell development: Is Notch a key player in lineage decisions?" *Current Biology,* 7:R308-R310 (1997).

Watanabe et al., "Pharmacological Analysis of Neutrophil Chemotactic Factor Production by Leucocytes and Roles of PAF in Allergic Inflammation in Rats," *Br. J. Pharmacol., 111*:123-130 (1994).

Weber et al., "Monocyte Chemotactic Protein MCP-2 Activates Human Basophil and Eosinophil Leukocytes Similar to MCP-3," *J. Immunology*, 154:4166-4172 (1995).

Weissman, D. et al., "Macrophage Tropic HIV and SIV Envelope Proteins Induce a Signal Through the CCR5 Chemokine Receptor," *Nature*, 389:981-985 (1997).

Wells et al., "Selectivity and Antagonism of Chemokine Receptors," *J. Leukocyte Biology,* 59:53-60 (Jan., 1996).

White et al., "Cloning and Functional Characterization of a Novel Human CC Chemokine that Binds to the CCR3 Receptor and Activates Human Eosinophils," *J. Leukoc. Biol. 62*: 667 (1997).

Wilson et al., "Expression and Characterization of TCA3: A Murine Inflammatory Protein," *J. Immunology, 145(8)*: 2745-2750 (Oct. 15, 1990).

Windhagen et al., "Role of Th1 and Th2 Cells in Neurologic Disorders," *Chem. Immunol.,* 63:171-186 (1996).

Winkler, C. et al., "Genetic Restriction of AIDS Pathogenesis by an SDF-1 Chemokine Gene Variant," *Science,* 279:389-393 (Jan. 16, 1998).

Winter, G. et al., "Antibody-based Therapy: Humanized antibodies," *TiPS, 14*:139-143 (May 1993).

Wofsy, D. and Seaman, W.E., "Reversal of Advanced Murine Lupus in NZB/NZW F1 Mice By Treatment With Monoclonal Antibody to L3T4," *J. Immunol. 138(10)*:3247-53 (1987).

Wolowczuk et al., "Interleukin-7 in the Skin of *Schistosoma mansoni*-infected Mice is Associated With a Decrease in Interferon-γ Production and Leads to an Aggravation of the Disease," *Immunol., 91(1)*:35-44 (1997).

Woods et al., "Loss of Inducible Virus in CD45RA Naive Cells After Human Immunodeficiency Virus-1 Entry Accounts for Preferential Viral Replication in CD34RO Memory Cells," *Blood,* 89:1635-1641 (1997).

Wu et al., "CCR5 Levels and Expression Pattern Correlate with Infectability by Macrophage-tropic HIV-1, In Vitro," *J. Exp. Med., 185(9)*:1681-1691 (1997).

Yamashita et al., "Increased Levels of Blood Platelet-activating Factor in Bronchial Asthmatic Patients with Active Symptoms," *Allergy,* 49:60-63 (1994).

Yeh et al., "Design of Yeast-secreted Albumin Derivatives for Human Therapy: Biological and Antiviral Properties of a Serum Albumin-CD4 Genetic Conjugate," *Proc. Natl. Acad. Sci., USA, 89(5)*:1904-1908 (1992).

Yoshida, T. et al., "Molecular Cloning of N novel C or γ Type Chemokine, SCM-1," *FEBS Letters, 360*:155-159 (1995).

Yoshimura et al., "Production and Characterization of Mouse Monoclonal Antibodies Against Human Monocyte Chemoattractant Protein-1," *J. Immunol., 147(7)*:2229-2233 (Oct., 1991).

Yoshimura, T., "cDNA Cloning of Guinea Pig Monocyte Chemoattractant Protein-1 and Expression of the Recombinant Protein," *J. Immunol., 150(11)*:5025-5032 (Jun. 1, 1993).

Zarco et al., "Involvement of Platelet-activating Factor and Tumour Necrosis Factor in the Pathogenesis of Joint Inflammation in Rabbits," *Clin. Exp. Immunol.,* 88:318-323 (1992).

International Search Report for PCT/US 98/20270, mailed Jul. 27, 1999.

Sallusto et al., "Flexible Programs of Chemokine Receptor Expression on Human Polarized T Helper 1 and 2 Lymphocytes," *J. Exp. Med.*, 187(6):875-883 (Mar. 16, 1998).

Yoshimura et al., cDNA Cloning and Expression of Guinea Pig Neutrophil Attractant Protein-1 (NAP-1). *J. Immunology,* 151(11):6225-6236 (Dec. 1, 1993).

* cited by examiner

FIG. 1

```
Hu MDC      MARLQTALLV VLVLLAVALQ ATEA GPYGAN MEDSVCCRDY VRYRLPLRVV  50
Hu MCP-3    M-KASAALLC LLLTAAAFSP QGLA QPVGIN -TSTTCCYRF INKKIPKQRL  48
Hu MCP-1    M-KVSAALLC LLLIAATFIP QGLA QPDAIN -APVTCCYNF TNRKISVQRL  48
Hu MCP-2    M-KVSAAALA VILIATALCA PASA QPD-SV SIPITCCFNV INRKIPIQRL  26
Hu RANTES   M-KLCVTVLS LLMLVAAFCS PALS SPY-SS -DTTPCCFAY IARPLPRAHI  47
Hu MIP-1β   M-QVSTAALA VLLCTMALCN QF-S APM-GS DPPTACCFSY T-REASSNFV  47
Hu MIP-1α   MQIITTALVC LLL-AGMWPE DVDS ASL-AA DTPTACCFSY TSRQIPQNFI  47
Hu I-309                              KS--MQ VPFSRCCFSF AEQEIPLRAI  47

Hu MDC      KH-FYWTSDS CPRPGVVLLT FRDKEICADP RVPWVKMILN KLSQ         93
Hu MCP-3    ESYRRTTSSH CPREAVIFKT KLDKEICADP TQKWVQDFMK HLDKKTQTPKL  99
Hu MCP-1    ASYRRITSSK CPKEAVIFKT IVAKEICADP KQKWVQDSMD HLDKQTQTPKT  99
Hu MCP-2    ESYTRITNIQ CPKEAVIFKT KRGKEVCADP KERWVRDSMK HLDQIFQNLKP  76
Hu RANTES   KEYFY-TSGK CSNPAVVFVT RKNRQVCANP EKKWVREYIN SLEMS        91
Hu MIP-1β   VDY-YETSSL CSQPAVVFQT KRSKQVCADP SESWVQEYVY DLELN        91
Hu MIP-1α   ADYF-ETSSQ CSKPGVIFLT KRSRQVCADP SEEWVQKYVS DLELSA       92
Hu I-309    LCY-RNTSSI CSNEGLIFKL KRGKEACALD TVGWVQRHRK MLRHCPSKRK   96
```

FIG. 9

```
  1 atctcgagct cacg ATG AGA TTT CCT TCA ATT TTT ACT GCA GTT TTA TTC
    tagagctcga gtgc TAC TCT AAA GGA AGT TAA AAA TGA CGT CAA AAT AAG 1▶Met Arg Phe Pro Ser Ile Phe Thr Ala Val Leu Phe
 51 GCA GCA TCC TCC GCA TTA GCT GCT CCA GTC AAC ACT ACA ACA GAA GAT
    CGT CGT AGG AGG CGT AAT CGA CGA GGT CAG TTG TGA TGT TGT CTT CTA 13▶Ala Ala Ser Ser Ala Leu Ala Ala Pro Val Asn Thr Thr Thr Glu Asp
 99 GAA ACG GCA CAA ATT CCG GCT GAA GCT GTC ATC GGT TAC TTA GAT TTA
    CTT TGC CGT GTT TAA GGC CGA CTT CGA CAG TAG CCA ATG AAT CTA AAT 29▶Glu Thr Ala Gln Ile Pro Ala Glu Ala Val Ile Gly Tyr Leu Asp Leu
                                    alpha Factor PrePro
147 GAA GGG GAT TTC GAT GTT GCT GTT TTG CCA TTT TCC AAC AGC ACA AAT
    CTT CCC CTA AAG CTA CAA CGA CAA AAC GGT AAA AGG TTG TCG TGT TTA 45▶Glu Gly Asp Phe Asp Val Ala Val Leu Pro Phe Ser Asn Ser Thr Asn
195 AAC GGG TTA TTG TTT ATA AAT ACT ACT ATT GCC AGC ATT GCT GCT AAA
    TTG CCC AAT AAC AAA TAT TTA TGA TGA TAA CGG TCG TAA CGA CGA TTT 61▶Asn Gly Leu Leu Phe Ile Asn Thr Thr Ile Ala Ser Ile Ala Ala Lys
          Asp7181                           Mature MDC Start
243 GAA GAA GGG GTA CCT TTG GAT AAA AGA GGC CCC TAC GGC GCC AAC ATG
    CTT CTT CCC CAT GGA AAC CTA TTT TCT CCG GGG ATG CCG CGG TTG TAC 77▶Glu Glu Gly Val Pro Leu Asp Lys Arg Gly Pro Tyr Gly Ala Asn Met
291 GAA GAC AGC GTC TGC TGC CGT GAT TAC GTC CGT TAC CGT CTG CCC CTG
    CTT CTG TCG CAG ACG ACG GCA CTA ATG CAG GCA ATG GCA GAC GGG GAC 93▶Glu Asp Ser Val Cys Cys Arg Asp Tyr Val Arg Tyr Arg Leu Pro Leu
339 CGC GTG GTG AAA CAC TTC TAC TGG ACC TCA GAC TCC TGC CCG AGG CCT
    GCG CAC CAC TTT GTG AAG ATG ACC TGG AGT CTG AGG ACG GGC TCC GGA 109▶Arg Val Val Lys His Phe Tyr Trp Thr Ser Asp Ser Cys Pro Arg Pro
387 GGC GTG GTG TTG CTA ACC TTC AGG GAT AAG GAG ATC TGT GCC GAT CCC
    CCG CAC CAC AAC GAT TGG AAG TCC CTA TTC CTC TAG ACA CGG CTA GGG 125▶Gly Val Val Leu Leu Thr Phe Arg Asp Lys Glu Ile Cys Ala Asp Pro
435 AGA GTG CCC TGG GTG AAG ATG ATT CTC AAT AAG CTG AGC AA TGA
    TCT CAC GGG ACC CAC TTC TAC TAA GAG TTA TTC GAC TCG GTT ACT 141▶Arg Val Pro Trp Val Lys Met Ile Leu Asn Lys Leu Ser Gln •••
                           NotI
480 AGGCCTtcta gaGCGGCCGC ATCGATA
    TCCGGAagat ctCGCCGGCG TAGCTAT
```

MACROPHAGE DERIVED CHEMOKINE (MDC), MDC ANALOGS, MDC INHIBITOR SUBSTANCES, AND USES THEREOF

This application is the U.S. national stage application corresponding to International Patent Application No. PCT/US98/20270, filed 28 Sep. 1998, which in turn is a continuation-in-part of U.S. patent application Ser. No. 09/067,447, filed Apr. 28, 1998 (now U.S. Pat. No. 6,737,513, issued May 18, 2004), and a continuation-in-part of U.S. patent application Ser. No. 08/939,107, filed Sep. 26, 1997 (now U.S. Pat. No. 6,498,015, issued Dec. 24, 2002), and a continuation-in-part of U.S. patent application Ser. No. 08/660,542, filed Jun. 7, 1996 (now U.S. Pat. No. 5,932,703, issued Aug. 3, 1999), and a continuation-in-part of U.S. patent application Ser. No. 08/558,658, filed Nov. 16, 1995 (now abandoned), and a continuation-in-part of U.S. patent application Ser. No. 08/479,620, filed Jun. 7, 1995 (now U.S. Pat. No. 6,790,947, issued Sep. 14, 2004). All of these priority applications are incorporated by reference in their entirety.

FIELD OF THE INVENTION

The present invention relates generally to chemokines and more particularly to purified and isolated polynucleotides encoding a novel human C—C chemokine, to purified and isolated chemokine protein encoded by the polynucleotides, to chemokine analogs, to materials and methods for the recombinant production of the novel chemokine protein and analogs, to antibodies reactive with the novel chemokine, to chemokine inhibitors, and to uses of all of the foregoing materials. Of particular interest is the use of chemokine inhibitor substances to treat allergic conditions such as asthma.

BACKGROUND

Chemokines, also known as "intercrines" and "SIS cytokines", comprise a family of small secreted proteins (e.g., 70–100 amino acids and about 8–10 kiloDaltons) which attract and activate leukocytes and thereby aid in the stimulation and regulation of the immune system. The name "chemokine" is derived from chemotactic cytokine, and refers to the ability of these proteins to stimulate chemotaxis of leukocytes. Indeed, chemokines may comprise the main attractants for inflammatory cells into pathological tissues. See generally, Baggiolini et al., *Annu. Rev. Immunol,* 15: 675–705 (1997); and Baggiolini et al., *Advances in Immunology,* 55:97–179 (1994), both of which are incorporated by reference herein. While leukocytes comprise a rich source of chemokines, several chemokines are expressed in a multitude of tissues. Baggiolini et al. (1994), Table II.

Previously identified chemokines generally exhibit 20–70% amino acid identity to each other and contain four highly-conserved cysteine residues. Based on the relative position of the first two of these cysteine residues, chemokines have been further classified into two subfamilies. In the "C-X-C" or "α" subfamily, encoded by genes localized to human chromosome 4, the first two cysteines are separated by one amino acid. In the "C—C" or "β" subfamily, encoded by genes on human chromosome 17, the first two cysteines are adjacent. X-ray crystallography and NMR studies of several chemokines have indicated that, in each family, the first and third cysteines form a first disulfide bridge, and the second and fourth cysteines form a second disulfide bridge, strongly influencing the native conformation of the proteins. In humans alone, more than ten distinct sequences have been described for each chemokine subfamily. Chemokines of both subfamilies have characteristic leader sequences of twenty to twenty-five amino acids.

The C-X-C chemokines, which include IL-8, GROα/β/γ, platelet basic protein, Platelet Factor 4 (PF4), IP-10, NAP2, and others, share approximately 25% to 60% identity when any two amino acid sequences are compared (except for the GROα/β/γ members, which are 84–88% identical with each other). Most of the C-X-C chemokines (excluding IP-10 and Platelet Factor 4) share a common E-L-R tri-peptide motif upstream of the first two cysteine residues, and are potent stimulants of neutrophils, causing rapid shape change, chemotaxis, respiratory bursts, and degranulation. These effects are mediated by seven-transmembrane-domain rhodopsin-like G protein-coupled receptors; a receptor specific for IL-8 has been cloned by Holmes et al., *Science,* 253:1278–80 (1991), while a similar receptor (77% identity) which recognizes IL-8, GRO and NAP2 has been cloned by Murphy and Tiffany, *Science,* 253:1280–83 (1991). Progressive truncation of the N-terminal amino acid sequence of certain C-X-C chemokines, including IL-8, is associated with marked increases in activity.

The C—C chemokines, which include Macrophage Inflammatory Proteins MIP-1α and MIP-1β, Monocyte chemoattractant proteins 1, 2, 3, and 4 (MCP-1/2/3/4), RANTES, I-309, eotaxin, TARC, and others, share 25% to 70% amino acid identity with each other. Previously-identified C—C chemokines activate monocytes, causing calcium flux and chemotaxis. More selective effects are seen on lymphocytes, for example, T lymphocytes, which respond best to RANTES. Several seven-transmembrane-domain G protein-coupled receptors for C—C chemokines have been cloned to date, including a C—C chemokine receptor-1 (CCR1) which recognizes, e.g., MIP-1α and RANTES (Neote et al., *Cell,* 72:415–425 (1993)); a CCR2 receptor which has two splice variants and which recognizes, e.g., MCP-1 (Charo et al., *Proc. Nat. Acad. Sci.,* 91:2752–56 (1994)); CCR3, which recognizes, e.g., eotaxin, RANTES, and MCP-3 (Combadiere, *J. Biol. Chem.,* 270:16491 (1995)); CCR4, which recognizes MIP-1α, RANTES, and MCP-1 (Power et al., *J. Biol. Chem.,* 270:19495 (1995)); and CCR5, which recognizes MIP-1α, MIP-1β, and RANTES (Samson et al., *Biochemstry,* 35:3362 (1996)). Several CC chemokines have been shown to act as attractants for activated T lymphocytes. See Baggiolini et al. (1997).

Truncation of the N-terminal amino acid sequence of certain C—C chemokines also has been associated with alterations in activity. For example, mature RANTES (1–68) is processed by CD26 (a dipeptidyl aminopeptidase specific for the sequence $NH_2$-X-Pro- . . . ) to generate a RANTES (3–68) form that is capable of interacting with and transducing a signal through CCR5 (like the RANTES (1–68) form), but is one hundred-fold reduced in its capacity to stimulate through the receptor CCR1. See Proost et al., *J. Biol. Chem.,* 273(13): 7222–7227 (1998); and Oravecz et al., *J. Exp. Med.,* 186: 1865–1872 (1997). U.S. Pat. Nos. 5,459, 128, 5,705,360, and 5,739,103 to Rollins and Zhang purport to describe N-terminal deletions of chemokine MCP-1 that inhibit receptor binding to the corresponding endogenous chemokine.

The roles of a number of chemokines, particularly IL-8, have been well documented in various pathological conditions. See generally Baggiolini et al. (1994), supra, Table VII. Psoriasis, for example, has been linked to over-production of IL-8, and several studies have observed high levels of IL-8 in the synovial fluid of inflamed joints of patients suffering from rheumatic diseases, osteoarthritis, and gout.

The role of C—C chemokines in pathological conditions also has been documented, albeit less comprehensively than the role of IL-8. For example, the concentration of MCP-1 is higher in the synovial fluid of patients suffering from rheumatoid arthritis than that of patients suffering from other arthritic diseases. The MCP-1 dependent influx of mononuclear phagocytes may be an important event in the development of idiopathic pulmonary fibrosis. The role of C—C chemokines in the recruitment of monocytes into atherosclerotic areas is currently of intense interest, with enhanced MCP-1 expression having been detected in macrophage-rich arterial wall areas but not in normal arterial tissue. Expression of MCP-1 in malignant cells has been shown to suppress the ability of such cells to form tumors in vivo. (See U.S. Pat. No. 5,179,078, incorporated herein by reference.) A need therefore exists for the identification and characterization of additional C—C chemokines, to further elucidate the role of this important family of molecules in pathological conditions, and to develop improved treatments for such conditions utilizing chemokine-derived products.

With respect to the involvement of chemokines in allergic diseases, interest has focused on chemokines belonging to the CC family, such as RANTES, eotaxin, eotaxin-2, MCP-3 and MCP4, because of their ability to cause migration of human eosinophils in vitro and in vivo.

The ability of these chemokines to selectively activate human eosinophil migration appears to be due primarily to their activation of chemokine receptor CCR3. A need exists to elucidate the involvement of these and other chemokines in eosinophil stimulation and activation, to facilitate better treatments for late-phase allergic reactions, such as asthma [see Aalbers et al., *Eur. Respir. J.*, 6:840(1993); and Frigas et al., *J. Allergy Clin. Immunol.*, 77:527(1986)], in which eosinophil activation and migration have been implicated.

Chemokines of the C—C subfamily have been shown to possess utility in medical imaging, e.g., for imaging sites of infection, inflammation, and other sites having C—C chemokine receptor molecules. See, e.g., Kunkel et al., U.S. Pat. No. 5,413,778, incorporated herein by reference. Such methods involve chemical attachment of a labeling agent (e.g., a radioactive isotope) to the C—C chemokine using art recognized techniques (see, e.g., U.S. Pat. Nos. 4,965,392 and 5,037,630, incorporated herein by reference), administration of the labeled chemokine to a subject in a pharmaceutically acceptable carrier, allowing the labeled chemokine to accumulate at a target site, and imaging the labeled chemokine in vivo at the target site. A need in the art exists for additional new C—C chemokines to increase the available arsenal of medical imaging tools.

The C—C chemokines RANTES, MIP-α, and MIP-1μ also have been shown to be the primary mediators of the suppressive effect of human T cells on the human immunodeficiency virus (HIV), the agent responsible for causing human Acquired Immune Deficiency Syndrome (AIDS). These chemokines show a dose-dependent ability to inhibit specific strains of HIV from infecting cultured T cell lines [Cocchi et al., *Science*, 270:1811 (1995)]. In addition, International patent publication number WO 97/44462, filed by Institut Pasteur, describes the use of fragments and analogs of the chemokine RANTES as antagonists, to block RANTES interaction with its receptors, for the purpose of suppressing HIV. The C-X-C chemokine stromal derived factor-1 (SDF-1) also is capable of blocking infection by T-tropic HIV-1 strains. See Winkler et al., *Science*, 279: 389–393 (1998). However, the processes through which chemokines exert their protective effects have not been fully elucidated, and these chemokines in fact may stimulate HIV replication in cells exposed to the chemokines before HIV infection. See Kelly et al., *J. Immunol.*, 160:3091–3095 (1998). Moreover, not all tested strains of the virus are equally susceptible to the inhibitory effects of chemokines; therefore, a need exists for additional C—C chemokines for use as inhibitors of strains of HIV.

Similarly, it has been established that certain chemokine receptors such as CCR5 [International Patent Publication No. WO 97/44055, published 27 Nov. 1997], CCR8, CCR2, and CXCR4) are essential co-receptors (with the CD4 receptor) for mV-1 entry into susceptible cells, and that progression to AIDS is delayed in patients having certain variant alleles of these receptors. A need exists for additional therapeutics to inhibit HIV-1 infection and/or proliferation by interfering with HIV-1 entry and/or proliferation in susceptible cells.

More generally, due to the importance of chemokines as mediators of chemotaxis and inflammation, a need exists for the identification and isolation of new members of the chemokine family to facilitate modulation of inflammatory and immune responses.

For example, substances that promote inflammation may promote the healing of wounds or the speed of recovery from conditions such as pneumonia, where inflammation is important to eradication of infection. Modulation of inflammation is similarly important in pathological conditions manifested by inflammation. Crohn's disease, manifested by chronic inflammation of all layers of the bowel, pain, and diarrhea, is one such pathological condition. The failure rate of drug therapy for Crohn's disease is relatively high, and the disease is often recurrent even in patients receiving surgical intervention. The identification, isolation, and characterization of novel chemokines facilitates modulation of inflammation.

Similarly, substances that induce an immune response may promote palliation or healing of any number of pathological conditions. Due to the important role of leukocytes (e.g., neutrophils and monocytes) in cell-mediated immune responses, and due to the established role of chemokines in leukocyte chemotaxis, a need exists for the identification and isolation of new chemokines to facilitate modulation of immune responses.

Additionally, the established correlation between chemokine expression and inflammatory conditions and disease states provides diagnostic and prognostic indications for the use of chemokines, as well as for antibody substances that are specifically immunoreactive with chemokines; a need exists for the identification and isolation of new chemokines to facilitate such diagnostic and prognostic indications.

In addition to their ability to attract and activate leukocytes, some chemokines, such as L-8, have been shown to be capable of affecting the proliferation of non-leukocytic cells. See Tuschil, *J. Invest. Dermatol.*, 99:294–298 (1992). A need exists for the identification and isolation of new chemokines to facilitate modulation of such cell proliferation.

It will also be apparent from the foregoing discussion of chemokine activities that a need exists for modulators of chemokine activities, to inhibit the effects of endogenously-produced chemokines and/or to promote the activities of endogenously-produced or exogenously administered chemokines. Such modulators typically include small molecules, peptides, chemokine fragments and analogs, and/or antibody substances. Chemokine inhibitors interfere with chemokine signal transduction, i.e., by binding chemokine molecules, by competitively or non-competitively binding chemokine receptors, and/or by interfering with signal transduction downstream from the chemokine receptors. A need exists in the art for effective assays to rapidly screen putative chemokine modulators for modulating activity.

For all of the aforementioned reasons, a need exists for recombinant methods of production of newly discovered chemokines, which methods facilitate clinical applications involving the chemokines and chemokine inhibitors.

SUMMARY OF THE INVENTION

The present invention provides novel purified and isolated polynucleotides and polypeptides, antibodies, and methods and assays that fulfill one or more of the needs outlined above.

For example, the invention provides purified and isolated polynucleotides (i.e., DNA and RNA, both sense and antisense strands) encoding a novel human chemokine of the C—C subfamily, herein designated "Macrophage Derived Chemokine" or "MDC". Preferred DNA sequences of the invention include genomic and cDNA sequences and chemically synthesized DNA sequences. The cDNA and deduced amino acid sequence of human MDC has been published. See, e.g., International Patent Publication No. WO 96/40923, published 19 Dec. 1996; and Godiska et al., *J. Exp. Med.*, 185(9): 1595–1604 (1997). Compare International Publication No. WO 96/39521 (12 Dec. 1996); and Chang et al., *J. Biol. Chem.*, 272(40): 25229–25237 (1997).

Polynucleotides encoding non-human vertebrate forms of MDC, especially mammalian and avian forms of MDC, also are intended as aspects of the invention.

The nucleotide sequence of a cDNA, designated MDC cDNA, encoding this chemokine, is set forth in SEQ ID NO: 1, which sequence includes 5' and 3' non-coding sequences. A preferred DNA of the present invention comprises nucleotides 20 to 298 of SEQ ID NO: 1, which nucleotides comprise the MDC coding sequence.

The human MDC protein comprises a putative twenty-four amino acid signal sequence at its amino terminus. Another preferred DNA of the present invention comprises nucleotides 92 to 298 of SEQ ID NO: 1, which nucleotides comprise the putative coding sequence of the mature (secreted) MDC protein, without the signal sequence.

The amino acid sequence of human chemokine MDC is set forth in SEQ ID NO: 2. Preferred polynucleotides of the present invention include, in addition to those polynucleotides described above, polynucleotides that encode the amino acid sequence set forth in SEQ ID NO: 2, and that differ from the polynucleotides described in the preceding paragraphs only due to the well-known degeneracy of the genetic code.

Similarly, since twenty-four amino acids (positions −24 to −1) of SEQ ID NO: 2 comprise a putative signal peptide that is cleaved to yield the mature MDC chemokine, preferred polynucleotides include those which encode amino acids 1 to 69 of SEQ ID NO: 2. Thus, a preferred polynucleotide is a purified polynucleotide encoding a polypeptide having an amino acid sequence comprising amino acids 1–69 of SEQ ID NO: 2.

Among the uses for the polynucleotides of the present invention is the use as a hybridization probe, to identify and isolate genomic DNA encoding human MDC, which gene is likely to have a three exon/two intron structure characteristic of C—C chemokines genes. (See Baggiolini et al. (1994), supra); to identify and isolate DNAs having sequences encoding non-human proteins homologous to MDC; to identify human and non-human chemokine genes having similarity to the MDC gene; and to identify those cells which express MDC and the conditions under which this protein is expressed. Polynucleotides encoding human MDC have been employed to successfully isolate polynucleotides encoding at least three exemplary non-human embodiments of MDC (rat, mouse, macaque). (See SEQ ID NOs: 35–38 & 45–46.)

Hybridization probes of the invention also have diagnostic utility, e.g., for screening for inflammation in human tissue, such as colon tissue. More particularly, hybridization studies using an MDC polynucleotide hybridization probe distinguished colon tissue of patients with Crohn's disease (MDC hybridization detected in epithelium, lamina propria, Payer's patches, and smooth muscle) from normal human colon tissue (no hybridization above background).

Generally speaking, a continuous portion of the MDC cDNA of the invention that is at least about 14 nucleotides, and preferably about 18 nucleotides, is useful as a hybridization probe of the invention. Thus, in one embodiment, the invention includes a DNA comprising a continuous portion of the nucleotide sequence of SEQ ID NO: 1 or of the non-coding strand complementary thereto, the continuous portion comprising at least 18 nucleotides, the DNA being capable of hybridizing under stringent conditions to a coding or non-coding strand of a human MDC gene. For diagnostic utilities, hybridization probes of the invention preferably show hybridization specificity for MDC gene sequences. Thus, in a preferred embodiment, hybridization probe DNAs of the invention fail to hybridize under the stringent conditions to other human chemokine genes (e.g., MCP-1 genes, MCP-2 genes, MCP-3 genes, RANTES genes, MIP-1α genes, MIP-1β genes, and I-309 genes, etc.).

In another aspect, the invention provides a purified polynucleotide which hybridizes under stringent conditions to the non-coding strand of the DNA of SEQ ID NO: 1. Similarly, the invention provides a purified polynucleotide which, but for the redundancy of the genetic code, would hybridize under stringent conditions to the non-coding strand of the DNA of SEQ ID NO: 1. Exemplary stringent hybridization conditions are as follows: hybridization at 42° C. in 5×SSC, 20 mM NaPO$_4$, pH 6.8, 50% formamide; and washing at 42° C. in 0.2×SSC. Those skilled in the art understand that it is desirable to vary these conditions empirically based on the length and the GC nucleotide base content of the sequences to be hybridized, and that formulas for determining such variation exist. [See, e.g., Sambrook et al., *Molecular Cloning: a Laboratory Manual*. Second Edition, Cold Spring Harbor, N.Y.: Cold Spring Harbor Laboratory (1989).]

In another aspect, the invention includes plasmid and viral DNA vectors incorporating DNAs of the invention, including any of the DNAs described above or elsewhere herein. Preferred vectors include expression vectors in which the incorporated MDC-encoding cDNA is operatively linked to an endogenous or heterologous expression control sequence. Such expression vectors may further include polypeptide-encoding DNA sequences operably linked to the MDC-encoding DNA sequences, which vectors may be expressed to yield a fusion protein comprising the MDC polypeptide of interest.

In another aspect, the invention includes a prokaryotic or eukaryotic host cell stably transfected or transformed with a DNA or vector of the present invention. In preferred host cells, the mature MDC polypeptide encoded by the DNA or vector of the invention is expressed. The DNAs, vectors, and host cells of the present invention are useful, e.g., in methods for the recombinant production of large quantities of MDC polypeptides of the present invention. Such methods are themselves aspects of the invention. For example, the invention includes a method for producing MDC wherein a host cell of the invention is grown in a suitable nutrient medium and MDC protein is isolated from the cell or the medium.

Knowledge of DNA sequences encoding MDC makes possible determination of the chromosomal location of MDC coding sequences, as well as identification and isolation by DNA/DNA hybridization of genomic DNA sequences encoding the MDC expression control regulatory sequences such as promoters, operators, and the like.

According to another aspect of the invention, host cells may be modified by activating an endogenous MDC gene that is not normally expressed in the host cells or that is expressed at a lower level than is desired. Such host cells are modified (e.g., by homologous recombination) to express MDC by replacing, in whole or in part, the naturally-occurring MDC promoter with part or all of a heterologous promoter so that the host cells express MDC. In such host cells, the heterologous promoter DNA is operatively linked to the MDC coding sequences, i.e., controls transcription of the MDC coding sequences. See, for example, PCT International Publication No. WO 94/12650; PCT International Publication No. WO 92/20808; and PCT International Publication No. WO 91/09955. The invention also contemplates that, in addition to heterologous promoter DNA, amplifiable marker DNA (e.g., ada, dhfr, and the multi-functional CAD gene which encodes carbamyl phosphate synthase, aspartate transcarbamylase, and dihydro-orotase) and/or intron DNA may be recombined along with the heterologous promoter DNA into the host cells. If linked to the MDC coding sequences, amplification of the marker DNA by standard selection methods results in co-amplification of the MDC coding sequences in such host cells.

The DNA sequence information provided by the present invention also makes possible the development, by homologous recombination or "knockout" strategies [see, Capecchi, Science, 244: 1288–1292 (1989)], of rodents that fail to express functional MDC or that express a variant of MDC. Such rodents are useful as models for studying the activities of MDC, MDC variants, and MDC modulators in vivo. Rodents having a humanized immune system are useful as models for studying the activities of MDC and MDC modulators toward HIV infection and proliferation.

In yet another aspect, the invention includes purified and isolated MDC polypeptides. Mammalian and avian MDC polypeptides are specifically contemplated. A preferred peptide is a purified chemokine polypeptide having an amino acid sequence comprising amino acids 1 to 69 of SEQ ID NO: 2 (human mature MDC). Throughout the application, human mature MDC usually will be referred to simply as "MDC" or as "mature MDC". In instances where context warrants, such as certain descriptions of experiments that involve both human and non-human mature MDCs and/or that involve MDC fragments and analogs, human mature MDC will sometimes be specifically referred to as "human" and will sometimes be referred to as "MDC(1–69)."

Mouse and Rat MDC polypeptides of the invention are taught in SEQ ID NOs: 36 and 38. The sequence in SEQ ID NO: 36 depicts a complete murine MDC, consisting of a 24 residue leader peptide (residues −24 to −1 of SEQ ID NO: 36) and a 68 residue murine mature MDC. The sequence in SEQ ID NO: 38 depicts a partial rat MDC, consisting of 13 residues of the leader peptide (residues −13 to −1) and the complete 68 residue rat mature MDC.

The polypeptides of the present invention may be purified from natural sources, but are preferably produced by recombinant procedures, using the DNAs, vectors, and/or host cells of the present invention, or are chemically synthesized. Purified polypeptides of the invention may be glycosylated or non-glycosylated, water soluble or insoluble, oxidized, reduced, etc., depending on the host cell selected, recombinant production method, isolation method, processing, storage buffer, and the like.

Moreover, an aspect of the invention includes MDC polypeptide analogs wherein one or more amino acid residues is added, deleted, or replaced from the MDC polypeptides of the present invention, which analogs retain one or more of the biological activities characteristic of the C—C chemokines, especially of MDC. The small size of MDC facilitates chemical synthesis of such polypeptide analogs, which may be screened for MDC biological activities (e.g., the ability to induce macrophage chemotaxis, or inhibit monocyte chemotaxis) using the many activity assays described herein. Alternatively, such polypeptide analogs may be produced recombinantly using well-known procedures, such as site-directed mutagenesis of MDC-encoding DNAs of the invention, followed by recombinant expression of the resultant DNAs.

In a related aspect, the invention includes polypeptide analogs wherein one or more amino acid residues is added, deleted, or replaced from the MDC polypeptides of the present invention, which analogs lack the biological activities of C—C chemokines or MDC, but which are capable of competitively or non-competitively inhibiting the binding of MDC polypeptides with a C—C chemokine receptor. Such polypeptides are useful, e.g., for modulating the biological activity of endogenous MDC in a host, as well as useful for medical imaging methods described above.

Certain specific analogs of MDC are contemplated to modulate the structure, intermolecular binding characteristics, and biological activities of MDC. For example, amino-terminal (N-terminal) and carboxy-terminal (C-terminal) deletion analogs (truncations) are specifically contemplated to change MDC structure and function. Among the amino terminal deletion analogs that are specifically contemplated are analogs wherein 1, 2, 3, 4, 5, 6, 7, 8, 9, 10, or 11 amino terminal residues have been deleted (i.e., deletions up to the conserved cysteine pair at positions 12 and 13 of human, murine, and rat mature MDC). As set forth in detail below, experimental data indicates that most or all of these analogs will possess reduced MDC biological activities and, in fact, will act as inhibitors of one or more biological activities of mature MDC.

Additionally, the following single-amino acid alterations (alone or in combination) are specifically contemplated: (1) substitution of a non-basic amino acid for the basic arginine and/or lysine amino acids at positions 24 and 27, respectively, of SEQ ID NO: 2; (2) substitution of a charged or polar amino acid (e.g., serine, lysine, arginine, histidine, aspartate, glutamate, asparagine, glutamine or cysteine) for the tyrosine amino acid at position 30 of SEQ ID NO: 2, the tryptophan amino acid at position 59 of SEQ ID NO: 2, and/or the valine amino acid at position 60 of SEQ ID NO: 2; and (3) substitution of a basic or small, non-charged amino acid (e.g., lysine, arginine, histidine, glycine, alanine) for the glutamic acid amino acid at position 50 of SEQ ID NO: 2. Specific analogs having these amino acid alterations are encompassed by the following formula (SEQ ID NO: 25):

```
Met Ala Arg Leu Gln Thr Ala Leu Leu Val Val Leu Val Leu Leu Ala
-24             -20                 -15                 -10

Val Ala Leu Gln Ala Thr Glu Ala Gly Pro Tyr Gly Ala Asn Met Glu
             -5                   1               5

Asp Ser Val Cys Cys Arg Asp Tyr Val Arg Tyr Arg Leu Pro Leu Xaa
         10              15              20

Val Val Xaa His Phe Xaa Trp Thr Ser Asp Ser Cys Pro Arg Pro Gly
 25              30              35                      40

Val Val Leu Leu Thr Phe Arg Asp Lys Xaa Ile Cys Ala Asp Pro Arg
                 45              50              55

Val Pro Xaa Xaa Lys Met Ile Leu Asn Lys Leu Ser Gln
             60              65
``` wherein the amino acid at position 24 is selected from the group consisting of arginine, glycine, alanine, valine, leucine, isoleucine, proline, serine, threonine, phenylalanine, tyrosine, tryptophan, aspartate, glutamate, asparagine, glutamine, cysteine, and methionine; wherein the amino acid at position 27 is independently selected from the group consisting of lysine, glycine, alanine, valine, leucine, isoleucine, proline, serine, threonine, phenylalanine, tyrosine, tryptophan, aspartate, glutamate, asparagine, glutamine, cysteine, and methionine; wherein the amino acid at position 30 is independently selected from the group consisting of tyrosine, serine, lysine, arginine, histidine, aspartate, glutamate, asparagine, glutamine, and cysteine; wherein the amino acid at position 50 is independently selected from the group consisting of glutamic acid, lysine, arginine, histidine, glycine, and alanine; wherein the amino acid at position 59 is independently selected from the group consisting of tryptophan, serine, lysine, arginine, histidine, aspartate, glutamate, asparagine, glutamine, and cysteine; and wherein the amino acid at position 60 is independently selected from the group consisting of valine, serine, lysine, arginine, histidine, aspartate, glutamate, asparagine, glutamine, and cysteine. Such MDC polypeptide analogs are specifically contemplated to modulate the binding characteristics of MDC to chemokine receptors and/or other molecules (e.g., heparin, glycosaminoglycans, erythrocyte chemokine receptors) that are considered to be important in presenting MDC to its receptor. In one preferred embodiment, MDC polypeptide analogs of the invention comprise amino acids 1 to 69 of SEQ ID NO: 25.

The following additional analogs have been synthesized and also are intended as aspects of the invention: (a) a polypeptide comprising a sequence of amino acids identified by positions 1 to 70 of SEQ ID NO: 30; (b) a polypeptide comprising a sequence of amino acids identified by positions 9 to 69 of SEQ ID NO: 2; (c) a polypeptide comprising a sequence of amino acids identified by positions 1 to 69 of SEQ ID NO: 31; and (d) a polypeptide comprising a sequence of amino acids identified by positions 1 to 69 of SEQ ID NO: 32.

As set forth in detail below, experimental data indicates that the addition of as few as one additional amino acid at the amino terminus of human mature MDC is sufficient to confer useful MDC inhibitory properties to the resultant analog. Thus, all amino terminal addition analogs are contemplated as an aspect of the invention. Such addition analogs include the addition of one or a few randomly selected amino acids; the addition of common tag sequences (e.g., polyhistidine sequences, hemagglutinin sequences, or other sequences commonly used to facilitate purification); and chemical additions to the amino terminus (e.g., the addition of an amino terminal aminooxypentane moiety). See Proudfoot et al., *J. Biol. Chem.,* 271:2599–2603 (1996); Simmons er al., *Science,* 276 (5310): 276–279 (1997).

Also as set forth in detail below, evidence exists that mature MDC is cleaved in vivo by a dipeptidyl amino peptidase, resulting in an MDC(3–69) form that exhibits at least some activities antagonistic to MDC. An additional aspect of the invention includes analogs wherein the proline at position 2 of a mature MDC (e.g., human, murine, and rat MDC) is deleted or changed to an amino acid other than proline. Such analogs are collectively referred to as "MDCΔ$Pro_2$ polypeptides." Those MDCΔ$Pro_2$ polypeptides that retain MDC biological activities are contemplated as useful in all indications wherein mature MDC is useful; and are expected to be less susceptible to activity-destroying depeptidyl amino peptidases that recognize and cleave the sequence $NH_2$-Xaa-Pro- (e.g., CD26). Those MDCΔ$Pro_2$ polypeptides that lack MDC biological activities are contemplated as being used as MDC inhibitors.

It will be appreciated that, while the foregoing analogs were often described with reference to human mature MDC, similar analogs of other vertebrate MDC's, especially mammalian MDC's, also are contemplated as aspects of the invention.

It also will be appreciated that it may be advantageous to express MDC or MDC analogs as fusions with immunoglobulin-sequences, human serum albumin sequences, or other sequences, or to perform other standard chemical modifications, for the purpose of extending the serum half-life of the MDC or MDC analog. See, e.g., Yeh et al., *Proc. Nat'l. Acad. Sci. U.S.A.,* 89(5): 1904–1908 (1992); Sambrook et al., supra. The definition of polypeptides of the invention is intended to encompass such modifications.

In related aspects, the invention provides purified and isolated polynucleotides encoding such MDC polypeptide analogs, which polynucleotides are useful for, e.g., recombinantly producing the MDC polypeptide analogs; plasmid and viral vectors incorporating such polynucleotides, and prokaryotic and eukaryotic host cells stably transformed with such DNAs or vectors.

In another aspect, the invention includes antibody substances (e.g., monoclonal and polyclonal antibodies, single chain antibodies, chimeric or humanized antibodies, antigen-binding fragments of antibodies, and the like) which are immunoreactive with MDC polypeptides and polypeptide analogs of the invention. Such antibodies are useful, e.g., for purifying polypeptides of the present invention, for quantitative measurement of endogenous MDC in a host, e.g., using well-known ELISA techniques, and for modulating binding of MDC to its receptor(s). The invention further includes hybridoma cell lines that produce antibody substances of the invention. Exemplary antibodies of the invention include monoclonal antibodies 252Y and 252Z, which are produced by hybridoma cell line 252Y and hybridoma cell line 252Z, respectively. The hybridoma cell lines are themselves aspects of the invention, and have been deposited with the American Type Culture Collection (ATCC Accession Nos. HB-12433 and HB-12434, respectively). Another exemplary antibody of the invention is monoclonal antibody 272D, which is produced by hybridoma cell line 272D (itself an aspect of the invention and deposited with the American Type Culture Collection (ATCC Accession No. HB-12498).

Recombinant MDC polypeptides and polypeptide analogs of the invention may be utilized in a like manner to antibodies in binding reactions, to identify cells expressing receptor(s) of MDC and in standard expression cloning techniques to isolate polynucleotides encoding the receptor(s). Such MDC polypeptides, MDC polypeptide analogs, and MDC receptor polypeptides are useful for modulation of MDC chemokine activity, and for identification of polypeptide and chemical (e.g., small molecule) MDC agonists and antagonists.

Additional aspects of the invention relate to pharmaceutical utilities of MDC polypeptides and polypeptide analogs of the invention. For example, MDC has been shown to modulate leukocyte chemotaxis. In particular, MDC has been shown to induce macrophage chemotaxis and to inhibit monocyte chemotaxis. Thus, in one aspect, the invention includes a method for modulating (e.g., up-regulating or down-regulating) leukocyte chemotaxis in a mammalian host comprising the step of administering to the mammalian host an MDC polypeptide or polypeptide analog of the invention, wherein the MDC polypeptide or MDC polypeptide analog modulates leukocyte chemotaxis in the host. In preferred methods, the leukocytes are monocytes and/or macrophages. For example, empirically determined quantities of MDC are administered (e.g., in a pharmaceutically acceptable carrier) to induce macrophage chemotaxis or to inhibit monocyte chemotaxis, whereas inhibitory MDC polypeptide analogs are employed to achieve the opposite effect.

In another aspect, the invention provides a method for palliating an inflammatory or other pathological condition in a patient, the condition characterized by at least one of (i) monocyte chemotaxis toward a site of inflammation in said patient or (ii) fibroblast cell proliferation, the method comprising the step of administering to the patient a therapeutically effective amount of MDC. In one embodiment, a therapeutically effective amount of MDC is an amount capable of inhibiting monocyte chemotaxis. In another embodiment, a therapeutically effective amount of MDC is an amount capable of inhibiting fibroblast cell proliferation. Such therapeutically effective amounts are empirically determined using art-recognized dose-response assays.

As an additional aspect, the invention provides a pharmaceutical composition comprising an MDC polypeptide or polypeptide analog of the invention in a pharmaceutically acceptable carrier. Similarly, the invention relates to the use of a composition according to the invention for the treatment of disease states, e.g., inflammatory disease states. In one embodiment, the inflammatory disease state is characterized by monocyte chemotaxis toward a site of inflammation in a patient having the disease state. In another embodiment, the disease state is characterized by fibroblast cell proliferation in a patient having the disease state.

MDC induced chemotaxis of natural killer cells (NK) can lead to enhanced cytotoxicity of targeted NK cells against various forms of cancers. These forms of cancers include all solid tumor and cancerous cells found in various organs and skin (e.g., breast, ovarian, prostate, kidney, lung, pancreas, liver and bone cancers). NK cells also play an important role in antibody-dependent cell-mediated cytotoxicity. Stimulation of this process with MDC or MDC agonists would lead to improved immune response to tumors. [See generally *Immunology* (Ed. Kuby, J.) pp 304–6, W.H. Freeman and Co., New York, N.Y. (1992)]. Similarly, NK cells lead to viral immunity. MDC may be used to potentiate resistance to common viral diseases (e.g., influenza and rhinoviruses) by stimulating NK conferred viral immunity by stimulating antigen-specific $T_H$ memory cells. [*Immunology* Ed. Kuby J. pp 420–425, W.H. Freeman and Co. New York N.Y. (1992)]. "Treatment" as used herein includes both prophylactic and therapeutic treatment.

The apparent optimal concentration of mature MDC in receptor binding and chemotaxis experiments is about 10 ng/ml. Thus, for therapeutic methods involving the systemic administration of MDC (or MDC analogs retaining a desired MDC biological activity), doses and dosing schedules are preferably selected to maintain circulating concentrations in blood of about 0.1–10 ng/ml. Preferred approaches for preparing a dose and maintaining such levels in the bloods include administration of MDC in a bolus fashion, so as to administer approximately 0.1–10 mg of MDC. This administration is repeated in order to maintain the stated blood concentration. For example, MDC is stable at 1 mg/ml in phosphate-buffered saline (PBS) and is administered to experimental animals using this formulation. This formulation, either liquid or lyophilized and reconstituted, is suitable for human parenteral use, e.g., via intravenous injection. Other formulations can be devised to concentrate the protein drug and stabilize it for use years after its preparation. [See, e.g., *Stability and Characterization of Protein and Peptide Drugs; Case Histories*, Wang Y J and Pearlman R. (Eds.), Plenum Press, New York (1993) (describing methods for the preparation of cytokines and other similar protein drug formulations by the inclusion of a variety of excipients to maintain solubility and stability and minimize aggregation)]. Exemplary excipients include citrate, EDTA, detergents of the Tween family, zwittergent family, or pluronic family, and amino acids such as cysteine to maintain the proper oxidoreductant state.

In a second preferred approach, MDC is administered using any of a number of drug delivery methods that are known in the art to facilitate slow-release of the bioactive product. This can be accomplished as easily as employing intramusculature administration [see for example M. Groves in *Parental Technology Manual*, Second edition, M. J. Groves (Ed.), Interpharm Press, Inc., Prairie View, Ill., pp. 6–7 (1988)] to cause the MDC to be adsorbed into the blood stream over a delayed period of time. Alternatively, the MDC product can be delivered using a number of drug delivery methods [see for a general review LM Sanders, in *Peptide and Protein Drug Delivery*, V. H. L. Lee (Ed.), Marcel Dekker, Inc., New York, pp. 785–806 (1991)]. For example, MDC is incorporated into biodegradable microspheres, such as poly(lactic-co-glycolic acid of PLGA) microspheres as shown using Human Growth Hormone, [Tracy, *Biotechnol. Progress,* 14: 108–115 (1988)], or leuprolide acetate microspheres [Okada et al., *Pharm. Res,* 8: 787–791 (1991)] which can permit administrations as infrequently as once monthly. A variety of other drug delivery approaches will be apparent to those in the art, including dry powder formulations suitable for inhalation made available by Inhale Corporation, Palo Alto, Calif., and transdermal delivery made available by Alza Corporation, Palo Alto, Calif.

It will also be apparent from the teachings herein relating to the various activities of MDC that modulators of MDC activities, to inhibit the effects of endogenously-produced MDC and/or to promote the activities of endogenously-produced or exogenously administered MDC, have therapeutic utility. Such modulators typically include small molecules, peptides, chemokine fragments and analogs, and/or antibody substances. MDC inhibitors interfere with MDC signal transduction, e.g., by binding MDC molecules, by competitively or non-competitively binding MDC receptors on target cells, and/or by interfering with signal transduction in the target cells downstream from the chemokine receptors. Thus, in another aspect, the invention provides assays to screen putative chemokine modulators for modulating activity. Modulators identified by methods of the invention also are considered aspects of the invention.

In one embodiment, the invention provides a method for identifying a chemical compound having MDC modulating activity comprising the steps of: (a) providing first and second receptor compositions comprising MDC receptors; (b) providing a control composition comprising detectably-labeled MDC; (c) providing a test composition comprising detectably-labeled MDC and further comprising the chemical compound; (d) contacting the first receptor composition with the control composition under conditions wherein MDC is capable of binding to MDC receptors; (e) contacting the second receptor composition with the test composition under conditions wherein MDC is capable of binding to MDC receptors; (f) washing the first and second receptor compositions to remove detectably-labeled MDC that is unbound to MDC receptors; (g) measuring detectably-labeled MDC in the first and second receptor compositions; and (h) identifying a chemical compound having MDC modulating activity, wherein MDC modulating activity is correlated with a difference in detectably-labeled MDC between the first second receptor compositions.

As reported herein, the chemokine receptor CCR4 has been demonstrated to be a high affinity receptor for MDC. Thus, in a preferred embodiment of the foregoing method, the first and second receptor compositions comprise the MDC receptor that is CCR4. Since CCR4 is a membrane protein, a preferred embodiment for practicing the method is one wherein the first and second receptor compositions comprise CCR4-containing cell membranes derived from cells that express CCR4 on their surface. The cell membranes may be on intact cells, or may constitute an isolated fraction of cells that express CCR4. Cells that naturally express CCR4 and cells that have been transformed or transfected to express CCR4 recombinantly are contemplated. In an alternative embodiment, cells (e.g., eosinophils) that express an MDC receptor other than CCR4 are used to provide the composition comprising MDC receptors.

In a related aspect, the invention provides a method for identifying a modulator of binding between MDC and CCR4, comprising the steps of: (a) contacting MDC and CCR4 both in the presence of, and in the absence of, a putative modulator compound; (b) detecting binding between MDC and CCR4; and (c) identifying a putative modulator compound in view of decreased or increased binding between MDC and CCR4 in the presence of the putative modulator, as compared to binding in the absence of the putative modulator. The contacting is performed, for example, by combining MDC with cell membranes that contain CCR4, in a buffered aqueous suspension.

In one embodiment, the method is performed with labeled MDC. In step (b), binding between MDC and CCR4 is detected by detecting labeled MDC bound to CCR4. In a preferred embodiment, the contacting step comprises contacting a suspension of cell membranes comprising CCR4 with a solution containing MDC. In a highly preferred embodiment, the method further comprises the steps of recovering the cell membranes from the suspension after the contacting step (e.g., via filtration of the suspension); and washing the cell membranes prior to the detecting step to remove unbound MDC.

In an alternative embodiment, the method is performed with a host cell expressing CCR4 on its surface. In step (b), binding between MDC and CCR4 is detected by measuring the conversion of GTP to GDP in the host cell.

In yet another alternative embodiment, the method is performed with a host cell that expresses CCR4 on its surface, and binding between MDC and CCR4 expressed in the host cell is detected by measuring cAMP levels in the host cell.

It will be appreciated that assays for modulators such as those described above are often performed by immobilizing (e.g., on a solid support) one of the binding partners (e.g., MDC or a fragment thereof that is capable of binding CCR4, or CCR4 or a fragment thereof that is capable of binding MDC). In a preferred variation, the non-immobilized binding partner is labeled with a detectable agent. The immobilized binding partner is contacted with the labeled binding partner in the presence and in the absence of a putative modulator compound capable of specifically reacting with MDC or CCR4; binding between the immobilized binding partner and the labeled binding partner is detected; and modulating compounds are identified as those compounds that affect binding between the immobilized binding partner and the labeled binding partner.

In yet another embodiment, the invention provides a method for identifying a chemical compound having MDC modulating activity, comprising the steps of (a) providing first and second receptor compositions comprising MDC receptors; (b) contacting the first receptor composition with a control composition comprising detectably-labeled MDC; (c) contacting the second receptor composition with a test composition comprising detectably-labeled MDC and further comprising the chemical compound; (d) washing the first and second receptor compositions to remove detectably-labeled MDC that is unbound to MDC receptors; (e) measuring detectably-labeled MDC in the first and second receptor compositions after the washing; and (f) identifying a chemical compound having MDC modulating activity, wherein MDC modulating activity is correlated with a difference in detectably-labeled MDC between the first and the second receptor compositions.

In yet another embodiment, MDC binding to its receptor is measured by measurement of the activation of a reporter gene that has been coupled to the receptor using procedures that have been reported in the art for other receptors. See, e.g., Himmler et al., *Journal of Receptor Research*, 13:79–94 (1993).

MDC-binding fragments of high affinity receptors of MDC are specifically contemplated as inhibitor compounds of the invention; antibodies to such receptors also are contemplated as inhibitor compounds of the invention.

As taught herein in detail, MDC stimulates eosinophil chemotaxis through a pathway that apparently does not involve the chemokine receptor CCR4. This discovery provides for the design of assays to identify modulators of MDC activity that have specificity for CCR4-mediated activities without affecting MDC-induced stimulation of eosinophils, and vice versa.

For example, in one embodiment, the invention provides a method for identifying a modulator of binding between MDC and eosinophils, comprising the steps of: (a) contacting MDC and a composition comprising an MDC receptor that is expressed on eosinophil cell membranes in the presence and in the absence of a putative modulator compound; (b) detecting binding between MDC and the composition; and (c) identifying a putative modulator compound in view of decreased or increased binding between MDC and the composition in the presence of the putative modulator, as compared to binding in the absence of the putative modulator.

To identify modulators with eosinophil-specificity, the method, in a preferred embodiment, further comprising the steps of: (d) contacting MDC and a composition comprising CCR4 in the presence and in the absence of the putative modulator compound; (e) detecting binding between MDC and CCR4; (f) identifying a putative modulator compound in view of decreased or increased binding between MDC and CCR4 in the presence of the putative modulator, as compared to binding in the absence of the putative modulator; and (g) selecting a modulator identified in step (c) as causing increased or decreased binding and identified in step (f) as failing to cause increased or decreased binding. To identify modulators with specificity towards CCR4, in step (g) one selects a modulator identified in step (f) as causing increased or decreased binding and identified in step (c) as failing to cause increased or decreased binding.

MDC's involvement in various aspects of immune responses is described in detail below. Based on the involvement of MDC in immune response, the administration of MDC antagonists is indicated, for example, in the treatment of anaphylaxis [Brown, A. F., *J. Accid. Emerg. Med.*, 12(2): 89–100 (1995)], shock [Brown (1995) supra], ischemia, reperfusion injury and central ischemia [Lindsberg et al., *Ann. Neurol.*, 30(2):117–129 (1991)], atherogenesis [Handley et al., *Drug Dev. Res.*, 7:361–375 (1986)], Crohn's disease [Denizot et al., *Digestive Diseases and Sciences*, 37(3):432–437 (1992)], ischemic bowel necrosis/necrotizing enterocolitis [Denizot et al. (1992), supra, and Caplan et al., *Acta Pediat. Suppl.*, 396:11–17 (1994)], ulcerative colitis (Denziot et al. (1992), supra), ischemic stroke [Satoh et al., *Stroke*, 23:1090–1092 (1992)], ischemic brain injury [Lindsberg et al., *Stroke*, 21:1452–1457 (1990) and Lindsberg et al. (1991), supra], systemic lupus erythematosus [Matsuzaki et al., *Clinica Chimica Acta*, 210:139–144 (1992)], acute pancreatitis [Kald et al., *Pancreas*, 8(4):440–442 (1993)], septicemia (Kald et al. (1993), supra), acute post-streptococcal glomerulonephritis [Mezzano et al., *J. Am. Soc. Nephrol.*, 4:235–242 (1993)], pulmonary edema resulting from IL-2 therapy [Rabinovichi et al., *J. Clin. Invest.*, 89:1669–1673 (1992)], ischemic renal failure [Grino et al., *Annals of Internal Medicine*, 121(5):345–347 (1994)]; pre-term labor [Hoffman et al., *Am. J. Obstet. Gynecol.*, 162(2):525–528 (1990) and Maki et al., *Proc. Natl. Acad. Sci. USA*, 85:728–732 (1988)], adult respiratory distress syndrome [Rabinovichi et al., *J. Appl. Phsiol.*, 74(4):1791–1802 (1993); Matsumoto et al., *Clin. Exp. Pharmocol. Physiol.*, 19:509–515 (1992); and Rodriguez-Roisin et al., *J. Clin. Invest.*, 93:188–194 (1994)]. "Treatment" as used herein includes both prophylactic and therapeutic treatment.

MDC acts as a chemoattractant for $T_H2$ differentiated memory cells, which produce the cytokines IL-4, IL-5, IL-10 and others. It is expected that, in some instances, MDC leads to an immune state in which $T_H1$ cytokine driven responses are reduced. In such instances, antagonism of MDC would lead to a state in which $T_H1$ cytokine driven responses are enhanced. Modulation of the $T_H1$–$T_H2$ balance may lead to enhanced "immune surveillance," and improved eradication of viral and parasitic infections. Administration of MDC antagonists of the invention to mammalian subjects, especially humans, for the purposes of ameliorating pathological conditions associated with undesirable or excessive $T_H2$ responses and/or less-than-desirable $T_H1$ responses are contemplated as additional aspects of the invention. Administration of sufficient MDC antagonists to substantially reduce endogenous IL-10, a $T_H1$ immune suppressing cytokine, would lead to enhanced cytotoxic T-lymphocyte mediated immunity and immune surveillance [see Muller et al., *J. Infect. Dis.*, 177: 586–94 (1998); Kenney et al., *J. Infect. Dis.*, 177: 815–9 (1998)]. In these situations an effective dose and dosing schedule can be determined by monitoring circulating IL-10 levels and increasing the dose and frequency of administration to reduce IL10 levels to near normal levels. Treatment of chronic or persistent viral infections and parasitic infections is specifically contemplated, especially in combination with other antiviral or anti-parasitic infection therapeutics. Similarly, treatment or prevention of graft failure or graft rejection with MDC antagonists is contemplated. The administration of MDC antagonists is indicated, for example, in Leishmaniasis [Li et al., *Infect. Immunol.*, 64:5248–5254 (1996); Krishnan et al., *J. Immunol.*, 156(2):653–62 (1996)], opportunistic lung infections in cystic fibrosis patients [Moser et al., *APMIS*, 105(11):838–42 (1997)], to delay HIV-1 induced immunodeficiency [Berger et al., *Res. Virol.*, 147(2–3): 103–108 (1996); Barker et al., *Proc. Natl. Acad. Sci. USA*, 92(24):11135–9 (1995); Jason et al., *J. Acquir. Immune. Defic. Syndrome Retrovirol.*, 10(4): 471–6 (1995); Maggi et al., *J. Biol. Regul. Homeost. Agents*, 9(3): 78–81 (1995)], chronic interstitial lung disease [Kunkel et al., *Sarcoidosis Vasc. Diffuse Lung Dis.*, 13: 120–128 (1996)], in neurological disorders associated with a $T_H2$ response [Windhagen et al., *Chem. Immunol.*, 63: 171–86 (1996); Bai et al., *Clin. Immunol. Immunopathol.*, 83(2): 117–26 (1997)], colorectal cancer [Pellegrini et al., *Cancer Immunol. Immunother.*, 42(1): 1–8 (1996)], viral infection, for example various species of herpes and hepatitis [Spruance et al., *Antiviral Res.*, 28(1): 39–55 (1995); Pope et al., *J. Immunol.*, 156(9): 3342–9 (1996); Bartoletti et al., *Gastroenterol.*, 112(1): 193–199 (1997)], candidiasis and other fungal infections [Spaccapelo et al., *J. Immunol.*, 155(3): 1349–60 (1995); Fidel et al., *J. Infect. Dis.*, 176(3): 728–39 (1995); Cenci et al., *J. Infect Dis.*, 171(5): 1279–88 (1995)], chronic pneumonia [Johansen et al., *Behring Inst. Mitt.*, 98: 269–73 (1997)], solid tumor cancer [Khar et al., *Cytokines Mol. Ther.*, 2(1): 39–46 (1996)], Bordella pertussis respiratory infection [Ryan et al., *J. Infect Dis.*, 175(5): 1246–50 (1997)], systemic lupus erythrematosus [Segal et al., *J. Immunol.*, 158(6): 2648–53 (1997)], Bullous pemphigoid pathogenesis [Deptia et al., *Arch Dermatol Res.*, 289(12): 667–70 (1997)], glomerulonephritis [Kitching et al., *Kidney Int.*, 53(1): 112–8 (1998); Huang et al., *J. Am Soc. Neprol.*, 8(7): 1101–8 (1997); Tipping et al., *Eur. J. Immunol.*, 27(2): 515–21 (1997)], pulmonary respiratory syncytial virus infection [Hussell et al., *Eur. J. Immunol*, 27(12): 3341–9 (1997)], complications of trauma associated with surgical stress [Decker et al., *Surgery*, 119(3): 316–25 (1996)], celiac disease [Karban et al., *Isr. J. Med. Sci.,* 33(3): 209–14 (1997)], Gulf War syndrome [Rook et al., *Lancet,* 349 (9068): 1831–3 (1997)], ameobocyte infection, for example *Plasmodium falciparum* [Elghazali et al., *Clin. Exp. Immunol.,* 109(1): 84–9 (1997)] and *schistosoma mansoni* [Wolowczuk et al., *Immunol.,* 91(1): 35–44 (1997)], and B-cell lymphoma, especially mucosa-associated lymphoid tissue type [Greiner et al., *Am J. Pathol.,* 150(5): 1583–93 (1997)]. "Treatment" as used herein includes both prophylactic and therapeutic treatment.

In fact, the expression pattern of MDC (or TARC) and its receptor CCR4 provide a unique indication for MDC in vivo in inducing a cellular complex (e.g., dendritic and/or macrophage cells, $T_H2$ antigen-specific memory cells, and antigen-specific B cells) geared to producing a strong humoral immune response. The induced complex is contemplated to produce antigen-specific antibodies and $T_H2$-specific cytokines (IL-2, IL-4, IL-5, and/or IL-10) and additional chemokines, including additional MDC, with local concentrations of the chemokines and cytokines that potentiate the activity of the complex possibly being quite high. The cellular complex is specifically contemplated to be involved in the establishment of a humoral response to "recall antigens," since another chemokine/receptor pair (MIP3α/CCR6) appears to be specific for "naive" responses to new antigens. Thus, administration of MDC or MDC agonists for the purpose of inducing or augmenting a response to "recall antigens" is specifically contemplated as an aspect of the intention. Similarly, administration of MDC antagonists is indicated when suppression of such an immune response is desired. Administration of MDC antagonists to treat conditions and disorders mediated (directly or indirectly) by $T_H2$ cell migration, including but not limited to autoimmune conditions, lupus erythematosus, multiple sclerosis, scleroderma, asthma, and atopic allergy, is specifically contemplated.

With respect to any of the conditions, disorders, and disease states identified in the preceding paragraphs, an exemplary method of treatment comprises the steps of identifying a human subject in need of therapeutic or prophylactic treatment for one of the above-identified conditions, disorders, or disease states; and administering to the human subject a therapeutically or prophylactically effective amount of an MDC antagonist compound. By "therapeutically effective amount" is meant a dose and dosing schedule that is sufficient to cure the disease state, or to reduce the symptoms or severity of the disease state. By "prophylactically effective amount" is meant a dose and dosing schedule that is sufficient to reduce the likelihood of occurrence of a disease state, or delay its onset, relative to human subjects that are considered to have equivalent risk of developing the disease state but whom are not treated with an MDC antagonist. Therapeutically effective amounts are readily determined by dose-response studies that are conventionally performed in the art.

In one highly preferred embodiment, the invention includes a method of inhibiting proliferation of a mammalian immunodeficiency virus comprising the step of contacting mammalian cells that are infected with a mammalian immunodeficiency virus with a composition comprising an MDC-UV antagonist compound or TARC-IV antagonist compound, in an amount effective to inhibit proliferation of said virus in said cells. The family of mammalian immunodeficiency viruses is intended to include human immunodeficiency viruses, such as strains of HIV-1 and HIV-2, and analogous viruses known to infect other mammalian species, including but not limited to simian and feline immunodeficiency viruses. The method can be performed in vitro (e.g., in cell culture), but preferably is performed in vivo by administering the antagonist to an infected subject, e.g., an HIV-infected human subject. (In yet another embodiment, the method is performed prophylactically developing an HIV infection, e.g., due to the subject's likelihood of exposure to contaminated blood samples, contaminated needles, or intimate exposure to an HIV-infected person.)

The term "MDC-IV antagonist compound" refers to compounds that antagonize the apparent Immunodeficiency Virus-proliferative effects of MDC in infected cells. Thus, the term "MDC-IV antagonist compound" is meant to include any compound that is capable of inhibiting proliferation of the immunodeficiency virus in a manner analogous to either the inhibition reported herein for MDC neutralizing antibodies or the inhibition reported herein for certain MDC analogs (e.g., analogs having amino terminal additions or truncations). For example, anti-MDC antibodies are highly preferred MDC-IV antagonist compounds. For treatment of humans infected with an HIV virus, humanized antibodies are highly preferred. Similarly, polypeptides that comprise an antigen-binding fragment of an anti-MDC antibody and that are capable of binding to MDC are preferred MDC-IV antagonist compounds.

As described elsewhere herein in greater detail, amino-terminal truncations of mature human MDC(1–69) possess antiproliferative activity against HIV-1. Thus, another set of preferred MDC-IV antagonist compounds are polypeptides whose amino acid sequence consists of a portion of the amino acid sequence set forth in SEQ ID NO: 2 sufficient to bind to the chemokine receptor CCR4, said portion having an amino-terminus between residues 3 and 12 of SEQ ID NO: 2 (i.e., analogs lacking at least three amino acids from the amino terminus of MDC(1–69). Amino terminal deletion analogs that have been further modified, e.g., by including an oligopeptide tag to facilitate purification, or by including an initiator methionine for bacterial expression, are also contemplated.

Amino-terminal additions to mature MDC also result in analogs possessing antiproliferative activity against HIV-1. Thus, another set of preferred MDC-IV antagonist compounds are polypeptides that comprise a mature MDC sequence (e.g., amino acids 1–69 of SEQ ID NO: 1), and that further comprise a chemical addition to the amino terminus of the mature MDC sequence to render said polypeptide antagonistic to MDC. Additions of additional amino acids and other chemical moieties are contemplated.

It will further be appreciated that substitution of amino acids in a mature MDC sequence (especially substitutions in the amino terminus of mature MDC) may be expected, in some instances, to result in analogs possessing antiproliferative activity against HIV-1. Such analogs also are intended MDC-IV antagonist compounds, and are identifiable using HIV proliferation assays described herein.

It is postulated that MDC's HIV-proliferative effects are mediated, at least in part, through the chemokine receptor CCR4. Thus, the family of MDC-IV antagonist compounds includes polypeptides that comprise the C—C chemokine receptor 4 (CCR4) amino acid sequence set forth in SEQ ID NO: 34 or that comprise a continuous fragment thereof that is capable of binding to MDC or TARC. Such polypeptides are expected to bind endogenous MDC and thereby inhibit HIV proliferation in a manner analogous to anti-MDC antibodies. Also contemplated are anti-CCR4 antibodies, which are expected to block MDC-CCR4 interactions, thereby inhibiting MDC-induced HIV proliferation.

As described herein in detail, the chemokine TARC possesses sequence similarity to MDC, possesses various overlapping biological activities, and, like MDC, binds to the chemokine receptor CCR4. These similarities suggest that compounds that inhibit TARC-CCR4 interactions will also be useful for inhibiting proliferation of immunodeficiency viruses. Compounds that inhibit TARC-induced proliferation of such viruses are collectively referred to as "TARC-IV antagonist compounds." Such compounds include anti-CCR4 antibodies, anti-TARC antibodies (especially humanized versions); and polypeptides that are capable of binding to TARC and that comprise an antigen-binding fragment of an anti-TARC antibody.

It is also contemplated that modifications to the amino terminus of mature TARC polypeptides will result in TARC-IV antagonist compounds, in a manner analogous to what has been reported herein for MDC analogs. Thus, TARC-IV antagonist compounds for use in methods of the invention include polypeptides that have an amino acid sequence consisting of a portion of the amino acid sequence set forth in SEQ ID NO: 43 that is sufficient to bind to the chemokine receptor CCR4, said portion having an amino-terminus between residues 1 and 10 of SEQ ID NO: 43. Polypeptide comprising mature TARC sequences, and further comprising chemical additions to the amino terminus to render the polypeptide antagonistic to TARC also are contemplated. Polypeptides comprising the mature TARC amino acid sequence, into which substitutions have been introduced to confer HIV antiproliferative activity, also are contemplated as TARC-IV antagonist compounds.

In another highly preferred embodiment, the invention includes a method of inhibiting platelet aggregation in a mammalian subject (especially a human subject) comprising the step of administering to a mammalian subject a composition comprising an MDC-PA antagonist compound or TARC-PA antagonist compound, in an amount effective to inhibit platelet aggregation in the subject. Such methods may be performed for therapeutic purposes, e.g., in patients suffering from undesirable blood clotting, or for prophylactic purposes on a subject at risk of developing undesirable blood clotting or coagulation. Such patients would include, e.g., patients who have previously suffered myocardial infarction or stroke or other clotting disorders, or who are deemed to be at high risk for developing such conditions.

The term "MDC-PA antagonist compound" refers to compounds that antagonize the apparent Platelet Aggregating effects of MDC. Thus, the term "MDC-PA antagonist compound" is meant to include any compound that is capable of inhibiting platelet aggregation that is observable after administration of MDC to a mammalian subject (e.g., to a mouse or rat). Those compounds described above as MDC-IV antagonist compounds are specifically contemplated as MDC-PA antagonist compounds as well. For example, anti-MDC antibodies are highly preferred MDC-PA antagonist compounds. For treatment of humans, humanized antibodies are highly preferred. Similarly, polypeptides that comprise an antigen-binding fragment of an anti-MDC antibody and that are capable of binding to MDC are preferred MDC-PA antagonist compounds. All MDC analogs that inhibit the platelet aggregating effects of MDC also are preferred. Analogs having additions, deletions, and/or substitutions in the amino terminus are specifically contemplated.

The structural and functional similarities between MDC and TARC reported herein indicate that compounds that inhibit TARC-CCR4 interactions will be useful for inhibiting platelet aggregation. Compounds that inhibit TARC-induced platelet aggregation are collectively referred to as "TARC-PA antagonist compounds." Such compounds include anti-CCR4 antibodies, anti-TARC antibodies (especially humanized versions); various TARC analogs described elsewhere herein, and polypeptides that are capable of binding to TARC and that comprise an antigen-binding fragment of an anti-TARC antibody.

As described herein in detail, the expression patterns of MDC and its receptor, CCR4, provide an indication for the use of MDC as an adjuvant in a vaccine. Thus, in another aspect, the invention includes a vaccine composition comprising an antigen of interest in a suitable pharmaceutical carrier, improved by the inclusion of MDC in the vaccine composition. The antigen of interest may be any composition intended to generate a desirable immune response in a human or other animal. Such compositions would include, for example, killed or attenuated pathogens or antigenic portions thereof. In a related aspect, the invention includes a method of immunizing a human or animal, wherein the improvement comprises administering MDC to the human or animal, either concurrently or before or after administering an antigen of interest. As explained above, MDC is contemplated to preferentially augment an immune response to "recall antigens." Accordingly, in a preferred embodiment, MDC is included in a booster vaccine composition.

For any of the therapeutic indications and methods described above, another aspect of the invention relates to the use of indicated compounds (e.g., MDC, MDC fragments or analogs, MDC agonists, or MDC antagonists) for preparation of a medicament for the therapeutic indication. For example, the invention includes the use of an MDC antagonist for preparation of a medicament for suppressing a humoral response to recall antigens.

The foregoing aspects and numerous additional aspects will be apparent from the drawing and detailed description which follow.

BRIEF DESCRIPTION OF THE DRAWING

FIG. 1 is a comparison of the amino acid sequence of human MDC (SEQ ID NO: 2) with the amino acid sequences of other, previously characterized human C—C chemokines: MCP-3 [Van Damme et al., *J. Exp. Med.,* 176:59 (1992)] (SEQ ID NO: 18); MCP-1 [Matsushima et al., *J. Exp. Med.,* 169:1485 (1989)] (SEQ ID NO: 19); MCP-2 (mature form) [Van Damme et al., supra; Chang et al., *Int. Immunol.,* 1:388 (1989)] (SEQ ID NO: 20); RANTES [Schall et al., *J. Immunol.,* 141:1018 (1988)] (SEQ ID NO: 21); MIP-1β [Brown et al., *J. Immunol.,* 142:679 (1989)] (SEQ ID NO: 22); MIP-1α [Nakao et al., *Mol. Cell Biol,* 10:3646 (1990)] (SEQ ID NO: 23); and I-309 [Miller et al., *J. Immunol.,* 143:2907 (1989)] (SEQ ID NO: 24). A slash "/" marks the site at which putative signal peptides are cleaved. Dashes are inserted to optimize alignment of the sequences.

FIG. 2 is a graph depicting the chemotactic effect (measured in fluorescence units) of increasing concentrations of MDC on human mononuclear cell migration in a chemotaxis assay. Closed circles show the response of human mononuclear cells derived from the cell line THP-1. The open diamond shows the response to the positive control, zymosan activated serum (ZAS).

FIG. 3 is a graph depicting the chemotactic effect (measured in fluorescence units) of increasing concentrations of MDC on human polymorphonuclear (pmn) leukocyte migration. Closed circles show response to MDC, and an open diamond shows the response to the positive control, IL-8.

FIG. 4 is a graph depicting the chemotactic effect (measured in fluorescence units) of increasing concentrations of MDC on macrophage and monocyte migration. Closed circles show the response to MDC of macrophages derived from the cell line THP-1. Open circles show the response to MDC of monocytes derived from the cell line THP-1.

FIG. 5 is a graph depicting the chemotactic effect (measured in fluorescence units) of increasing concentrations of MDC on guinea pig peritoneal macrophage migration. Closed circles show the response of macrophages to MDC. An open triangle shows the response to the positive control, zymosan activated serum (ZAS).

FIG. 6 is a graph depicting the chemotactic-inhibitory effect (measured in fluorescence units) of increasing concentrations of MDC on THP-1 monocyte migration induced by MCP-1. Closed circles depict the chemotactic-inhibitory effects of MDC where chemotaxis has been induced by MCP-1. Open circles depict the chemotactic-inhibitory effects of MDC in a control experiment wherein only the basal medium (RPMI with 0.2% BSA (RBSA), no MCP-1) was employed. The zero point on the x axis corresponds to the response of cells to MCP-1 and RBSA in the absence of any MDC.

FIG. 7 is a graph depicting the effect (measured in counts per minute (cpm)) of increasing concentrations of MDC on fibroblast proliferation. Closed circles depict the proliferative response with purified MDC that was recombinantly produced in CHO cells (Example 10F). Open circles depict the response with chemically synthesized MDC (Example 11).

FIG. 8 schematically depicts the construction of mammalian expression vector pDC1.

FIG. 9 depicts the nucleotide and deduced amino acid sequence (SEQ ID NOs: 39 and 40) of a S. cerevisiae alpha factor pre-pro/human MDC cDNA chimeric construct used to express human MDC in yeast.

DETAILED DESCRIPTION

Figure 2:
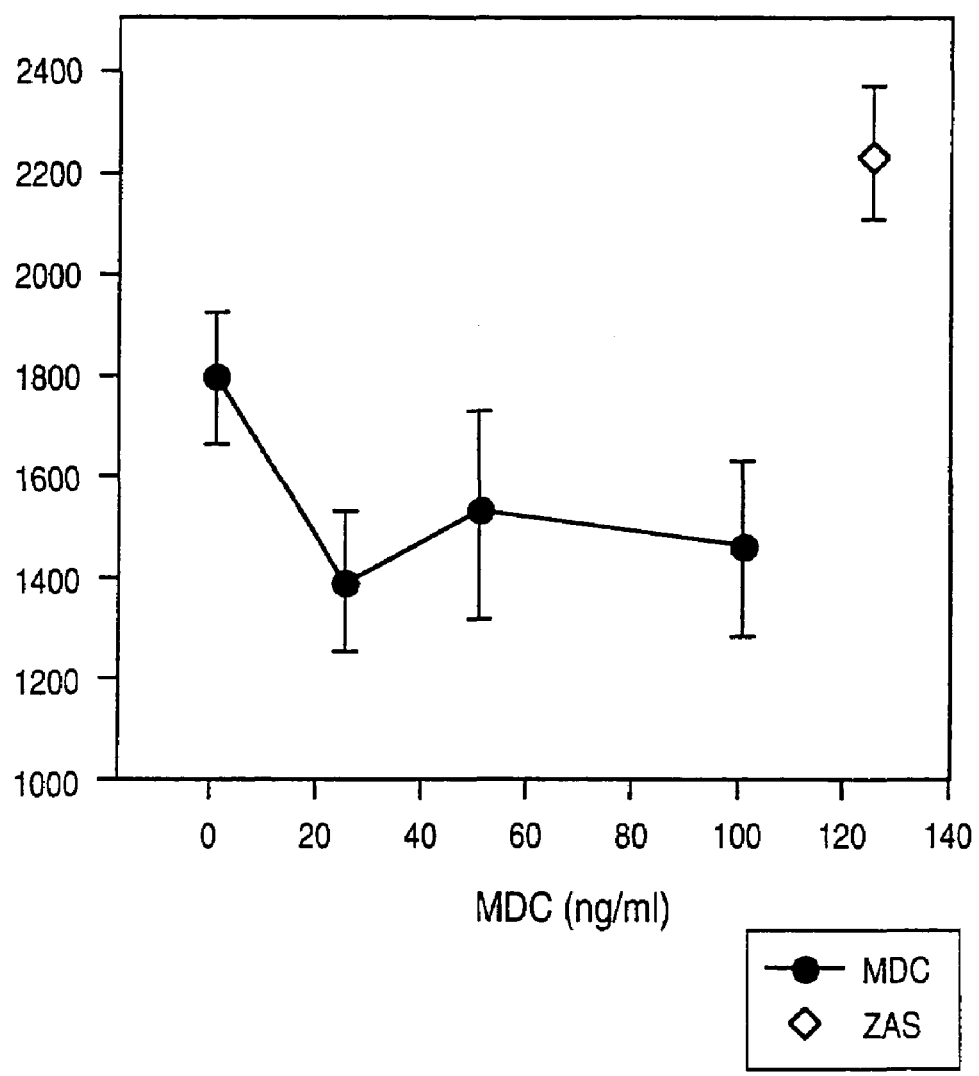

The present invention is illustrated by the following examples related to a human cDNA, designated MDC cDNA, encoding a novel C—C chemokine designated MDC (for "macrophage-derived chemokine"). More particularly, Example 1 describes the isolation of a partial MDC cDNA from a human macrophage cDNA library. Example 2 describes the isolation of additional cDNAs from the cDNA library using the cDNA from Example 1 as a probe, one of these additional cDNAs containing the entire MDC coding sequence. Additionally, Example 2 presents a composite MDC cDNA nucleotide sequence and presents a characterization of the deduced amino acid sequence of the chemokine (MDC) encoded thereby. In Example 3, experiments are described which reveal the level of MDC gene expression in various human tissues. The greatest MDC gene expression was observed in the thymus, with much weaker expression detectable in spleen and lung tissues. Example 4 describes more particularly the expression of the MDC gene during monocyte maturation into macrophages and during inducement of HL60 cell differentiation to a macrophage-like cell type.

Since MDC gene expression was detected in thymus and spleen in Example 3, in situ hybridization studies were conducted to localize further the MDC gene expression in these tissues. Moreover, in situ hybridization revealed a correlation between elevated MDC gene expression in inflamed tissues, as exemplified using intestinal tissue from Crohn's diseased patients. These in situ hybridization experiments are described in Example 5.

Example 6 describes the recombinant production of MDC as a GST fusion protein in prokaryotic cells, as well as the cleavage of the fusion protein and purification of the recombinant MDC. Example 7 describes alternative DNA constructs useful for expression of recombinant MDC protein, and describes the production of MDC by a bacterial host transformed with such a construct.

Example 8 provides experimental protocols for purification of recombinant MDC produced, e.g., as described in Example 7. Examples 9 and 10 provide protocols for the recombinant production of MDC in yeast and mammalian cells, respectively. In addition, Example 10 provides additional protocols for purification of recombinant MDC, and describes the determination of the amino terminus of MDC recombinantly produced in mammalian cells. Example 11 describes production of MDC and MDC polypeptide analogs by peptide synthesis. Certain preferred analogs are specifically described in Example 11.

Examples 12–17 provide protocols for the determination of MDC biological activities. For instance, Example 12 provides an assay of MDC effects upon basophils, mast cells, and eosinophils. MDC-induced chemotaxis of eosinophils is specifically demonstrated. Example 13 describes assays of chemoattractant and cell-activation properties of MDC on monocytes/macrophages, neutrophils, and granulocytes. MDC induced macrophage chemotaxis, but inhibited monocyte chemotaxis.

Examples 14–17 provide protocols for the determination of MDC biological activities in vivo. Example 14 provides an MDC tumor growth-inhibition assay. Examples 15 and 16 provide protocols for assaying MDC activity via intraperitoneal and subcutaneous injection, respectively. Example 17 provides protocols for determining the myelosuppressive activity of MDC.

Example 18 provides protocols for generating antibodies that are specifically immunoreactive with MDC, including polyclonal, monoclonal, and humanized antibodies. Uses of the antibodies also are described.

Example 19 provides a calcium flux assay for determining the ability of MDC to induce cellular activation.

Example 20 provides assays and experimental results relating to the HIV proliferative and anti-proliferative effects of human mature MDC and MDC antagonists.

Example 21 demonstrates the anti-proliferative effects of MDC on fibroblasts. Example 22 provides in vitro assays for the effects of MDC upon the proliferation of additional cell types. Example 23 provides an in vivo assay for determining the anti-proliferative effects of MDC on fibroblasts.

Example 24 describes the chromosomal localization of the human MDC gene.

Example 25 describes procedures which identified the CC chemokine receptor "CCR4" as a high affinity binding partner of MDC. Examples 26 and 27 provide assays for identifying MDC modulators.

Example 28 describes the isolation of cDNAs encoding rat, mouse, and macaque MDC, and characterizes the MDC proteins encoded thereby. Example 29 further characterizes selected MDC analogs.

Example 30 describes experiments that demonstrate that anti-MDC monoclonal antibodies are effective for neutralizing biological activities of MDC that were elucidated in other examples.

Example 31 describes experiments that demonstrate that MDC induces chemotaxis of $T_H2$ helper cells, a discovery with therapeutic implications as discussed in Example 31 and elsewhere herein.

Example 32 describes platelet-aggregating activities of MDC, and describes the use of MDC and MDC antagonists to modulate platelet aggregation.

Example 33 provides exemplary assays to demonstrate the therapeutic efficacy of an MDC antagonist to modulate immune responses in a mammalian host.

EXAMPLE 1

Isolation of a cDNA Encoding MDC

A partial cDNA for a new C—C chemokine, designated pMP390, was isolated from a macrophage cDNA library as described in U.S. patent application Ser. No. 08/939,107, filed Sep. 26, 1997, and in related international publication number WO 96/40923, both of which are incorporated herein by reference. Sequence comparisons were performed on Dec. 14, 1994, by the BLAST Network Service of the National Center for Biotechnology Information (e-mail: "blast@ncbi.nlm.nih.gov"), using the alignment algorithm of Altschul et al., *J. Mol. Biol.*, 215: 403–410 (1990). The sequence analysis revealed that a portion of the isolated macrophage cDNA clone designated pMP390 contained a gene sequence having approximately 60–70% identity with previously-identified chemokine genes, including the human MCP-3 gene and rat MIP-1β gene.

The 2.85 kb cDNA insert of pMP390 was subcloned into the vector pBluescript SK⁻ (Stratagene, La Jolla Calif.) to facilitate complete sequencing. The complete sequence of this pMP390 cDNA corresponds to nucleotides 73 to 2923 of SEQ ID NO: 1 (and to deduced amino acids −6 to 69 of SEQ ID NO 2). The sequence that was originally compared to database sequences corresponds to nucleotides 73 to 610 of SEQ ID NO: 1.

EXAMPLE 2

Isolation of Additional cDNA Clones Having the Complete MDC Coding Sequence

Using the pMP390 cDNA clone isolated in Example 1, additional cDNA clones were isolated from the same human macrophage cDNA library, these additional cDNAs containing additional 5' sequence and encoding the complete amino acid sequence of a macrophage derived chemokine. The additional cloning and sequencing is described in detail in U.S. Ser. No. 08/939,107 and WO 96/40923, incorporated herein by reference.

Of the additional clones, clones designated pMP390-12 and pMP390B contained the largest additional 5' coding sequence, each extending an additional 72 nucleotides upstream of the sequence previously obtained from the cDNA clone pMP390. A composite DNA sequence, herein designated MDC cDNA, was generated by alignment of the pMP390 and pMP390-12 cDNA sequences. This 2923 base pair composite cDNA sequence, and the deduced amino acid sequence of the chemokine MDC, are set forth in SEQ ID NOs: 1 and 2, respectively.

Manual comparison of the deduced MDC amino acid sequence with sequences of known chemokines indicates that the MDC cDNA sequence encodes a novel C—C chemokine ninety-three amino acids in length, sharing 28–34% amino acid identity with other C—C chemokines (FIG. 1). As aligned in FIG. 1, MDC shares 29% amino acid identity with MCP-1 and MIP-1α, 28% identity with MCP-2, 32% identity with I-309, 33% identity with MCP-3 and MIP-1β, and 34% identity with RANTES. Importantly, the four cysteine residues characteristic of the chemokines are conserved in MDC. Five additional residues also are completely conserved in the eight sequences presented in FIG. 1.

The first 24 amino acids of the 93 amino acid MDC sequence are predominantly hydrophobic and are consistent with von Heijne's rules [*Nucleic Acids Res.*, 14: 4683–90 (1986)] governing signal cleavage. These features and the polypeptide comparison in FIG. 1 collectively suggest that the MDC cDNA encodes a twenty-four amino acid signal peptide that is cleaved to produce a mature form of MDC beginning with the glycine residue at position 1 of SEQ ID NO: 2. This prediction was confirmed by direct sequencing of MDC protein produced recombinantly in mammalian cells, as described below in Example 10. The MDC composite cDNA sequence shown in SEQ ID NO: 1 extends nineteen nucleotides upstream of the predicted initiating methionine codon, and 2.6 kb downstream of the termination codon.

EXAMPLE 3

Determination of MDC Gene Expression in Human Tissues

Northern blot analyses were conducted to determine the tissues in which the MDC gene is expressed.

A radiolabeled pMP390 5' fragment which corresponds to the region of the MDC cDNA encoding the putative mature form of MDC plus 163 bases of the adjacent 3' noncoding region was used to probe Multiple Tissue Northern blots (Clontech, Palo Alto, Calif.) containing RNA from various normal human tissues. The probe was denatured by boiling prior to use, and the hybridizations were conducted according to the manufacturer's specifications. Autoradiographs were exposed 5 days at −80° C. with 2 intensifying screens.

The greatest MDC gene expression was observed in the thymus, with much weaker expression detectable in spleen and lung tissues. Expression of MDC in tissue from the small intestine was at even lower levels, and no expression was detected in brain, colon, heart, kidney, liver, ovary, pancreas, placenta, prostate, skeletal muscle, testis, or peripheral blood leukocytes.

As discussed in detail below in Example 25, MDC is a ligand for the CC chemokine receptor CCR4, which receptor also has been reported to be a ligand for the chemokine TARC. See Imai et al., *J. Biol. Chem.*, 272: 15036–15042 (1997). Like MDC, TARC is abundantly expressed in the thymus, with little expression observed in other tissues. More particularly, CCR4 is expressed on T cells, especially CD4⁺ T cells [See Imai et al. (1997), and Power et al., *J. Biol. Chem.*, 270: 19495–19500 (1995)], while MDC and TARC are expressed by cells of the dendritic lineage which form a major component of the thymic architecture. See Godiska et al., *J. Exp. Med.*, 185: 1595–1604 (1997), incorporated herein by reference; and Imai et al., *J. Biol.*

*Chem.*, 271: 21514–21521 (1996). These expression patterns suggest a biological activity of MDC, CCR4, and TARC in T cell development, since immature progenitor cells undergo differentiation and expansion (leading to the establishment of the major T cell lineages and the elimination of potentially autoreactive T cells) within the highly specialized microenvironment of the thymus. See von Boehmer, *Current Biology*, 7: 308–310 (1997). The fact that MDC also is expressed at high levels in cultured macrophages suggests an MDC activity in the initiation and/or triggering of the immune response, by facilitating the interaction of T cells with antigen-presenting cells at sites of inflammation.

These expression pattern data suggest therapeutic utilities of MDC (or MDC mimetics or agonists) to stimulate beneficial immune responses. For example, MDC, MDC agonists, or MDC mimetics may be administered to augment/enhance T cell activation where T cell activation may be beneficial. The use of MDC as an adjuvant in vaccine development or in tumor immunotherapy is specifically contemplated.

Conversely, the expression pattern data also indicates a therapeutic utility for modulators of MDC's interaction with CCR4 in T cell-mediated autoimmune diseases, including but not limited to psoriasis, graft versus host disease, and allograft rejection, and in T cell and/or B cell mediated allergic responses.

EXAMPLE 4

MDC Gene Expression During Macrophage Maturation

Because the cDNAs encoding MDC were isolated from a human macrophage cDNA library, MDC gene expression during differentiation of monocytes into macrophages was examined.

A

Human monocytes from a single donor were cultured on a series of tissue culture plates, and cells from one plate were harvested after 0, 2, 4 or 6 days. See generally Elstad et al., *J. Immunol.* 140:1618–1624; Tjoelker et al., *Nature*, 374: 549–552 (1995). Under these conditions, the monocytes differentiated into macrophages by days 4–6 [Stafforini et al., *J. Biol. Chem.*, 265: 9682–9687 (1990)].

A Northern blot of RNA (10 μg per lane) isolated from the cells harvested at each time point was prepared and probed, using a radiolabeled pMP390 fragment. No signal was detectable in RNA from freshly isolated monocytes, whereas a very strong signal was generated from cells that had differentiated into macrophages after six days of culture. Cells cultured for four days produced a much weaker signal, whereas the signal generated from cells cultured for two days could be seen only after prolonged exposure of the filter.

B

To confirm the expression of MDC in differentiated human macrophages, culture supernatants were analyzed by western blotting with anti-MDC monoclonal antibodies produced as described below in Example 18. Several plates of human macrophages were differentiated by growth on plastic for eight days in the presence of macrophage colony stimulating factor (0.5 ng/ml, R&D Systems, Minneapolis, Minn.).

The medium from the differentiated macrophage cell cultures was removed and replaced with similar medium or with medium containing low density lipoprotein (LDL, Sigma), oxidized LDL (oxidized by incubation in 5 μM $CuSO_4.5H_2O$ according to the method of Malden et al., *J. Biol. Chem.*, 266:13901 (1991)), or dexamethazone (6 nM, Sigma Chemical Co.). Following 3 days of each treatment, the culture medium was removed, brought to pH 6.8 by the addition of HCl, and passed over a Heparin-Sepharose CL-6B column (Pharmacia, Piscataway, N.J.). The column was washed with 0.2 M NaCl in 20 mM Tris, pH 8, and eluted with 0.6 M NaCl in 20 mM Tris, pH 8. The eluted material was fractionated on an 18% acrylamide SDS-PAGE gel (NOVEX) and electroblotted to PVDF membrane (Millipore, Bedford Mass.). The filter was blocked, washed, and reacted with monoclonal antibodies against MDC using standard techniques (Sambrook et al.). In each of the culture media analyzed, MDC protein was detected at a concentration of approximately 0.5 μg/ml, thus confirming expression of MDC in differentiated human macrophages.

Expression of MDC also was analyzed in human epithelial cell lines. The colon epithelial cell line T84 (ATCC #CCL-248) was grown in DMEM/F12 medium (GIBCO, Gaithersburg Md.), and the lung epithelial cell line A549 (ATCC #CCL-185) was grown in F12 medium. Screening for the presence of MDC mRNA in the cells and MDC protein in the culture medium was performed as described above for macrophages. No evidence of MDC expression was detectable by either method in these cell lines.

In addition, samples of the T84 cell line were treated for 1 day with TNFα (5 ng/ml, PeproTech, Rocky Hill, N.J.), TGF-β (1 ng/ml, R&D Systems), or interferon-γ (200 U/ml, PeproTech), each with or without addition of recombinant MDC at 100 ng/ml (derived from CHO cell transfectants; see Ex. 10). Samples of the A549 cell line were treated with 50 ng/ml PMA (Sigma Chemical Co.) for 0, 1, 3, 5, or 7 days. None of these treatments resulted in detectable expression of MDC mRNA in the T84 or A549 cells when screened by Northern blotting as described above.

C

Further examination of MDC gene expression in macrophages was conducted by treating the human cell line HL60 with either 1% DMSO (Sigma Chemical Co.) or 50 ng/ml PMA (Sigma). Treatment with DMSO induces differentiation of HL60 cells into a granulocytic cell type, whereas PMA induces their differentiation into a macrophage lineage [Perussia et al., *Blood*, 58: 836–843 (1981)]. RNA was isolated from untreated cells and from cells treated for one or three days with DMSO or PMA, electrophoresed (10 μg/lane), and blotted. The Northern blot of the RNA was probed with the radiolabeled pMP390 5' fragment described in Example 3.

After three days of PMA treatment, the HL-60 cells clearly expressed MDC mRNA, although the level of expression was apparently less than that of macrophages after six days of culture (see above). No expression was seen after one day of treatment or in untreated cells. Further, no detectable expression of MDC was induced by treatment with DMSO for one or three days.

EXAMPLE 5

In Situ Hybridization

Because MDC gene expression was detected in the thymus and spleen, in situ hybridization was carried out to localize the source of the message in these tissues. Further, in situ hybridization was used to correlate MDC gene expression with tissue inflammation, using intestinal tissue from Crohn's disease patients as an example. The procedures used for these experiments are described in detail in U.S. Ser. No. 08/939,107 and WO 96/40923, both of which are incorporated by reference.

Observed hybridization of the anti-sense strand indicated that the MDC gene was expressed in cells throughout the cortex of normal human thymus, with weak signal in the follicles. Expression of MDC in the thymus may indicate a T lymphocyte developmental role of MDC. Expression in normal human spleen was localized to cells of the red pulp, whereas little signal was detected in the white pulp. A high level of expression in inflamed tonsil was localized to the epithelial region, although inflammatory cells appeared to have infiltrated the entire tissue sample.

Colon samples from patients with Crohn's disease exhibited hybridization in cells of the epithelium, lamina propria, Payer's patches, and smooth muscle. In contrast, normal human colon showed no hybridization above background. The observed pattern of MDC expression in the colons of Crohn's disease patients closely correlates with the expression of a macrophage-specific gene, Platelet Activating Factor Acetylhydrolase (PAF-AH) [Tjoelker et al., supra]. This result, together with the data presented in Example 4, suggest that macrophages express MDC cDNA in vivo during pathogenic inflammation. Moreover, the identification of MDC in Crohn's disease colon tissue samples suggest diagnostic relevance of MDC levels (e.g., in a patient's blood, stool sample, and/or intestinal lesions) to a patient's disease state or clinical prognosis.

EXAMPLE 6

Production of Recombinant MDC

To produce recombinant MDC protein, the sequence encoding the putative mature form of the protein was amplified by PCR and cloned into the vector pGEX-3X (Pharmacia, Piscataway, N.J.). The pGEX vector is designed to produce a fusion protein comprising glutathione-S-transferase (GST), encoded by the vector, and a protein encoded by a DNA fragment inserted into the vector's cloning site.

An MDC cDNA fragment was amplified by PCR using the primers 390-2R (SEQ ID NO: 8) and 390-FX2 (SEQ ID NO: 11). Primer 390-FX2 contains a BamH I restriction site, followed by a sequence encoding a thrombin cleavage site [Chang et al., Eur. J. Biochem., 151:217 (1985)] followed by bases 92–115 of SEQ ID NO: 1. The thrombin cleavage site is as follows: leucine-valine-proline-arginine-glycine-proline, in which glycine and proline are the first two residues of the mature form of MDC. Treatment of the recombinant fusion protein with thrombin is expected to cleave the arginine-glycine bond of the fusion protein, releasing the mature chemokine from the GST fusion.

The PCR product was purified by agarose gel electrophoresis, digested with BamH I endonuclease, and cloned into the BamH I site of pGEX-3X. This pGEX-3X/MDC construct was transformed into E. coli XL-1 Blue cells (Stratagene, La Jolla Calif.), and individual transformants were isolated and grown. Plasmid DNA from individual transformants was purified and partially sequenced using an automated sequencer and primer GEX5 (SEQ ID NO: 12), which hybridizes to the pGEX-3X vector near the BamHI cloning site. The sequence obtained with this primer confirmed the presence of the desired MDC insert in the proper orientation.

Induction of the GST-MDC fusion protein was achieved by growing the transformed XL-1 Blue culture at 37° C. in LB medium (supplemented with carbenicillin) to an optical density at wavelength 600 nm of 0.4, followed by further incubation for 4 hours in the presence of 0.25 to 1.0 mM Isopropyl β-D-Thiogalactopyranoside (Sigma Chemical Co., St. Louis Mo.).

The fusion protein, produced as an insoluble inclusion body in the bacteria, was purified as follows. Cells were harvested by centrifugation; washed in 0.15 M NaCl, 10 mM Tris, pH 8, 1 mM EDTA; and treated with 0.1 mg/ml lysozyme (Sigma Chemical Co.) for 15 minutes at room temperature. The lysate was cleared by sonication, and cell debris was pelleted by centrifugation for 10 minutes at 12,000×g. The fusion protein-containing pellet was resuspended in 50 mM Tris, pH 8, and 10 mM EDTA, layered over 50% glycerol, and centrifuged for 30 min. at 6000×g. The pellet was resuspended in standard phosphate buffered saline solution (PBS) free of $Mg^{++}$ and $Ca^{++}$. The fusion protein, which remained insoluble, was approximately 80–90% of the protein mass and migrated in denaturing SDS-polyacrylamide gels with a relative molecular weight of 33 kD. The protein yield, as judged by Coomassie staining, was approximately 100 mg/l of E. coli culture.

The fusion protein was subjected to thrombin digestion to cleave the GST from the mature MDC protein. The digestion reaction (20–40 ug fusion protein, 20–30 units human thrombin (4000 U/mg (Sigma) in 0.5 ml PBS) was incubated 16–48 hrs. at room temperature and loaded on a denaturing SDS-PAGE gel to fractionate the reaction products. The gel was soaked in 0.4 M KCl to visualize the GST and MDC protein bands, which migrated as fragments of approximately 26 kD and 7 kD, respectively.

The identity of the 7 kD SDS-PAGE fragment was confirmed by partial amino acid sequence analysis. First, the protein was excised from the gel, electroeluted in 25 mM Tris base and 20 mM glycine, and collected onto a PVDF membrane in a ProSpin column (Applied Biosystems, Foster City, Calif.). Subjecting the sample to automated sequencing (Applied Biosystems Model 473A, Foster City, Calif.) yielded 15 residues of sequence information, which corresponded exactly to the expected N-terminus of the predicted mature form of MDC (SEQ ID NO: 2, amino acid residues 1 to 15).

EXAMPLE 7

Production of Recombinant MDC in Bacteria

MDC peptides and analogs can be expressed using a variety of bacterial expression systems including E. coli, Bacillus subtilis, streptomyces lividans, and many others. [For a general review see "Gene Expression Technology" in Methods in Enzymology, Vol. 185: pp. 1–283, Ed. D. V. Goeddel, Academic Press, San Diego, Calif. (1990).] In general, an expression cassette comprised of a transcription element (a promoter), a translation element, a coding region to be expressed (for example MDC), and a transcription termination element is developed and optimized to effect significant gene expression. This cassette is incorporated into either episomal plasmids, which confer stable propagation, or into integration vectors to mediate the insertion or creation (via homologous recombination) of an expression cassette within the host genome. The gene can be expressed directly or can be fused to signal sequences (e.g., pelB, ompA, est2) to direct secretion of the gene product out of the cytoplasm into either the periplasmic space or media, or to other leader sequences (e.g., ubiquitin) to enhance the folding or otherwise stabilize the recombinantly expressed coding region. The gene product, either properly folded or not, can be recovered in a crude state or as inclusion bodies from the cells following a fermentation phase and either directly purified or refolded prior to purification.

A. Construction and Testing of Bacterial MDC Expression Vector P2-390

The portion of the MDC cDNA encoding the predicted mature MDC protein was cloned into a plasmid containing the arabinose promoter (araB) and the pelB leader sequence [see Better et al., *Science*, 240:1041–43 (1988)].

More particularly, an MDC cDNA was amplified by PCR using approximately 0.1 μg of pMP390-12 as template and synthetic oligonucleotide primers 390-2R (SEQ ID NO:8) and 390-Pel (SEQ ID NO: 13). Primer 390-Pel contains an Nco I restriction site, followed by two cytosine residues, followed by bases 92 to 115 of SEQ ID NO: 1.

The expected PCR product of 232 bp was purified by agarose gel electrophoresis, digested with Nco I and BamH I, and cloned along with a portion of the arabinose operon and pelB leader sequence (Better et al., supra) into the vector pUC19 (New England Biolabs, Beverly, Mass.). The resultant construct, designated P2-390, encodes a fusion of the pelB leader (encoded by the vector) to the mature MDC protein. The sequence of this construct was confirmed by automated sequencing using the primers Ara1 (SEQ ID NO:28) and Ara2 (SEQ ID NO:29), which anneal to the vector adjacent to the cloning site. The plasmid P2-390 was transformed into the *E. coli* strain MC1061 using standard procedures, and an ampicillin resistant clone was selected for MDC production. The clone was grown in a 3 liter fermenter (Applikon, Foster City, Calif.) and MDC production was induced by the addition of 50% arabinose to a final concentration of 0.1%. After one day of cultivation in the presence of arabinose, the cells were harvested. Western blotting revealed that MDC was present within the cells at a level of approximately 4 μg/g of cell paste and was secreted into the culture medium to a level of approximately 1 μg/ml.

B. Protocol for Bacterial Expression of MDC Using Plasmid P2-390

The plasmid P2-390 was transformed into *E. coli* strain SB7219 (Sheppard and Englesberg, *J. Molec. Biol.*, 25:443–454 (1967) and Wilcox et al., *J. Biol. Chem.*, 249:2946–2952 (1974)). SB7219 is a prototrophic strain incapable of degrading arabinose, the inducer of the araB promoter used to transcribe the pelB-MDC coding region. The genotype of SB7219 is *E. coli* K12 F⁻ del(codb-lac)3 del(ara735) rpsL150 (str$^R$) λ⁻. The production strain SB7219:P2-390 was grown in the fermenter (run FC563) in a fed batch format. A frozen aliquot of the seed is inoculated into 250 ml of fermentation basal medium in the shake flask. The composition of the basal medium is as follows:

| Basal Medium | |
|---|---|
| Component | Quantity per L |
| Na₃citrate | 1 g |
| 5.4% FeCl₃.6H₂O | 2 ml |
| glucose | 2 g |
| NaH₂PO₄.H₂O | 3 g |
| K₂HPO₄ | 6 g |
| (NH₄)₂SO₄ | 5 g |
| 20% yeast extract solution | 5 ml |
| 1 M CaCl₂ | 0.5 ml |
| 1 M MgCl₂ | 2.0 ml |
| trace elements | 4 ml |
| trace vitamins | 2 ml |
| 1% thiamine | 1 ml |
| tetracycline | 5 mg |
| pH is set to | 7.0 |

| Trace Elements Solution | |
|---|---|
| Component | Quantity per L |
| Boric Acid | 5.0 g |
| Copper Sulfate.5H₂O | 2.0 g |
| Potassium Iodide | 1.0 g |
| Manganese sulfate | 10 g |
| Molybdic acid | 0.5 g |
| ZnCl₂ (Anhydrous) | 5.2 g |
| Cobalt chloride | 0.5 g |

| Trace Vitamin Solution | |
|---|---|
| Component | Quantity per L |
| Sodium Hydroxide, 50% | 1.3 ml |
| Riboflavin | 0.42 g |
| Folic Acid | 0.04 g |
| D-Pantothenic Acid (hemicalcium salt) | 5.4 g |
| Nicotinic Acid (niacin) | 6.1 g |
| Pyridoxine HCl | 1.4 g |
| Biotin | 0.06 g |

The shake flask culture is grown at 37° C. and 220 RPM to an optical density corresponding to mid-exponential growth (approximately OD$_{600}$≈0.7). The inoculum is added to the fermentor containing 1.5 L of basal media and grown at 30° C. for 5 hours. A feed is then initiated at 3.6 ml/hr and exponentially increased to effect a doubling time of 5 hr until a maximum of 18 ml/hr of feed is achieved.

| Feed Medium | |
|---|---|
| Component | Quantity per L |
| Na₃citrate | 5 g |
| 5.4% FeCl₃.6H₂O | 10 ml |
| glycerol | 500 g |
| (NH₄)₂SO₄ | 5 g |
| 1 M CaCl₂ | 4 ml |
| 1 M MgCl₂ | 100 ml |
| 1 M MnCl₂ | 0.4 ml |
| trace elements | 10 ml |

When the wet cell mass is approximately 100 g/L, 20 ml of 50% arabinose solution is added to induce expression of MDC. The temperature is raised to 37° C. and the feed rate is decreased to 12 ml/hr. The fermentation is allowed to continue for approximately 20 more hours, at which time the cell paste is harvested from the tank and stored frozen at −70° C. The MDC contained in the cell paste is suitable for recovery by mechanical lysis, re-folding, and purification as described below in Example 8.

C. Direct Expression of MDC in *E. coli*

In a similar way, MDC that is directly expressed (i.e., without a fused in-frame leader sequence) is engineered into the same vector. The plasmid pBAR5/MDC/RC is a plasmid identical to P2-390 except for the elimination of the pelB leader sequence. In addition, the first fourteen percent of the MDC(1–69) coding sequence (amino acid codons 1–6 and 8–10) have been modified to change cytosine residues at codon position three to either an adenosine or thymidine nucleotide (while preserving the encoded amino acid). Additionally, a translation initiation codon was added. Thus, the coding sequence in pBAR5/MDC/RC begins:

5' ATG GGA CCA TAT GGA GCA AAT ATG GAA GAT AGT . . . (SEQ ID NO: 44)

*E. coli* strain SB7219 harboring this plasmid is grown in a fermentor essentially as described above and the MDC that is produced is similarly recovered.

D. P2-390 Variant Expression Vector

In addition, a derivative of P2-390 pBAR5/PelB/MDC/RC in which the amino acid codons described above in part C were substituted for the wild-type sequence was created. *E. coli* SB7219 harboring this plasmid is grown in a fermentor in a comparable fashion and the MDC produced is similarly recovered.

EXAMPLE 8

Purification of Recombinant MDC from Bacteria and Culture Medium

The following are experimental protocols for purification of the recombinant MDC produced as described in Example 7.

A. Recovery and Purification of Secreted Recombinant MDC.

The secreted recombinant MDC protein is purified from the bacterial culture media by, e.g., adapting methods previously described for the purification of recombinantly produced RANTES chemokine [Kuna et al., *J. Immunol.*, 149:636–642 (1992)], MGSA chemokine [Horuk et al., *J. Biol. Chem.* 268:54146 (1993)], and IP-10 chemokine (expressed in insect cells) [Sarris et al., *J. Exp. Med.*, 178: 1127–1132 (1993)].

B. Recovery and Re-folding of MDC Bound in Inclusion Bodies

Methods for recovery of inclusion bodies from *E. coli* paste has been well described [see Lin et al., *Biotechniques*, 11(6): 748–52 (1991); Myers et al., *Prot. Express. Purif.*, 2: 136–143 (1991); Krueger et al., *BioPharm.*, pp. 40–45 (March, 1989); Marston et al., "Solubilization of Protein Aggregates," *Methods in Enzymology*, M P Deutcher (Ed.), Academic Press, New York, 182: 264–276 (1990)]. Briefly, MDC is released from intact cells using a mechanical lysis device (e.g., Mauton-Gaulin). The cell paste is resuspended (20–30% w/v) in buffer [for example, containing 50 mM Tris HCl, pH 8.0, 1 mM EDTA, 50 mM NaCl, 0.2 mg/ml lysozyme, and 0.5% (v/v) Triton X-100] and passed through the machine at a constant pressure of 8–12,000 PSI for one to two passes at 4–15° C. The soluble components of the cell are separated from MDC and the other cellular-derived insoluble components by applying a centrifugal force of approximately 12,000×g for a period of about 5–10 minutes. The insoluble pelleted material is then re-suspended and re-centrifuged using dilute solutions of detergent [for example, 0.5% (v/v) Triton X-100 and 10 mM EDTA, pH 8.0]. Other wash steps can be used, including 0.5% (v/v) Zwittergent 3–14 (Calbiochem, Inc.), as well as treatments to minimize viscosity including lysozyme, DNase, Nonidet and EDTA [see Bartholome-DeBelder et al., *Mol. Microbiol.*, 2:519 (1988)].

To achieve proper folding of MDC contained in exclusion bodies, inclusion body preparations are reduced at a protein concentration of 5–10 mg/ml in 6 M guanidine.HCl containing 0.1M Tris HCl, pH 8.6, 20% β-mercaptoethanol, for 1 hour at 37° C. Complete reduction results in a completely clear solution. Confirmation of complete reduction is obtained using an analytical reverse phase (rp) HPLC procedure. For example, a Vydac C4 analytical column (e.g., 214 nm) is equilibrated in 5% acetonitrile/water/0.1% trifluoroacetic acid. The sample is injected and a linear gradient with increasing acetylnitrile content is run at a rate of 2% increase per minute. A single peak indicates that complete reduction of the MDC protein has been achieved.

The pH of the solution containing the fully reduced MDC is gradually lowered to 4.0 with 10% HCl. The MDC is then recovered from the reduction solution using preparative rpHPLC [e.g., a Vydak C4 preparative column with the gradient as described above] to remove HCl salts and denaturant. The recovered MDC is then diluted into 2 M guanidine.HCl, 0.1 M Tris HCl, pH 8.6, 8 mM cysteine, 1 mM cystine to a protein concentration of 2 g/L. The solution is stirred slowly at room temperature for 4–8 hours and shielded from light. The concentration of properly refolded MDC is monitored using the analytical rpHPLC method described above and is distinguished from reduced MDC by a 2–4 minute reduction in retention time on the HPLC column, relative to the reduced MDC. Confirmation of disulfide bond formation in refolded MDC is confirmed using mass spectrometry [i.e., MALDI MS].

C. Purification of Refolded MDC

MDC is purified using a two column procedure as follows: SP-Sepharose-fast flow (Pharmacia) resin is packed for column purification and equilibrated in loading buffer (0.2 M NaCl, 20 mM Tris base, pH 7.5). The recovered, refolded MDC solution is diluted with buffer until the conductivity of the supernatant equals 18–19 mS, and the pH is adjusted to 7.5. The solution is filtered to remove insoluble materials and applied to the column to a capacity of 0.5 mg MDC/ml of resin. Loading buffer is then used until the $OD_{280}$ returns to baseline. MDC is eluted using a higher salt buffer (0.6 M NaCl, 20 mM Tris, pH 7.5).

The SP-Sephadex elution peak is then chromatographed on an WP Hi-Propyl (C3) hydrophobic interaction column (JT Baker #7585-02). The column is equilibrated with 2.4 M NaCl, 20 mM Tris, pH 7.5. The 0.6 M NaCl containing S—P eluate is then adjusted with the appropriate amount of 5 M NaCl to bring the salt concentration of the eluate to 2.4M NaCl. The adjusted eluate is loaded onto the propyl column at 2 mg of MDC/ml and washed with 2.4 M NaCl 20 mM Tris, pH 7.5, until the $OD_{280}$ returns to baseline. The column is then washed with two column volumes of 2.0 M NaCl, 20 mM NaCl. The purified MDC is eluted from the column with 0.8 M NaCl 20 mM Tris, pH 7.5. Purified MDC is then filter sterilized and stored at −70° C.

EXAMPLE 9

Recombinant Production of MDC in Yeast

Following are protocols for the recombinant expression of MDC in yeast and for the purification of the recombinant MDC. Heterologous expression of human genes using microbial hosts can be an effective method to produce therapeutic proteins both for research and commercial manufacture. Secretion from yeast hosts (see recent review by Romanos, *Yeast,* 8: 423–488 (1992)) such as *Saccharomyces cerevisiae* (Price et al., *Gene,* 55:287 (1987)) *Kluyveromyces lactis* (Fleer et al., *Bio/Technology,* 9: 968–975 (1991)), *Pichia pastoris,* (Cregg et al., *Bio/Technology,* 11: 905–910 (1993)), *Schizosaccharomyces pombe* (Broker et al., *FEBS Lett.,* 248: 105–110 (1989)), and related organisms provide a particularly useful approach to obtain both high titer production of crude bulk product and rapid recovery and purification. These expression systems typically are comprised of an expression cassette containing a strong transcriptional segment of DNA or promoter to effect high levels of mRNA expression in the host. The mRNA typically encodes a coding region of interest preceded by an in-frame leader sequence, e.g., *S. cerevisiae* pre-pro alpha factor (Brake et al., *Proc. Nat Acad. Sci.,* 81: 4642–4646 (1984)) or equivalent signal, which directs the mature gene product to the culture medium. As taught below, MDC can be expressed in such a manner.

In one exemplary protocol, the coding region of the MDC cDNA is amplified from pMP390-12 by PCR, using as primers synthetic oligonucleotides containing the MDC cDNA sequences present in primers 390-1F (SEQ ID NO: 7) and 390-2R (SEQ ID NO: 8). A DNA encoding the yeast pre-pro-alpha leader sequence is amplified from yeast genomic DNA in a PCR reaction using one primer containing bases 1–20 of the alpha mating factor gene and another primer complimentary to bases 255–235 of this gene [Kujan and Herskowitz, *Cell,* 30: 933–943 (1982)]. The pre-pro-alpha leader coding sequence and MDC coding sequence fragments are ligated into a plasmid containing the yeast alcohol dehydrogenase (ADH2) promoter, such that the promoter directs expression of a fusion protein consisting of the pre-pro-alpha factor fused to the mature MDC polypeptide. As taught by Rose and Broach, *Meth. Enz.,* 185: 234–279, D. Goeddel ed., Academic Press, Inc., San Diego, Calif. (1990), the vector further includes an ADH2 transcription terminator downstream of the cloning site, the yeast "2-micron" replication origin, the yeast leu-2d gene, the yeast REP 1 and REP2 genes, the *E. coli* beta-lactamase gene, and an *E. coli* origin of replication. The beta-lactamase and leu-2d genes provide for selection in bacteria and yeast, respectively. The leu-2d gene also facilitates increased copy number of the plasmid in yeast to induce higher levels of expression. The REP1 and REP2 genes encode proteins involved in regulation of the plasmid copy number.

The DNA construct described in the preceding paragraph is transformed into yeast cells using a known method, e.g., lithium acetate treatment [Stearns et al., *Meth. Enz.,* supra, pp. 280–297]. The ADH2 promoter is induced upon exhaustion of glucose in the growth media [Price et al., *Gene,* 55:287 (1987)]. The pre-pro-alpha sequence effects secretion of the fusion protein from the cells. Concomitantly, the yeast KEX2 protein cleaves the pre-pro sequence from the mature MDC chemokine [Bitter et. al., *Proc. Natl. Acad. Sci. USA,* 81:5330–5334 (1984)].

Alternatively, MDC is recombinantly expressed in yeast using a commercially available expression system, e.g., the *Pichia* Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol.

The secreted MDC is purified from the yeast growth medium by, e.g., the methods used to purify MDC from bacterial and mammalian cell supernatants (see Examples 8 and 10).

Figure 10:
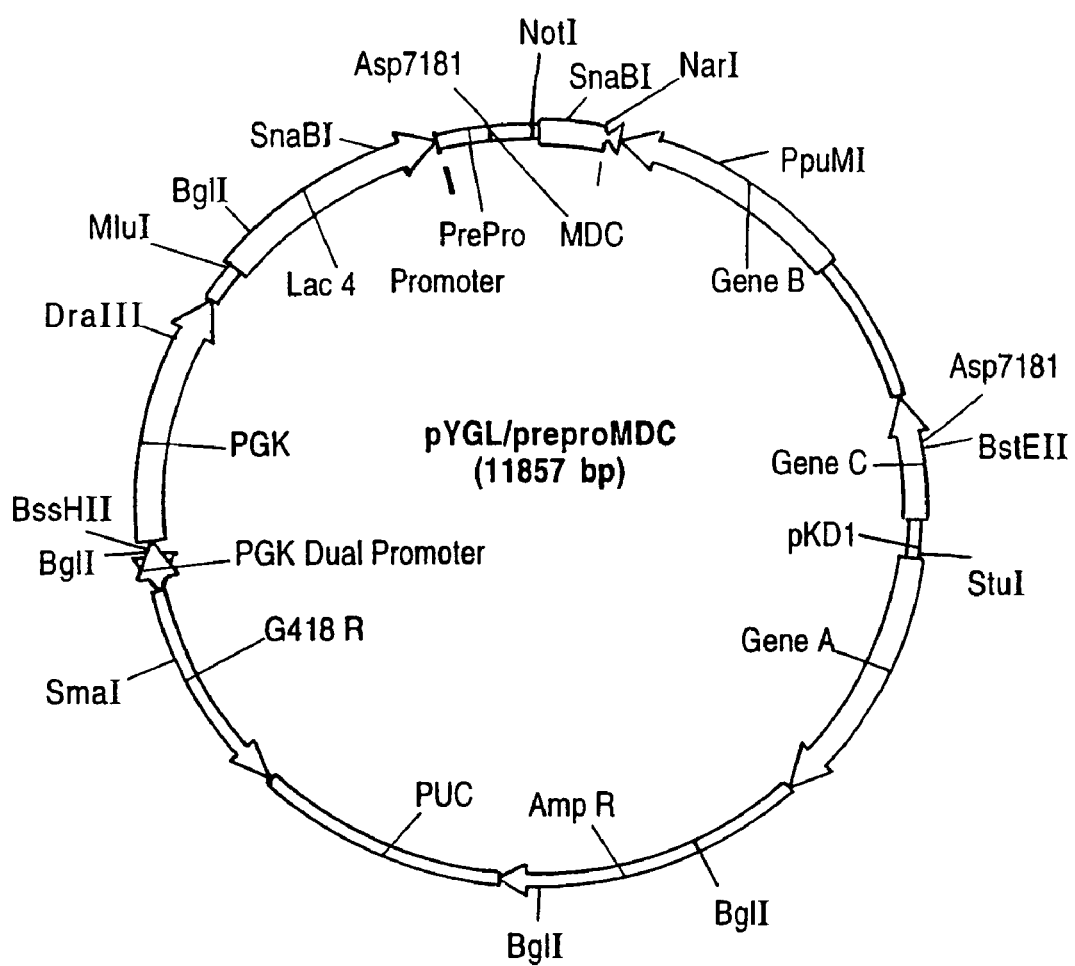
FIG. 10 depicts the structure of plasmid pYGL/pre-proMDC, used to express human MDC in yeast.

MDC was expressed in yeast as follows. Using standard molecular biological methods (Sambrook et al., *Molecular Cloning: a Laboratory Manual,* Second Edition, Cold Spring Harbor Laboratory Press, Cold Spring Harbor, N.Y. (1989)) such as those described above, the *S. cerevisiae* alpha factor pre-pro sequence (codons 1–85 in FIG. 9) was fused to the presumptive mature form of MDC (SEQ ID NO: 1, positions 1–69; codons 86–155 in FIG. 9). Expression of the resultant coding region is under control of the *K. lactis* LAC4 promoter present in the plasmid pYGL/preproMDC (see FIG. 10). This plasmid is a derivative of the *K. lactis* expression plasmid developed by Fleer et al., (supra) and used to secrete high titers of human serum albumin. This vector class is derived from the plasmid pKD1, a 2μ like plasmid from in *K. drosophilarium* (Chen et al., *Nucleic Acids Research,* 14: 447–81 (1986)). These vectors are autonomously replicated and maintained at high copy number and have been shown to confer high levels of protein production when *K. lactis* strains containing these plasmids are grown in either galactose or lactose as "inducing" agents and as the sole carbon source. The construct pYGL/preproMDC confers to the host both resistance to G418 (200 mg/L) and the glycolytic enzyme phosphoglucokinase (PGK). Efficient selection for transformed cells containing the plasmid is effected by providing a sole carbon source that requires processing via the glycolytic pathway of intermediary metabolism.

Plasmid pYGL/preproMDC was transformed into the pgko deficient host strain FBO5 (Delta Biotechnology Limited) by selecting for G418 resistance in YEPPglycerol/ethanol medium (0.5% yeast extract, 1% peptone, 1 M $KPO_4$, pH 7.0, containing 3% glycerol and 2% ethanol). Following clonal isolation, the transformed seed was grown in shake flask production medium YEPPgal (0.5% yeast extract, 1% peptone, 1 M $KPO_4$, pH 7.0, containing 2% galactose as sole carbon source). SDS-PAGE analysis of the culture medium indicated that a protein species of the molecular weight expected of that for mature MDC was present. This protein migrated comparably to synthetic MDC (Gryphon Sciences Corporation). Titration data using dilutions of purified synthetic MDC and culture supernatants in Coomassie blue stained SDS-PAGE gels suggested that MDC was present in the range of 4–10 mg/L.

Western analyses using an anti-MDC monoclonal antibody did not reveal the presence of MDC-related degradation products, even after further culturing of the seed 24 hours past the completion of growth. This observation suggested that the seed is capable of producing and stably accumulating MDC, indicating that high cell fermentation methods would be effective to increase titer.

The MDC production seed was used to inoculate a fermentor maintained at 26° C. containing a batch medium. The composition of the batch medium (1200 ml) was as follows: 7.5 g Yeast extract; 0.6 g $MgSO_4$; 6.0 g $NH_4SO_4$; 9.6 g $KH_2PO_4$; 26.4 g $K_2HPO_4$; 11 mg $CaCl_2$; 5.0 ml 1000×vitamins [Bitter et al., *J. Med. Virol.,* 25(2):123–140 (1988)]; 2.5 ml 1000×trace elements [Bitter et al. (1988)]; and 1.2 g 30% galactose.

One hour following inoculation, a feed was initiated at a rate of 12 ml/hour and maintained for four days. The feed medium composition (1500 ml) was as follows: Galactose, 600 g; yeast extract, 50 g; MgSO$_4$, 4 g; NH$_4$SO$_4$, 40 g; K$_2$HPO$_4$, 60 g; K$_2$HPO$_4$, 165 g; 1000×trace elements, 15 ml; 1000×vitamins, 30 ml; 4% CaCl$_2$ solution, 20 ml.

Samples were collected and analyzed throughout the run. MDC accumulated during the first three days of the fermentation to a final titer of approximately 50 mg/L as determined from purification recovery experiments. The primary protein species present is MDC. Significant levels of degradation were not observed by SDS-PAGE analysis. A sample of the harvest supernatant was partially purified using ion exchange chromatography. Following dialysis into phosphate buffered saline, the yeast-produced MDC exhibited a single molecular mass of 8088 daltons, as compared with the theoretical value of 8086, well within the expected error of the measurement.

Yeast-produced MDC was further analyzed for biological activity by calcium flux assay and found to exhibit activity comparable to the activity of synthetic MDC and CHO-produced MDC. Using the assay described below in Example 25, yeast-produced MDC was also successful in competing with synthetic MDC-SEAP for binding to CCR4 recombinantly expressed on a mammalian cell surface.

EXAMPLE 10

Recombinant Production of MDC in Mammalian Cells

MDC was recombinantly produced in mammalian cells according to the following procedures.

A. Synthesis of Expression Vector 390HXE

A truncated version of the MDC cDNA was synthesized by PCR using pMP390-12 as template and the synthetic oligonucleotides 390RcH (SEQ ID NO: 14) and 390RcX (SEQ ID NO: 15) as primers. Primer 390RcH contains a Hind III restriction site followed by bases 1 to 20 of SEQ ID NO: 1; primer 390RcX contains an Xba I restriction site followed by the sequence complimentary to bases 403 to 385 of SEQ ID NO: 1.

The expected 423 bp PCR product was purified by agarose gel electrophoresis and cloned into Hind III/Xba I-digested pRc/CMV ((InVitrogen, San Diego Calif.) a vector which allows for direct expression in mammalian cells). The resulting plasmid, designated 390HXE, contained bases 1 to 403 of SEQ ID NO: 1. The sequence of the insert was confirmed by automated sequencing using the primers DC03 (SEQ ID NO: 16) and JHSP6 (SEQ ID NO: 3). Primer DC03 anneals to the pRc/CMV vector sequence adjacent to the cloning site.

B. Synthesis of Expression Vector 390HmX

Another MDC cDNA construct was generated by PCR, using pMP390-12 as template and the primers 390RcH (SEQ ID NO: 14) and 390mycRX (SEQ ID NO: 17). Primer 390mycRX contains an Xba I restriction site, a sequence complementary to the sequence encoding a "myc" epitope [Fowlkes et al., *BioTechniques*, 13:422–427 (1992)], and a sequence complementary to bases 298 to 278 of SEQ ID NO: 1. This reaction amplified the expected 354 bp fragment containing bases 1 to 298 of SEQ ID NO: 1 fused to a "myc" epitope at the MDC carboxy-terminus. This epitope can be used to facilitate immunoprecipitation, affinity purification, and detection of the MDC-myc fusion protein by Western blotting. The fragment was cloned into pRc/CMV to generate the plasmid 390HmX. The sequence of the insert was confirmed by automated sequencing using the primer DC03 (SEQ ID NO: 16).

C. Expression of MDC in 293T and NS0 Cells

Two transfection protocols were used to express the two MDC cDNA constructs described above in subparts A. and B.: transient transfection into the human embryonic kidney cell line 293T and stable transfection into the mouse myeloma cell line NS0 (ECACC 85110503).

Transient transfection of 293T cells was carried out by the calcium phosphate precipitation protocol of Chen and Okayama, *BioTechniques*, 6:632–638 (1988) and *Mol. Cel. Biol.*, 87:2745–2752 (1987). Cells and supernatants were harvested four days after transfection. A Northern blot was prepared from 4 µg of total RNA from each cell lysate and probed with a radiolabeled MDC fragment prepared by PCR. The template for the labeling reaction was a PCR fragment previously generated by amplifying pMP390 with the primers 390-1F (SEQ ID NO: 17) and 390-4R (SEQ ID NO: 9). Approximately 30 ng of this fragment was employed in a PCR reaction containing the following: 1.5 mM MgCl$_2$, 50 mM KCl, 10 mM Tris, pH 8.4, 0.2 mM dATP, 0.2 mM dTTP, 0.2 mM dGTP, 1 µM dCTP, 50 µCi α$^{32}$P-dCTP (DuPont/New England Nuclear, Boston Mass.), 2.5 U Taq polymerase, and 10 µg/ml each of primers 390-1F and 390-2R. The reaction was denatured by heating for 4 minutes at 94° C., followed by 15 cycles of amplification (denaturation for 15 seconds at 94° C., annealing for 15 seconds at 60° C., and extension for 30 seconds at 72° C.). The probe was purified by passage over a G-25 Quick Spin column (BMB). Conditions for hybridization were as follows: The filters were incubated at 42° C. for 16 hours with 5×10$^7$ counts per minute (cpm) of the probe, in 40–50 ml of a solution containing 50% formamide, 5× Denhardt's solution, 5×SSC (1×SSC is 0.15 M NaCl, 15 mM sodium citrate), 50 mM sodium phosphate, pH 6.5, and 0.1 mg/ml sheared salmon sperm DNA (Sigma, St. Louis Mo.).

Filters were subsequently washed in 0.5×SSC and 0.2% SDS at 42° C. for 30 minutes. Autoradiography was carried out at −80° C. with one intensifying screen for sixteen hours. The MDC DNA constructs were very highly expressed in the transfected cells and not detectable in the non-transfected cells.

For stable transfections, NS0 cells were grown to 80% confluency in D-MEM (Gibco), collected by centrifugation, and washed with PBS. Twenty µg of plasmid DNA was linearized with Sca I restriction endonuclease (BMB), added to the cells, and incubated on ice for 15 minutes in a 0.4 cm gap cuvette (BioRad, Hercules Calif.). The cells were electroporated with two pulses of 3 microfarad at 1.5 kilovolts. Cells were diluted into 20 ml D-MEM, incubated at 37° C. in 5% CO$_2$ for 24 hours, and selected by plating into 96-well plates at various dilutions in D-MEM containing 800 µg/ml geneticin. Wells containing single drug-resistant colonies were expanded in selective media. Total RNA was analyzed by Northern blotting as described in the preceding paragraph. Message for MDC was seen only in transfected cell lines.

MDC is purified from mammalian culture supernatants by, e.g., adapting methods described for the purification of recombinant TCA3 chemokine [Wilson et al., *J. Immunol.*, 145:2745–2750 (1990), or as described below in subpart F.

D. Expression of MDC in CHO Cells

Figure 8:
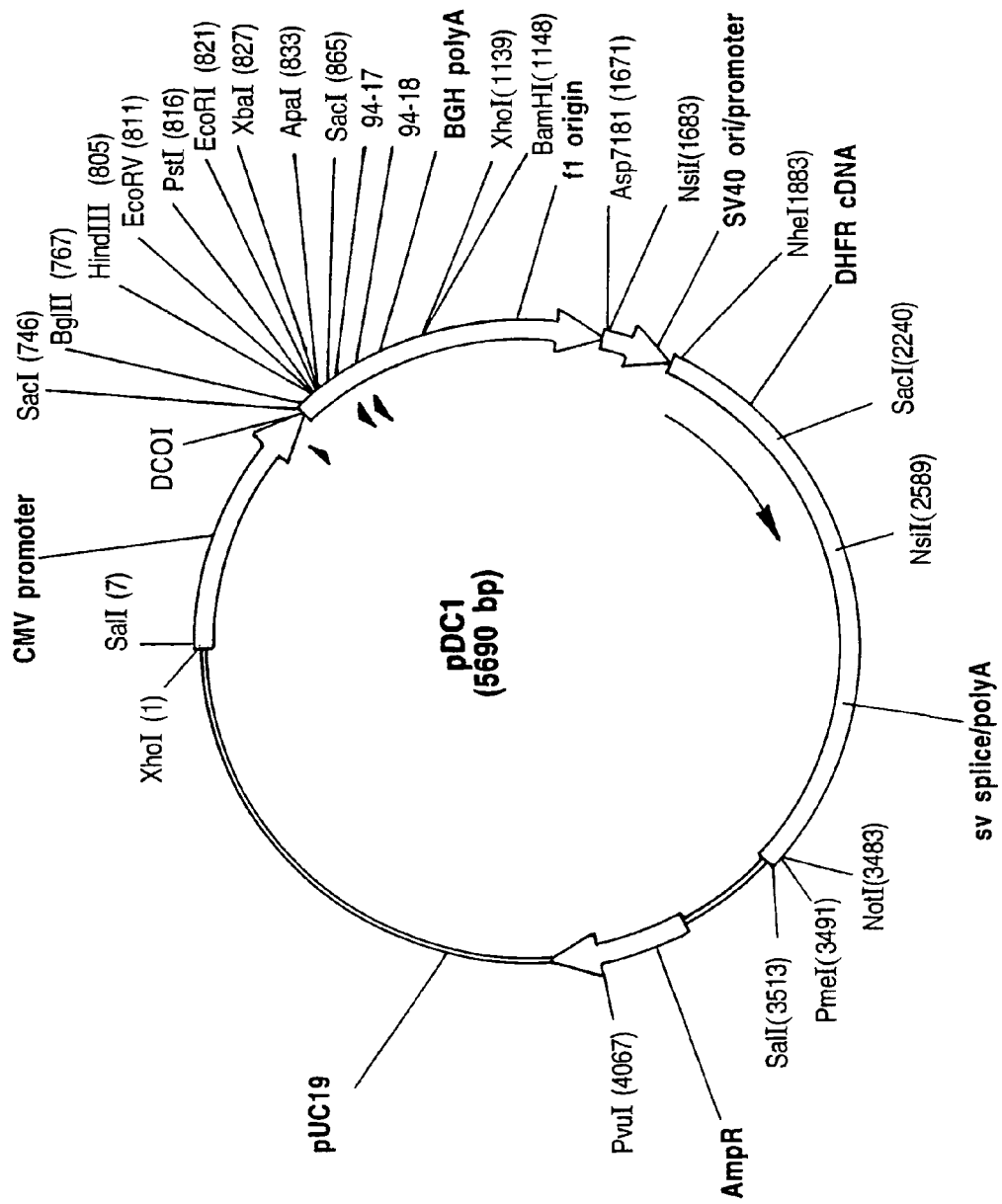

PCR was used to amplify bases 1 to 403 of the MDC cDNA clone (SEQ ID NO: 1) using primers 390RcH and 390RcX (SEQ. ID NOs: 14 and 15), as described above in subpart A. The fragment was cloned into the HindIII and XbaI sites of the expression vector pDC1, a pUC19 derivative that contains the cytomegalovirus (CMV) promoter to drive expression of the insert. More specifically, vector pDC1, depicted in FIG. 8, was derived from pRc/CMV and pSV2-dhfr (ATCC vector #37146). Vector pDC1 is similar to the mammalian expression vector pRc/CMV (Invitrogen, San Diego) except that pDC1 carries the mouse dihydrofolate reductase (dhfr) gene as a selectable marker, in place of the neomycin phosphotransferase gene. Transcription of the target gene in pDC1 is under the control of the strong CMV promoter. See Stenberg et al., *J. Virology,* 49:190–199 (1984). Additionally, a polyadenylation sequence from the bovine growth hormone gene [Goodwin and Rottman, *J. Biol. Chem.,* 267:16330–16334 (1992)] is provided on the 3' side of the target gene. The dhfr expression cassette [Subramani et al., *Mol. Cell. Biol* 1:854–864 (1981)] allows selection for pDC1 in cells lacking a functional dhfr gene.

XL-1 Blue bacteria (Stratagene) were transformed with the pDC1/MDC plasmid using standard techniques of $CaCl_2$ incubation and heat shock (Sambrook et al.). Transformants were grown in LB medium containing 100 μg/ml carbenicillin. Plasmid DNA from individual transformed clones was isolated using the Promega Wizard Maxiprep system (Madison, Wis.) and its sequence was confirmed by automated sequencing using the primers 390-1F and 390-2R (SEQ ID NOs: 7 & 8). The plasmid was linearized by restriction digestion with Pvu I endonuclease (Boehringer Mannheim), which cuts once within the vector sequence.

The Chinese hamster ovary (CHO) cell line used for production of MDC was DG-44, which was derived by deleting the dhfr gene. See Urlaub et al., *Cell,* 33:405 (1983). For electroporation, $10^7$ of these CHO cells were washed in PBS, resuspended in 1 ml PBS, mixed with 25 μg of linearized plasmid, and transferred to a 0.4 cm cuvette. The suspension was electroporated with a Biorad Gene Pulser (Richmond, Calif.) at 290 volts, 960 μFarad. Transfectants were selected by growth in $α^-$ medium (Cat. No. 12000, Gibco, Gaithersburg, Md.) containing 10% dialyzed fetal bovine serum (FBS) (Hyclone, Logan, Utah) and lacking hypoxanthine and thymidine. Cells from several hundred transfected colonies were pooled and re-plated in $α^-$ medium containing 20 nM methotrexate (Sigma, St. Louis, Mo.). Colonies surviving this round of selection were isolated and expanded in $α^-$ medium containing 20 nM methotrexate.

E. Purification of MDC for Protein Sequencing

Transfected CHO clones were grown on plastic tissue culture dishes to approximately 90% confluence in $α^-$ medium, at which time the medium was replaced with P5 medium containing 0.2% to 1.0% FBS. P5 medium consists of the components listed in Table 2, below (purchased as a premixed powder form Hyclone, Logan Utah), supplemented with the following additional components: (1) 3 g/l sodium bicarbonate (Sigma, St. Louis, Mo.); (2) 2 μg/l sodium selenite (Sigma); (3) 1% soy bean hydrolysate (Quest International, Naarden, The Netherlands); (4) 1×ferrous sulfate/EDTA solution (Sigma); (5) 1.45 ml/1 EX-CYTE VLE solution (Bayer, Kankakee, Ill.); (6) 10 μg/ml recombinant insulin (Nucellin, Eli Lily, Indianapolis, Ind.); (7) 0.1% pluronic F-68 (Sigma); (8) 30 μg/ml glycine (Sigma); (9) 50 μM ethanolamine (Sigma); and (10) 1 mM sodium pyruvate (Sigma).

TABLE 2

| Component | Powder #5 gm/L |
|---|---|
| INORGANIC SALTS | |
| Sodium Chloride | 4.0 |
| Potassium Chloride | 0.4 |
| Sodium Phosphate Dibasic, Anhydrous | 0.07102 |
| Sodium Phosphate Monobasic $H_2O$ | 0.0625 |
| Magnesium Sulfate, Anhydrous | 0.1 |
| Cupric sulfate 5 $H_2O$ | 0.00000125 |
| Ferrous Sulfate 7 $H_2O$ | 0.000417 |
| Zinc Sulfate 7 $H_2O$ | 0.0004315 |
| Ferric Nitrate 9 $H_2O$ | 0.00005 |
| Calcium Chloride, Anhydrous | 0.11661 |
| Magnesium Chloride, Anhydrous | 0 |
| AMINO ACIDS | |
| L-Alanine | 0 |
| L-Arginine HCl | 0.15 |
| L-Asparagine $H_2O$ | 0.075 |
| L-Aspartic Acid | 0.04 |
| L-Cysteine HCl $H_2O$ | 0.035 |
| L-Cysteine 2 HCl | 0.12 |
| L-Glutamic Acid | 0.02 |
| L-Glutamine | 0.5846 |
| Glycine | 0.02 |
| L-Histidine HCl $H_2O$ | 0.04 |
| L-Isoleucine | 0.15 |
| L-Leucine | 0.15 |
| L-Lysine HCl | 0.1 |
| L-Methionine | 0.05 |
| L-Proline | 0.05 |
| L-Phenylalanine | 0.05 |
| L-Serine | 0.075 |
| L-Threonine | 0.075 |
| L-Tryptophan | 0.02 |
| L-Tyrosine 2 Na 2 $H_2O$ | 0.075 |
| L-Valine | 0.125 |
| VITAMINS | |
| Biotin | 0.001 |
| D-Calcium Pantothenate | 0.0025 |
| Choline Chloride | 0.015 |
| Folic Acid | 0.005 |
| i-Inositol | 0.175 |
| Nicotinamide | 0.005 |
| Pyridoxal HCl | 0.005 |
| Pyridoxin HCl | 0.005 |
| Riboflavin | 0.001 |
| Thiamine HCl | 0.005 |
| Cyanocobalamine | 0.001 |
| OTHER | |
| D-Glucose | 1.0 |
| Hypoxanthine, Na | 0.005 |
| Thymidine | 0.005 |
| Putrescine 2HCl | 0.000081 |
| Sodium Pyruvate | 0.11004 |
| Linoleic Acid | 0.0001 |
| DL-Alpha-Lipoic Acid | 0.0002 |
| Phenol Red, Na Salt | 0.0086022 |

After two additional days in culture, an aliquot of each supernatant was mixed with an equal volume of acetone. The precipitated proteins were pelleted by centrifugation, fractionated on an 18% Tris Glycine gel (NOVEX), and blotted to a PVDF membrane (Millipore, Bedford, Mass.).

MDC bound to the membrane was detected by a crude preparation of monoclonal antibody to MDC (prepared as described in Example 18). Cells from the clone secreting the highest level of MDC protein (approx. 1 μg/ml) were removed from the plate by treatment with a solution of 0.5% trypsin and 5.3 mM EDTA (GIBCO) and used to start a suspension culture in $α^-$ medium plus 10% fetal bovine serum (FBS). Over the course of 8 days, 5 volumes of P5 medium were added to the culture. Proteins were precipitated from the culture supernatant by addition of polyethylene glycol (MW 8000, Union Carbide, Danbury, Conn.) to 20% (weight/volume), fractionated on an 18% Tris glycine gel, and electroblotted to a PVDF membrane (Millipore, Bedford, Mass.) in CAPS buffer (3-[Cyclohexylamino]-1-propanesulfonic acid, pH 10.4) (Sigma, St. Louis, Mo.). A strip of the filter was removed for detection of MDC by western blotting with the supernatant from a hybridoma cell line producing anti-MDC monoclonal antibodies (See Example 18). The reactive band, which migrated with an apparent molecular weight of 6.4 kD, was excised from the remaining portion of the filter.

Using an automated sequencer (Applied Biosystems, Model 473A, Foster City, Calif.), the sequence of the N-terminus of the protein was determined to be: GPYGA-NMEDS. This sequence is identical to that of residues 1 to 10 of SEQ ID NO. 2, corresponding to the N-terminus of the predicted mature form of MDC.

F. Purification of MDC for Biological Assays

For growth of larger cultures, MDC-expressing CHO cells were grown to 80% confluence on tissue culture plates in a medium. The cells were removed from the plates by treatment with trypsin and EDTA and resuspended at a density of $3\times10^5$ cells/ml in P5 medium plus 1% FBS in a spinner flask at 37° C. Additional P5/1% FBS medium was added as needed to keep the cell density in the range of $1\times10^6$ to $3\times10^6$.

After 11 days in culture, the cells were removed from the medium by filtration. The pH of the culture medium was adjusted to 6.8, and it was passed over a heparin-Sepharose CL-6B column (Pharmacia, Piscataway, N.J.). After washing with 0.2 M NaCl in potassium phosphate buffer, pH 7, the column was eluted with a linear gradient of 0.2 to 0.7 M NaCl. Fractions were analyzed by SDS-PAGE and Coomassie stained to determine which of them contained MDC. MDC eluted from the column at approximately 0.6 M NaCl.

The fractions containing MDC were pooled and concentrated by ultrafiltration in a stirred-cell chamber (Amicon, Beverly, Mass.) using a filter with a MW cutoff of 3 kD. Octylglucoside (10 mM final concentration, Boehringer Mannheim Biochemicals) was added to the concentrated MDC, which subsequently was passed through a Sephacryl HR100 column (Pharmacia, Piscataway, N.J.). Fractions were analyzed by SDS-PAGE for the presence of MDC. The final yield of MDC protein was approximately 0.1 mg/liter of culture supernatant, and the purity was estimated to be greater than 95%, as judged by Coomassie staining.

EXAMPLE 11

Production of MDC and MDC Analogs by Peptide Synthesis

MDC and MDC polypeptide analogs are prepared by chemical peptide synthesis using techniques that have been used successfully for the production of other chemokines such as IL-8 [Clark-Lewis et al., *J. Biol. Chem.*, 266: 23128–34 (1991)] and MCP-1. Such methods are advantageous because they are rapid, reliable for short sequences such as chemokines, and enable the selective introduction of novel, unnatural amino acids and other chemical modifications.

For example, MDC and MDC analogs were chemically synthesized using optimized stepwise solid-phase methods [Schnolzer et al., *Int. J. Pept. Protein Res.*, 40:180 (1992)] based on t-butyloxycarbonyl (Boc) chemistries of Merrifield [*J. Am. Chem. Soc.*, 85:2149–2154 (1963)] on an Applied Biosystems 430A Peptide Synthesizer roster City, Calif.). The proteins were purified by reverse-phase HPLC and characterized by standard methods, including electrospray mass spectrometry and nuclear magnetic resonance.

The chemically synthesized MDC corresponded to the mature form of recombinant MDC, consisting of residues 1 to 69 of SEQ ID NO. 2. Several methods were used to compare the chemically synthesized MDC to the recombinant MDC produced by CHO cell transfectants as described in Example 10. The migration of chemically synthesized MDC was identical to that of the recombinant MDC in denaturing SDS-PAGE (18% Tris glycine gel, NOVEX). In addition, the proteins reacted similarly in western blot analysis using monoclonal and polyclonal antibodies raised against bacterially produced MDC as described below in Example 18. The chemically synthesized MDC also appeared to behave in the same manner as the recombinant MDC in immunoprecipitation assays with the anti-MDC monoclonal antibodies. These studies indicate that the denatured and the non-denatured structures of chemically synthesized MDC are similar to those of recombinant MDC.

The following MDC analogs also have been chemically synthesized:

1. "MDC (n+1)" (SEQ ID NO: 30) consists of Leucine followed by residues 1 to 69 of SEQ ID NO. 2. This analog has alternatively been referred to herein as "MDC (0–69)."

2. "MDC (9–69)" consists of residues 9 to 69 of SEQ ID NO. 2.

3. "MDC-yl" (SEQ ID NO: 31) consists of residues 1 to 69 of SEQ ID NO. 2, with the following substitution: Residues 59–60 (Trp-Val) were replaced with the sequence Tyr-Leu. A related analog "MDC-wvas" consists of residues 1 to 69 of SEQ ID NO. 2, with the following substitution: Residues 59–60 (Trp-Val) were replaced with the sequence Ala-Ser.

4. "MDC-eyfy" (SEQ ID NO: 32) consists of residues 1 to 69 of SEQ ID NO. 2, with the following substitution: Residues 28–31 (His-Phe-Tyr-Trp) were replaced with the sequence Glu-Tyr-Phe-Tyr, derived from the amino acid sequence of the chemokine RANTES (residues 26–29 of SEQ ID NO: 21).

The analogs "MDC (n+1)", "MDC (9–69)", and "MDC-yl" are expected to be antagonists of MDC activity, inhibiting MDC activity by competitively binding to the same receptor that recognizes MDC. Alternatively, they may effect inhibition by forming inactive heterodimers with the native MDC. Possible activities of the analog "MDC-eyfy" include inhibition of MDC as described for the previous analogs. Alternatively, "MDC-eyfy" may confer some of the activities typical of the chemokine RANTES, such as chemotaxis of T lymphocytes, monocytes, or eosinophils.

Additionally, the following single-amino acid alterations (alone or in combination) are specifically contemplated: (1) substitution of a non-basic amino acid for the basic arginine and/or lysine amino acids at positions 24 and 27, respectively, of SEQ ID NO: 2; (2) substitution of a charged or polar amino acid (e.g., serine, lysine, arginine, histidine, aspartate, glutamate, asparagine, glutamine or cysteine) for the tyrosine amino acid at position 30 of SEQ ID NO: 2, the tryptophan amino acid at position 59 of SEQ ID NO: 2, and/or the valine amino acid at position 60 of SEQ ID NO: 2; and (3) substitution of a basic or small, non-charged amino acid (e.g., lysine, arginine, histidine, glycine, alanine) for the glutamic acid amino acid at position 50 of SEQ ID NO: 2. Specific analogs having these amino acid alterations are encompassed by the following formula (SEQ ID NO: 25):

```
Met Ala Arg Leu Gln Thr Ala Leu Leu Val Val Leu Val Leu Leu Ala
-24             -20                 -15                 -10

Val Ala Leu Gln Ala Thr Glu Ala Gly Pro Tyr Gly Ala Asn Met Glu
             -5                       1               5

Asp Ser Val Cys Cys Arg Asp Tyr Val Arg Tyr Arg Leu Pro Leu Xaa
         10              15              20

Val Val Xaa His Phe Xaa Trp Thr Ser Asp Ser Cys Pro Arg Pro Gly
 25                  30              35                      40

Val Val Leu Leu Thr Phe Arg Asp Lys Xaa Ile Cys Ala Asp Pro Arg
                 45              50              55

Val Pro Xaa Xaa Lys Met Ile Leu Asn Lys Leu Ser Gln
             60                  65
``` wherein the amino acid at position 24 is selected from the group consisting of arginine, glycine, alanine, valine, leucine, isoleucine, proline, serine, threonine, phenylalanine, tyrosine, tryptophan, aspartate, glutamate, asparagine, glutamine, cysteine, and methionine; wherein the amino acid at position 27 is independently selected from the group consisting of lysine, glycine, alanine, valine, leucine, isoleucine, proline, serine, threonine, phenylalanine, tyrosine, tryptophan, aspartate, glutamate, asparagine, glutamine, cysteine, and methionine; wherein the amino acid at position 30 is independently selected from the group consisting of tyrosine, serine, lysine, arginine, histidine, aspartate, glutamate, asparagine, glutamine, and cysteine; wherein the amino acid at position 50 is independently selected from the group consisting of glutamic acid, lysine, arginine, histidine, glycine, and alanine; wherein the amino acid at position 59 is independently selected from the group consisting of tryptophan, serine, lysine, arginine, histidine, aspartate, glutamate, asparagine, glutamine, and cysteine; and wherein the amino acid at position 60 is independently selected from the group consisting of valine, serine, lysine, arginine, histidine, aspartate, glutamate, asparagine, glutamine, and cysteine. Such MDC polypeptide analogs are specifically contemplated to modulate the binding characteristics of MDC to chemokine receptors and/or other molecules (e.g., heparin, glycosaminoglycans, erythrocyte chemokine receptors) that are considered to be important in presenting MDC to its receptor.

Additionally, analogs wherein the proline at position 2 of SEQ ID NO: 1 is deleted or substituted for by another amino acid are specifically contemplated. Such mutants will collectively be referred to as "MDCΔ$Pro_2$ polypeptides." As described below in Example 20, MDC (3–69) derived from an HIV-infected T cell line displays properties that are, at least in some respects, opposite or antagonistic from properties observed for mature MDC (1–69). It is hypothesized that a dipeptidyl amino peptidase such as CD26 [Oravecz et al., *J. Exper. Med.,* 186:1865 (1997)] possesses a specificity for the sequence $NH_2$-X-Pro (wherein X is any amino acid), and that the dipeptidase therefore is capable of converting mature MDC (1–69) (having the amino terminus $NH_2$-Gly-Pro-Tyr) to the MDC (3–69) form in vivo. It is expected that the dipeptidase CD26 will not cleave the amino terminus from MDCΔ$Pro_2$ polypeptides, rendering such mutants more stable than MDC(1–69) in vivo. MDCΔ$Pro_2$ polypeptides that retain the biological activities of mature MDC (1–69) are useful in all therapeutic indications wherein MDC (1–69) is useful as a therapeutic, whereas MDCΔ$Pro_2$ polypeptides that antagonize the activity of mature MDC (1–69) (e.g., by competitively binding but failing to signal through CCR4) are useful as MDC antagonists. In preferred embodiments, substitution of the proline with a glycine, alanine, valine, leucine, isoleucine, serine, threonine, phenylalanine, tyrosine, or tryptophan is contemplated. Introducing the MDCΔ$Pro_2$ mutation into any of the analogs described above is also specifically contemplated.

After synthesis, synthetic MDC or MDC analogs may be reduced and refolded substantially as described in Example 8 for bacterially-produced MDC bound in inclusion bodies, or using procedures that are well-known in the art. See, e.g., *Protein Folding*, T. E. Creighton (Ed.), W.H. Freeman & Co., New York, N.Y. (1992): van Kimmenade et al., *Eur. J. Biochem.,* 173: 109–114 (1988); and PCT publication no. WO 89/01046.

Recombinant techniques such as those described in the preceding examples also are contemplated for preparing MDC polypeptide analogs. More particularly, polynucleotides encoding MDC are modified to encode polypeptide analogs of interest using well-known techniques, e.g., site-directed mutagenesis and the polymerase chain reaction. See generally Sambrook et al., supra, Chapter 15. The modified polynucleotides are expressed recombinantly, and the recombinant MDC polypeptide analogs are purified, as described in the preceding examples.

The chemoattractant and/or cell-activation properties of MDC or MDC polypeptide analogs on one or more types of cells involved in the inflammatory process (e.g., T lymphocytes, monocytes, macrophages, basophils, eosinophils, neutrophils, mast cells, and natural killer cells), on endothelial cells, epithelial cells, fibroblasts, or others are assayed by art-recognized techniques that have been used for numerous other chemokines. Native MDC, recombinant MDC or MDC polypeptide analogs, or synthetic MDC or MDC polypeptide analogs purified and isolated as described in one or more of the preceding examples are assayed for activity as described in the following examples with respect to MDC.

EXAMPLE 12

Assay of MDC Effects Upon Basophils, Mast Cells, and Eosinophils

The effect of MDC upon basophils, mast cells, and eosinophils is assayed, e.g., by methods described by Weber et al., *J. Immunol.,* 154:4166–4172 (1995) for the assay of MCP-1/2/3 activities. In these methods, changes in free cytosolic calcium and release of proinflammatory mediators (such as histamine and leukotriene) are measured. Blocking chemokine-mediated activation of these cell types has implications in the treatment of late-phase allergic reactions, in which secretion of proinflammatory mediators plays a significant role [Weber et al., supra].

In one signaling assay, synthetic MDC (0.01–10 nM) caused dose-dependent chemotaxis of purified human eosinophils (maximum chemotaxis approximately four-fold greater than in controls). The relative chemotactic activity of MDC, in relation to other known chemotactic factors of eosinophils, was as follows: MDC≈eotaxin<RANTES<MCP-4<eotaxin-2. Eotaxin-2 and MCP-4 were especially potent, whereas RANTES effects were intermediate, about one log less potent than MCP-4 or eotaxin-2. MDC induced eosinophil migration and shape change even though it did not elicit measurable cytosolic calcium elevations in the eosinophils during these responses. In contrast, the MDC analog MDC(9–69) displayed no chemotactic activity in the same assay. This data demonstrates a biological activity and utility for MDC in stimulating the chemotaxis of eosinophils, and further demonstrates a utility of MDC modulators for modulating this chemotactic activity.

In reported studies with human eosinophils, CCR3 was identified as a critical receptor for a variety of CC chemokines that exert effects on eosinophils, including eotaxin, RANTES, MCP4 and eotaxin-2. See, e.g., Garcia-Zepeda, et al., *J. Immunol.* 157:5613 (1996); Forssman et al., *J. Exp. Med.*, 185:2171 (1997); Stellato et al., *J. Clin. Invest.*, 99:926 (1997); and White et al., *J. Leukoc. Biol.* 62:667 (1997). Also, as reported elsewhere herein, the chemokine MDC binds and signals through the chemokine receptor CCR4. However, it was determined that the eosinophil-chemotactic activity of MDC appears to operate in a manner independent of the chemokine receptors CCR3 and CCR4. CCR3-transfected HEK cells labeled with Fura-2 demonstrated a rapid rise in intracellular free calcium following stimulation with 10–50 nM eotaxin, eotaxin-2, or MCP-4, but not with 10–100 nM MDC. Similarly, purified eosinophils cultured for 72 hours in 10 ng/ml IL-5 and labeled with Fura-2 demonstrated a rapid rise in intracellular free calcium following stimulation with 10–50 nM eotaxin, eotaxin-2, or MCP-4, whereas no such rise was observed following stimulation with MDC (up to 100 nM). In addition, a CCR3 blocking monoclonal antibody was found to inhibit eotaxin- and eotaxin-2-induced chemotaxis of eosinophils, but not chemotaxis induced by MDC.

Two lines of evidence suggest that MDC-induced chemotaxis of eosinophils operates independently of CCR4. First, eosinophil cDNA (generated from eosinophil RNA using oligo-dT or random primers) was screened via PCR. CCR4 could not be detected in either the oligo-dT or random primed cDNA, even though the same PCR primers amplified CCR4 from genomic DNA, and even though CCR3 mRNA was readily amplifyable. Thus, it appears that eosinophils do not express CCR4. Second, chemotaxis experiments with TARC, a chemokine known to signal through CCR4, have failed (at concentrations up to 100 nM) to induce chemotaxis of eosinophils.

The fact that MDC apparently exerts its effects on eosinophils in a CCR4-independent manner indicates that, when selecting MDC modulators to treat allergic reactions in which eosinophils play a role, modulators that will have fewer side-effects are those that modulate MDC-induced chemotaxis of eosinophils without modulating MDC's signaling through CCR4. Assays are provided herein to select such modulators.

EXAMPLE 13

Assay of Chemoattractant and Cell-Activation Properties of MDC upon Human Monocytes/Macrophages and Human Neutrophils The effects of MDC upon human monocytes/macrophages or human neutrophils is evaluated, e.g., by methods described by Devi et al., *J. Immunol.*, 153:5376–5383 (1995) for evaluating murine TCA3-induced activation of neutrophils and macrophages. Indices of activation measured in such studies include increased adhesion to fibrinogen due to integrin activation, chemotaxis, induction of reactive nitrogen intermediates, respiratory burst (superoxide and hydrogen peroxide production), and exocytosis of lysozyme and elastase in the presence of cytochalasin B. As discussed by Devi et al., these activities correlate to several stages of the leukocyte response to inflammation. This leukocyte response, reviewed by Springer, *Cell*, 76:301–314 (1994), involves adherence of leukocytes to endothelial cells of blood vessels, migration through the endothelial layer, chemotaxis toward a source of chemokines, and site-specific release of inflammatory mediators. The involvement of MDC at any one of these stages provides an important target for clinical intervention, for modulating the inflammatory response.

In one art-recognized chemotaxis assay, a modified Boyden chamber assay, leukocytes to be tested are fluorescently labeled with calcein by incubating for 20 minutes at room temperature. The labeled cells are washed twice with serum-free RPMI, resuspended in RPMI containing 2 mg/ml of BSA, and then added quantitatively to the upper wells of the chambers, which are separated from the lower wells by a polycarbonate filter (Neuroprobe Inc. Cabin John, MD). MDC diluted in the same medium as the leukocytes is added to the lower wells at various concentrations. Chambers are incubated for 2 hours at 37° C. At the end of the assay, cells that have not migrated through the membrane are removed by rinsing the filter with PBS and scraping with a rubber policeman. Cells that have migrated through the filter are quantitated by reading fluorescence per well in a fluorescent plate reader (Cytofluor, Millipore Inc., Boston, Mass.).

A series of experiments were performed using art-recognized procedures to determine the chemotactic properties of MDC. Initially, the response of human mononuclear cells to MDC was determined. The effect of MDC on the chemotactic response of polymorphonuclear leukocytes (granulocytes) also was examined.

It has been established that MCP-1, which is a C—C chemokine, causes both recruitment and activation of monocytes but appears to have limited ability to induce the migration of macrophages. The failure of MCP-1 to attract macrophages appears to be correlated to the differentiation process: as monocytic cells differentiate, there is a progressive decrease in cell response to MCP-1 [Denholm and Stankus, *Cytokine*, 7: 436–440 (1995)]. The biological activities of MCP-1 appear to correlate with the expression of this chemokine, with MCP-1 mRNA being found in monocytes but decreasing as these cells differentiate.

The pattern of expression of MDC appears to be the reverse of that described for MCP-1, with the amount of mRNA for MDC increasing as monocytes differentiate to macrophages. To determine whether this expression pattern correlates to the biological response to MDC, the effects of MDC on the migration of monocytes and macrophages were compared.

A number of different leukocyte cells types were analyzed in chemotaxis and chemotaxis inhibition assays. Human mononuclear and polymorphonuclear leukocytes were isolated from peripheral blood using methods known in the art [Denholm et al., *Amer. J. Pathol.*, 135:571–580 (1989)]. Second, the human monocytic cell line, THP-1 (obtained from the ATCC, Rockville, Md., and maintained in culture in RPMI with 10% FBS and with penicillin/streptomycin) was employed. THP-1 cells can be cultured as monocytes or can be induced to differentiate to macrophages by treatment with phorbol myristate acetate (PMA) [Denholm and Stankus, *Cytokine*, 7:436–440 (1995)]. In some experiments monocytic THP-1 cells were employed, and in others monocytic THP-1 cells were differentiated to macrophages by incubation with phorbol myristate acetate (PMA). Third, guinea pig peritoneal macrophages were obtained essentially as described in Yoshimura, *J. Immunol.*, 150:5025–5032 (1993). Briefly, animals were given an intraperitoneal injection of 3% sterile thioglycolate (DIFCO) two days prior to cell harvest. Macrophages were obtained from the peritoneal cavity by lavage with phosphate buffered saline (PBS) with 1 mM EDTA and 0.1% glucose. Cells were washed once by centrifugation and then utilized in chemotaxis assays as described below.

Assays of chemotactic activity were carried out, using the cell preparations described above, essentially as described by Denholm and Stankus, *Cytometry*, 19:366–369 (1995), using 96-well chambers (Neuroprobe Inc., Cabin John, MD) and cells labeled with the fluorescent dye, calcein (Molecular Probes, Eugene, Oreg.). Polycarbonate filters used in this assay were PVP-free (Neuroprobe Inc.); filter pore sizes used for different cell types were: 5 μm for monocytes and THP-1 cells, 3 μm for polymorphonuclear leukocytes, and 8 μm for guinea pig macrophages.

Fifty thousand calcein labelled cells were resuspended in RPMI medium containing 2 mg/ml BSA and placed in the upper wells. MDC or other test substances were diluted in RPMI with BSA (e.g., final MDC concentrations of 25, 50, 100, 250 ng/ml) and placed in the lower wells. Following incubation at 37° C. for 2 hours, unmigrated cells remaining above the filter were removed by wiping; the filter was then air-dried. Controls in these assays were: RPMI with BSA as the negative control, and 50 ng/ml of MCP-1 and 1% zymosan activated serum (ZAS, prepared as described [Denholm and Lewis, *Amer. J. Pathol.*, 126:464–474, (1987)]) were used as positive controls. Migration of cells was quantitated on a fluorescent plate reader (Cytofluor, Millipore Inc. Bedford, Mass.) and the number of cells migrated expressed as fluorescent units.

In assays of inhibitory activity, cells in the upper wells of the chambers were suspended in varying concentrations (0.005, 0.05, 0.5, 5.0, and 50 ng/ml) of MDC. The lower wells of the chamber were filled with either medium alone or the chemotactic factors, MCP-1 or zymosan activated serum (ZAS). Inhibition was assessed by comparing the number of cells that migrated to MCP-1 or ZAS, in the absence of MDC, to the number of cells that migrated with increasing concentrations of MDC. Preparation of cells and quantitation of assays was performed exactly as described above for the chemotaxis assays. The number of cells migrated was expressed as fluorescent units.

As indicated in FIG. 2, MDC did not induce THP-1-derived mononuclear cell migration, but rather appeared to inhibit mononuclear cell migration, at concentrations between 10 and 100 ng/ml. Other C—C chemokines, such as MCP-1 and RANTES, typically induce maximal monocyte chemotaxis within this concentration range.

Figure 3:
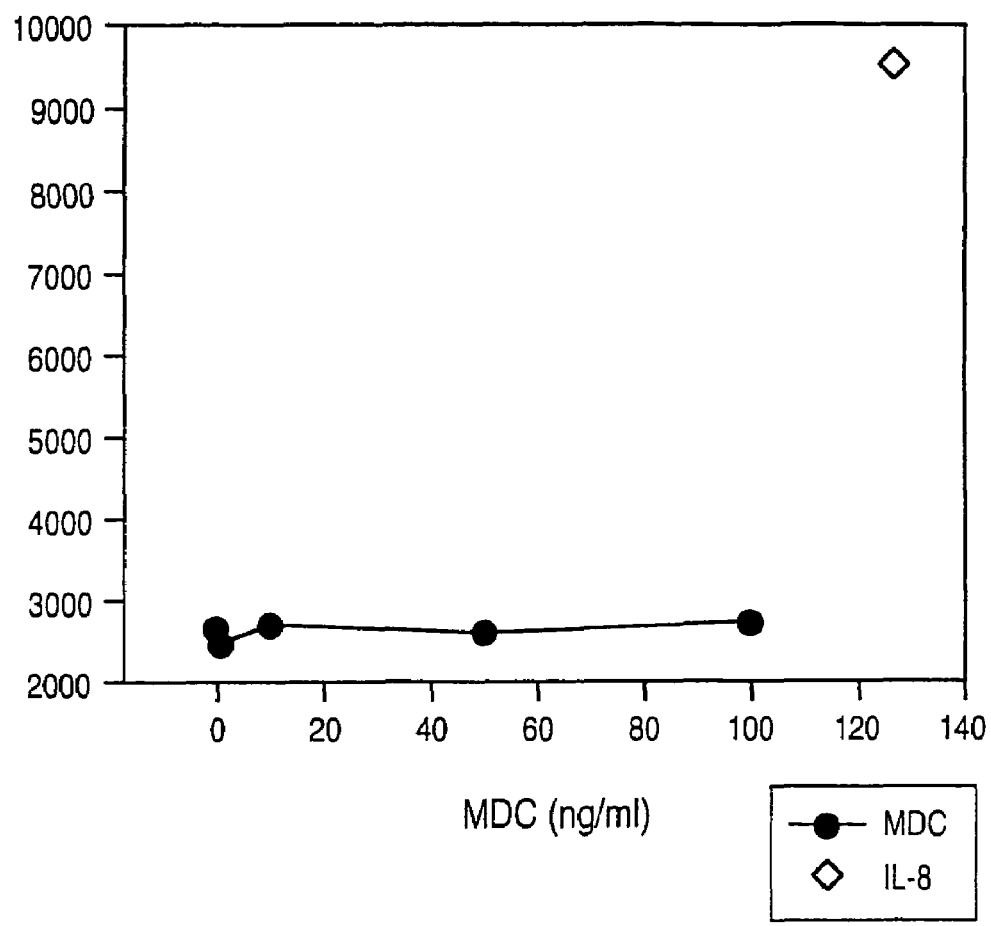

As shown in FIG. 3, MDC, at concentrations of 0.001 to 100 ng/ml had no net effect on granulocyte migration. In respect to this lack of effect on granulocyte chemotaxis, MDC is similar to other previously described C—C chemokines.

Figure 4:
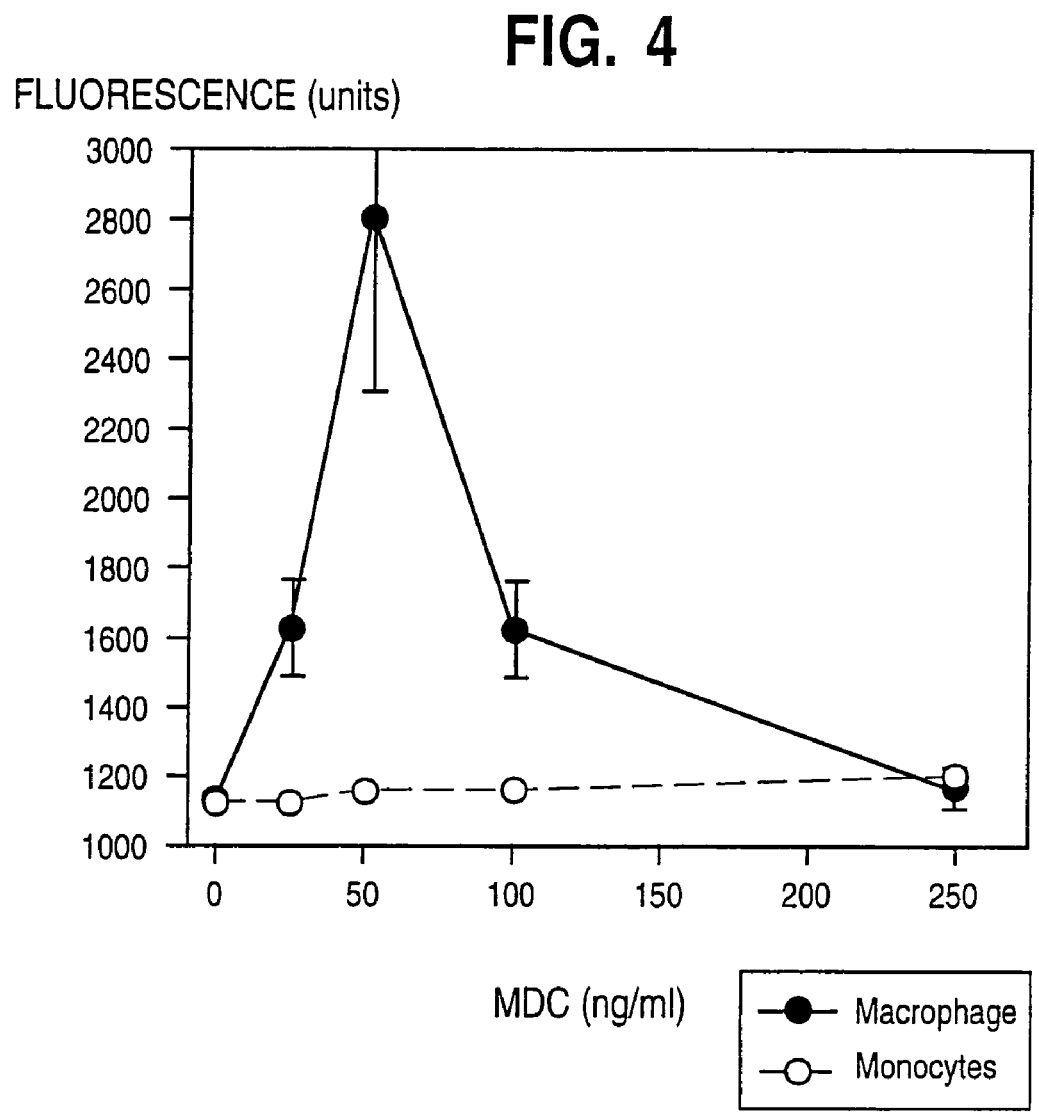

The response of both macrophage and monocyte THP-1 cells to MDC is shown in FIG. 4. Macrophages (closed circles) migrated to MDC in a dose dependent manner, with optimal activity at 50 ng/ml. The decrease in macrophage chemotactic response to MDC at higher concentrations (100 ng/ml) reflects a desensitization of cells which is typical of most chemotactic factors at high concentrations [Falk and Leonard, *Infect. Immunol.*, 32:464–468 (1981)]. Monocytic THP-1 cells (open circles) however, did not migrate to MDC.

Figure 5:
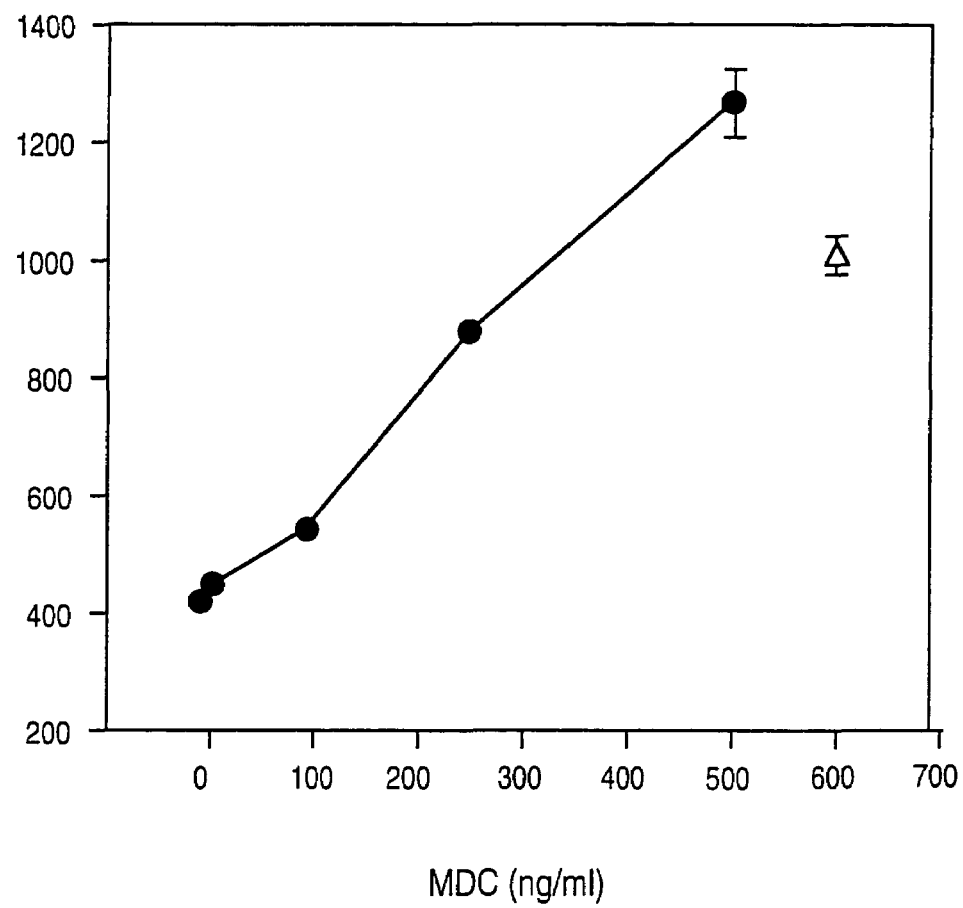

The chemotactic activity of MDC for macrophages was further verified in experiments utilizing elicited guinea pig peritoneal macrophages. MDC induced a dose dependent migration of guinea pig macrophages (FIG. 5), at concentrations between 100 and 500 ng/ml. The concentrations necessary to induce the migration of guinea pig macrophages was approximately ten-fold of that for human cells (FIG. 4). Similar differences in concentrations necessary for peak biological activity of human chemokines in other species have been reported for MCP-1 by Yashimura, *J. Immunol.*, 150:5025–5032 (1993).

The results of these experiments suggest that the biological activities of MDC are linked to the differentiation of monocytes to macrophages. In contrast to MCP-1 [Yoshimura, *J. Immunol.*, 150:5025–5032 (1993)], MDC induces macrophage but not monocyte chemotaxis.

The ability of MDC to attract macrophages indicates that this chemokine might act to induce the focal accumulation of tissue macrophages. The accumulation of tissue macrophages in specific areas is important in the formation of granulomas, in which lung macrophages act to surround and enclose foreign particulates or relatively nondestructible bacterial pathogens such as *Mycobacterium* sp. [Adams, *Am. J. Pathol.*, 84:164–191 (1976)].

In certain conditions such as arthritis, the accumulation of macrophages is understood to be detrimental and destructive. The ability of MDC to promote macrophage chemotaxis indicates a therapeutic utility for MDC inhibitors of the invention, to prevent, reduce, or eliminate macrophage accumulation in tissues.

Figure 6:
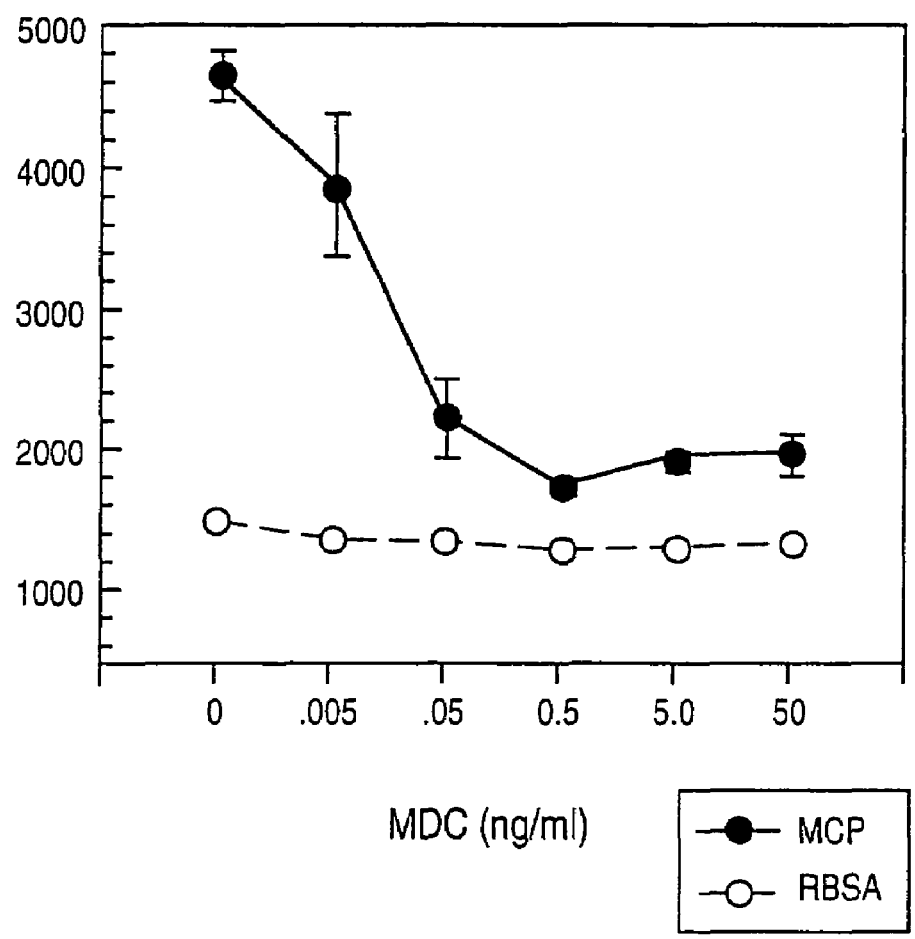

The results of the chemotaxis assays with human mononuclear cells, presented in FIG. 2, suggested that MDC might inhibit cell migration. In the absence of MDC, monocytic THP-1 cells migrate to MCP-1, as shown in FIG. 6 (MDC of 0 ng/ml). However, when cells are exposed to MDC, the chemotactic response to MCP-1 (closed circles) is decreased. MDC, at concentrations of 0.005–0.5 ng/ml, inhibited monocyte chemotactic response to MCP-1. Although MDC inhibited the chemotactic response of monocytes to MCP-1, there was no significant effect of MDC on chemokinesis, or random migration, as reflected by the numbers of cells migrating to medium alone (open circles, RPMI with BSA), either in the presence of absence of MDC.

The inhibitory activity of MDC on monocyte chemotaxis indicates therapeutic utility for MDC in the treatment of several chronic inflammatory conditions (atherosclerosis, arthritis, pulmonary fibrosis) in which monocyte chemotaxis appears to play an important pathogenic role. Enhancing the activity of MDC in such diseases might result in the decreased migration of monocytes into tissues, thereby lessening the severity of disease symptoms.

EXAMPLE 14

MDC In Vivo Tumor Growth Inhibition Assay

Tumor growth-inhibition properties of MDC are assayed, e.g., by modifying the protocol described by Laning et al., *J. Immunol.*, 153:4625–4635 (1994) for assaying the tumor growth-inhibitory properties of murine TCA3. An MDC-encoding cDNA is transfected by electroporation into the myeloma-derived cell line J558 (American Type Culture Collection, Rockville, Md.). Transfectants are screened for MDC production by standard techniques such as ELISA (enzyme-linked immunoadsorbant assay) using a monoclonal antibody generated against MDC as detailed in Example 18. A bolus of 10 million cells from an MDC-producing clone is injected subcutaneously into the lower right quadrant of BALB/c mice. For comparison, 10 million non-transfected cells are injected into control mice. The rate and frequency of tumor formation in the two groups is compared to determine efficacy of MDC in inhibiting tumor growth. The nature of the cellular infiltrate subsequently associated with the tumor cells is identified by histologic means. In addition, recombinant MDC (20 ng) is mixed with non-transfected J558 cells and injected (20 ng/day) into tumors derived from such cells, to assay the effect of MDC administered exogenously to tumor cells.

EXAMPLE 15

Intraperitoneal Injection Assay

The cells which respond to MDC in vivo are determined through injection of 1–1000 ng of purified MDC into the intraperitoneal cavity of mice or other mammals (e.g., rabbits or guinea pigs), as described by Luo et al., *J. Immunol.*, 153:4616–4624 (1994). Following injection, leukocytes are isolated from peripheral blood and from the peritoneal cavity and identified by staining with the Diff Quick kit (Baxter, McGraw, Ill.). The profile of leukocytes is measured at various times to assess the kinetics of appearance of different cell types. In separate experiments, neutralizing antibodies directed against MDC (Example 18) are injected along with MDC to confirm that the infiltration of leukocytes is due to the activity of MDC.

EXAMPLE 16

In Vivo Activity Assay—Subcutaneous Injection

The chemoattractant properties of MDC are assayed in vivo by adapting the protocol described by Meurer et al., *J. Exp. Med.*, 178:1913–1921 (1993). Recombinant MDC (10–500 pmol/site) is injected intradermally into a suitable mammal, e.g., dogs or rabbits. At times of 4 to 24 hours, cell infiltration at the site of injection is assessed by histologic methods. The presence of MDC is confirmed by immunocytochemistry using antibodies directed against MDC. The nature of the cellular infiltrate is identified by staining with Baxter's Diff Quick kit.

EXAMPLE 17

Myelosuppression Activity Assays

The myelosuppressive activity of MDC is assayed by injection of MDC into mice or another mammal (e.g. rabbits, guinea pigs), e.g., as described by Maze et al., *J. Immunol.*, 149:1004–1009 (1992) for the measurement of the myelosuppressive action of MIP-1α. A single dose of 0.2 to 10 ug of recombinant MDC is intravenously injected into C3H/HeJ mice (Jackson Laboratories, Bar Harbor Me.). The myelosuppressive effect of the chemokine is determined by measuring the cycling rates of myeloid progenitor cells in the femoral bone marrow and spleen. The suppression of growth and division of progenitor cells has clinical implications in the treatment of patients receiving chemotherapy or radiation therapy. The myeloprotective effect of such chemokine treatment has been demonstrated in pre-clinical models by Dunlop et al., *Blood*, 79:2221 (1992).

An in vitro assay also is employed to measure the effect of MDC on myelosuppression, in the same manner as described previously for derivatives of the chemokines interleukin-8 (IL-8) and platelet factor 4 (PF-4). See Daly et al., *J. Biol. Chem.*, 270:23282 (1995). Briefly, low density (less than 1.077 g/cm) normal human bone marrow cells are plated in 0.3% agar culture medium with 10% fetal bovine serum (HyClone, Logan, Utah) with 100 units/ml recombinant human GM-CSF (R&D Systems, Minneapolis, Minn.) plus 50 ng/ml recombinant human Steel factor (Immunex Corp., Seattle, Wash.) in the absence (control) and presence of MDC for assessment of granulocyte-macrophage precursors. For assessment of granulocyte erythroid myeloid megakaryocyte colony forming units (CFU-GEMM) and erythroid burst forming units (BFU-E), cells are grown in 0.9% methylcellulose culture medium in the presence of recombinant human erythropoietin (1–2 units/ml) in combination with 50 ng/ml Steel factor. Plates are scored for colonies after incubation at 37° C. in lowered (5%) $O_2$ for 14 days. The combination of GM-CSF and Steel factor or erythropoietin and Steel factor allow detection of large colonies (usually >1000 cells/colony) which come from early, more immature subsets of granulocyte myeloid colony forming units (CFU-GM), CFU-GEMM, and BFU-E.

EXAMPLE 18

Antibodies to Human MDC

A. Monoclonal Antibodies

Recombinant MDC, produced by cleavage of a GST-MDC fusion protein as described in Example 6, was used to immunize a mouse for generation of monoclonal antibodies. In addition, a separate mouse was immunized with a chemically synthesized peptide corresponding to the N-terminus of the mature form of MDC (residues 1 to 12 of SEQ ID NO. 2). The peptide was synthesized on an Applied Biosystem Model 473A Peptide Synthesizer (Foster City, Calif.), and conjugated to Keyhole Lympet Hemocyanine (Pierce), according to the manufacturer's recommendations. For the initial injection to produce "Fusion 191" hybridomas, approximately 10 μg of MDC protein or conjugated peptide was emulsified with Freund's Complete Adjuvant and injected subcutaneously. At intervals of two to three weeks, additional aliquots of MDC protein were emulsified with Freund's Incomplete Adjuvant and injected subcutaneously. Prior to the final prefusion boost, a sample of serum was taken from the immunized mice. These sera were assayed by western blot to confirm their reactivity with MDC protein. For a prefusion boost, the mouse was injected with MDC in PBS, and four days later the mouse was sacrificed and its spleen removed.

For the production of "Fusion 252" hybridomas, a mouse was immunized with the MDC(0–69) chemically synthesized peptide (See Example 11). On Day 0, the mouse was pre-bled and injected subcutaneously at two sites with 10 ug of MDC(0–69) in 200 ul complete Freund's adjuvant. On Day 22, the mouse was boosted with 30 ug of MDC(0–69) in 150 ul of incomplete Freund's adjuvant. On Day 40, the mouse was boosted with 20 ug MDC(0–69) in 100 ul of incomplete Freund's adjuvant. On day 54, blood was drawn and screened for anti-MDC antibodies via western blot, and reactivity was observed against MDC. On days 127 through 130, the mouse was injected on each of four consecutive days with 10 ug of MDC(0–69) in a volume of 200 ul PBS. On day 131, the mouse was sacrificed and the spleen was removed for a fusion.

For the production of "Fusion 272" hybridomas, a mouse was treated in a similar fashion as the mouse for fusion 252, except, on day 356, the mouse was boosted with MDC (0–69) in incomplete Freund's adjuvant. Test bleeds were taken on day 367 and screened by ELISA. On days 385, 386, 387, and 388, the mouse was boosted with 5 μg injections of MDC(0–69). On day 389 the spleen was removed for a fusion.

The spleens were placed in 10 ml serum-free RPMI 1640, and single cell suspensions were formed by grinding the spleens between the frosted ends of two glass microscope slides submerged in serum-free RPMI 1640, supplemented with 2 mM L-glutamine, 1 mM sodium pyruvate, 100 units/ml penicillin, and 100 μg/ml streptomycin (RPMI) (Gibco, Canada). The cell suspensions were filtered through a sterile 70-mesh Nitex cell strainer (Becton Dickinson, Parsippany, N.J.), and were washed twice by centrifuging at 200 g for 5 minutes and resuspending the pellet in 10 ml serum-free RPMI. Thymocytes taken from three naive Balb/c mice were prepared in a similar manner and used as a Feeder Layer. NS-1 myeloma cells, kept in log phase in RPMI with 10% fetal bovine serum (FBS) (Hyclone Laboratories, Inc., Logan, Utah) for three days prior to fusion, were centrifuged at 200 g for 5 minutes, and the pellet was washed twice as described above.

Spleen cells ($2 \times 10^8$) were combined with $4 \times 10^7$ NS-1 cells and centrifuged, and the supernatant was aspirated. The cell pellet was dislodged by tapping the tube, and 2 ml of 37° C. PEG 1500 (50% in 75 mM Hepes, pH 8.0) (Boehringer Mannheim) was added with stirring over the course of 1 minute, followed by the addition of 14 ml of serum-free RPMI over 7 minutes. An additional 16 ml RPMI was added and the cells were centrifuged at 200 g for 10 minutes. After discarding the supernatant, the pellet was resuspended in 200 ml RPMI containing 15% FBS, 100 μM sodium hypoxanthine, 0.4 μM aminopterin, 16 μM thymidine (HAT) (Gibco), 25 units/ml IL-6 (Boehringer Mannheim) and 1.5× $10^6$ thymocytes/ml and plated into 10 Corning flat-bottom 96-well tissue culture plates (Corning, Corning N.Y.).

On days 2, 4, and 6, after the fusion, 100 μl of medium was removed from the wells of the fusion plates and replaced with fresh medium. On day 8, Fusion 191 was screened by ELISA, testing for the presence of mouse IgG binding to MDC as follows. Immulon 4 plates (Dynatech, Cambridge, Mass.) were coated for 2 hours at 37° C. with 100 ng/well of MDC diluted in 25 mM Tris, pH 7.5. The coating solution was aspirated and 200 ul/well of blocking solution [0.5% fish skin gelatin (Sigma) diluted in CMF-PBS] was added and incubated for 30 min. at 37° C. The blocking solution was aspirated and 50 μl culture supernatant was added. After incubation at 37° C. for 30 minutes, and washing three times with PBS containing 0.05% Tween 20 (PBST), 50 μl of horseradish peroxidase conjugated goat anti-mouse IgG(fc) (Jackson ImmunoResearch, West Grove, Pa.) diluted 1:7000 in PBST was added. Plates were incubated as above, washed four times with PBST, and 100 μL substrate, consisting of 1 mg/ml o-phenylene diamine (Sigma) and 0.1 μl/ml 30% $H_2O_2$ in 100 mM Citrate, pH 4.5, was added. The color reaction was stopped after 5 minutes with the addition of 50 μl of 15% $H_2SO_4$. $A_{490}$ was read on a plate reader (Dynatech). Fusions 252 and 272 were screened in a similar manner, except ELISA plates were coated with 50 ng/well of MDC.

Selected fusion wells were cloned twice by dilution into 96-well plates and visually scored for the number of colonies/well after 5 days. The monoclonal antibodies produced by hybridomas were isotyped using the Isostrip system (Boehringer Mannheim, Indianapolis, Ind.).

Anti-MDC antibodies were characterized further by western blotting against recombinant MDC produced as described above in E. coli or mammalian CHO cells. To prepare the blot, approximately 3 μl of sedimented cells (transformed E. coli producing MDC; transfected CHO cells producing MDC; untransformed E. coli (control); and untransfected CHO cells (control)) were dissolved in standard sample preparation buffer containing SDS (sodium dodecyl sulfate) and DTT (dithiothreitol) (Sambrook et al.). After boiling, the lysates were fractionated via denaturing SDS-PAGE (18% acrylamide, Tris Glycine gel, NOVEX) and electroblotted to PVDF membranes (Millipore, Bedford, Mass.). MDC monoclonal antibodies were diluted to 0.7 μg/ml in PBS for use in the western blotting, following standard techniques (Sambrook et al.). As an additional control, the monoclonal antibodies were further tested for cross-reactivity on western blots of whole tissue lysates of human skin, tonsil, and thymus.

One anti-MDC monoclonal antibody, designated monoclonal antibody 191D, reacted strongly with recombinant MDC produced by both bacteria and mammalian cells. Further, this antibody displayed very little background reactivity in preliminary screening against bacteria, the CHO mammalian cell line, or the whole human tissues tested. In addition, this antibody showed the ability to immunoprecipitate recombinant CHO-derived MDC, following standard immunoprecipitation protocols (Sambrook et al.).

Some background reactivity was observed in subsequent western analyses using the anti-MDC monoclonal antibody 191D. Further anti-MDC monoclonal antibodies designated 252Y and 252Z (derived from Fusion 252), used at a concentration of 4 ug/ml, showed less background and strong reactivity with synthetic MDC at a concentration of 0.5 ng. No band was seen on the western blot with human tissue lysates of either colon, skin or tonsil, and background reactivity was minimal. The hybridomas that produce monoclonals 252Y and 252Z have been designated "hybridoma 252Y" and "hybridoma 252Z," respectively.

Monoclonal antibody 272D, at 1 μg/ml, recognized 200 ng of wild type MDC by western blot, although less strongly than antibody 252Y. Antibody 272D showed no background reactivity against lanes loaded with human thymus whole cell lysate or human skeletal muscle lysate.

The hybridoma cell line which produces monoclonal antibody 191D (designated hybridoma 191D) has been deposited with the American Type Culture Collection (ATCC), 10801 University Blvd., Manassas, Va. 20110-2209 (USA) pursuant to the provisions of the Budapest Treaty (ATCC Deposit date: Jun. 4, 1996; ATCC Accession No. HB-12122). The hybridoma cell lines that produce monoclonal antibodies 252Y and 252Z (designated "hybridoma 252Y" and "hybridoma 252Z") were also deposited with the ATCC pursuant to the provisions of the Budapest Treaty (ATCC Deposit date: Nov. 19, 1997; ATCC Accession Nos. HB-12433 and HB-12434, respectively). The hybridoma cell line that produces monoclonal antibody 272D was deposited with the ATCC pursuant to the provisions of the Budapest Treaty on Mar. 27, 1998 (ATCC Accession No. HB-12498). Availability of the deposited materials is not to be construed as a license to practice the invention in contravention of the rights granted under the authority of any government in accordance with its patent laws.

B. Polyclonal Antibodies.

Polyclonal antibodies against MDC were raised in rabbits following standard protocols (Sambrook et al.). Recombinant MDC produced as a GST fusion protein as described above was diluted in PBS, emulsified with Freund's Complete Adjuvant, and injected subcutaneously into rabbits. At intervals of three and six weeks, additional MDC diluted in PBS was emulsified with Freund's Incomplete Adjuvant and injected subcutaneously into the same rabbits. Ten days after the third immunization, serum was withdrawn from the rabbits and diluted ten-fold in Tris-buffered saline with 0.5% Tween 20 (TBS-T, Sambrook et al.) for characterization via western blotting against recombinant MDC as described above.

In a similar set of experiments, polyclonal antisera was generated in a rabbit against a 12-mer peptide corresponding to the amino-terminus of mature MDC (SEQ ID NO: 2, positions 1–12). The resultant antiserum was characterized in Western blot experiments using synthetic MDC (mature form, residues 1–69); MDC(0–69); MDC(9–69); MDC-eyfy; and MDC-wvas (see Example 11). The antiserum recognized all forms but the MDC(9–69) peptide.

C. MDC Detection Assay

Monoclonal antibodies 252Y and 252Z were employed in an MDC detection assay as follows: Aliquots of the antibodies 252Y and 252Z were biotinylated using NHS-LC-Biotin (Pierce) according to manufacturer's instructions. Immulon 4 ELISA plates were coated with one monoclonal antibody (252Y or 252Z, unbiotinylated) overnight at 4° C. The next day, the plates were blocked with 0.5% fish skin for 30 minutes at 37° C. Known quantities of MDC were loaded onto the plate for 30 minutes at 37° C. The plates were washed and coated with the other monoclonal antibody (biotinylated) for 30 minutes at 37° C. The plates were washed and loaded with streptavidin-HRP for 30 minutes at 37° C. The plates were then developed and read on a Dynatech MR5000 plate reader. Preliminary results indicate that, by using the antibody pair 252Y and 252Z, MDC is detectable in the concentration range of low nanograms to high picograms per milliliter.

In a related set of experiments, an ELISA format was employed to examine the relative affinity of antibodies 191D, 252Y, and 252Z for antigen. Antibodies were produced as ascites and purified over a protein A matrix (Prosep-A, Bioprocessing, LTD, Durham, England) according to manufacturer's instructions. Eluted antibody was dialyzed against PBS and antibody concentration was assessed by $A_{280}$ measurements. MDC was coated onto Immulon 4 plates in four-fold dilutions ranging from 2000 to 0.4 ng/ml. After blocking and washing the plates as described above, each antibody was added at a constant concentration of 250 ng/ml, and $A_{280}$ measurements were taken to quantify antibody bound to the plates. The absorbance values for antibodies 252Y and 252Z were more than five-fold higher than those of antibody 191D (1.86 and 1.90 versus 0.34) at 2000 ng/ml MDC; more than seven-fold higher (1.22, 1.29, and 0.16, respectively) at 500 ng/ml, and more than three-fold higher (0.47, 0.47, and 0.13) at 125 ng/ml MDC. At 31 ng/ml MDC, the $A_{280}$ measurements were at background levels for all three antibodies.

D. Characterization of Epitopes Recognized by Antibodies 252Y and 252Z

The ability of monoclonal antibodies 252Y and 252Z to recognize synthetic MDC (mature form, residues 1–69) and MDC variants (MDC(0–69); MDC(9–69); MDC-eyfy; and MDC-wvas (see Example 11)) was analyzed via Western blot. One hundred to 500 nanograms of each synthetic peptide was electrophoresed on a denaturing polyacrylamide gel, transferred, and probed with antibody 252Y or antibody 252Z at a concentration of 1 µg/ml. Immunoreactivity was visualized by incubating the probed blot with horseradish peroxidase-conjugated goat anti-mouse immunoglobulin G (Transduction Laboratories #M15345) at a concentration of 0.2 µg/ml or 1:5000 dilution in TRIS buffered saline with 0.1% Tween 20 (TBS Tw20) and 1% bovine serum albumin for 30 minutes at room temperature. The blot was washed three times in the TRIS buffered saline/0.1% Tween 20 solution and detection of antibody binding was measured by autoradiography (Kodak Hyperfilm) using electro-chemiluminescence (NEN Renaissance ECL # NEL 102). Both monoclonal antibodies were observed to recognize wildtype MDC and the analogs MDC(0–69), MDC(9–69), and MDC-eyfy. However, antibody 252Y and antibody 252Z both failed to recognize MDC-wvas, suggesting that the epitope(s) recognized by these antibodies include(s) the wv motif near the carboxyl-terminus of MDC. This motif tends to be highly conserved in all CC chemokines (see FIG. 1).

To further characterize the epitope(s) recognized by antibodies 252Y and 252Z, an Immulon 4 plate was coated with MDC at 1.0 µg/ml. After blocking the plate with fish skin as described above in part C, unlabeled antibody 252Y, 252Z, or an isotype-matched control was added at 5 µg/ml and incubated for 30 minutes at 37° C. Without washing, either biotinlyated antibody 252Y or 252Z was added at a concentration of 0.25 µg/ml, and the plate was incubated an additional 30 minutes at 37° C. Thereafter, the plate was washed and developed with streptavidin-HRP. The results showed that either 252Y or 252Z was capable of reducing the signal of either biotinylated antibody ten-fold, as compared with the signal of either biotinylated antibody blocked with the control antibody. These results further indicate that antibodies 252Y and 252Z recognize similar or overlapping epitopes.

In contrast, unpurified supernatant from hydriboma 272D was tested in a similar experiment for its ability to compete with biotynilated 252Y or biotynilated 252Z, but was unable to reduce the signal of either antibody. Thus, monoclonal antibody 272D recognizes an epitope different from that recognized by monoclonals 252Y and 252Z.

E. Antibodies 252Y and 252Z are Useful for Immunoprecipitating MDC

The following experiments were conducted which demonstrate a utility for antibodies 252Y and 252Z for immunoprecipitation of MDC. Antibodies 252Y, 252Z, and an irrelevant isotype-matched control were added separately at a concentration of 10 µg/ml to an extraction buffer (1% triton X-100, 10 mM Tris base, 5 mM EDTA, 10 mM NaCl, 30 mM Na pyrophospate, 50 mM NaF, 100 µM Na Orthovanadate, pH 7.6) containing 100 ng/ml MDC. These samples were incubated on ice for 1 hour. To precipitate the immune complexes, 15 µl of protein G sepharose (Pharmacia Biotech # 17-0618-01) were added to each sample and incubated on a rotation apparatus at 4° C. for 30 minutes. The samples were then centrifuged to collect the protein G sepharose/immune complexes, washed three times (1 ml each) in extraction buffer, boiled/solubilized in 2×SDS-PAGE buffer, electrophoresed on an 18% SDS-PAGE gel, and western blotted to PVDF membrane (Novex # LC2002). Nonspecific binding sites on the PVDF membrane were blocked with TBS Tw20/1% BSA for 30 minutes at room temperature. The blot was then probed with 1 µg/ml of antibody 252Y in TBS Tw20/1% BSA for 1 hour, washed three times with TBS Tw20, probed with horseradish peroxidase-conjugated goat anti-mouse 1gG in TBS Tw20/1% BSA for 30 minutes at room temperature, washed three times with TBS Tw20, and detected by autoradiography using ECL. Bands at approximately 8 kD were detected in the 252Y and 252Z lanes but not in the negative isotype-matched control lane. Additionally, MDC was immunprecipitated from cell culture supernatants containing RPMI (Rosell Park Memorial Institute—Gibco) medium with 10% fetal bovine serum spiked with 25 ng/ml MDC using the same conditions stated above.

F. Humanization of Anti-MDC Monoclonal Antibodies

The activities of MDC as reported herein suggest numerous therapeutic indications for MDC inhibitors (antagonists). MDC-neutralizing antibodies (see Example 30) comprise one class of therapeutics useful as MDC antagonists. Following are protocols to improve the utility of anti-MDC monoclonal antibodies as therapeutics in humans, by "humanizing" the monoclonal antibodies to improve their serum half-life and render them less immunogenic in human hosts (i.e., to prevent human antibody response to non-human anti-MDC antibodies).

The principles of humanization have been described in the literature and are facilitated by the modular arrangement of antibody proteins. To minimize the possibility of binding complement, a humanized antibody of the IgG4 isotype is preferred.

For example, a level of humanization is achieved by generating chimeric antibodies comprising the variable domains of non-human antibody proteins of interest with the constant domains of human antibody molecules. (See, e.g., Morrison and Oi, *Adv. Immunol.*, 44:65–92 (1989). The variable domains of MDC neutralizing anti-MDC antibodies are cloned from the genomic DNA of a B-cell hybridoma or from cDNA generated from mRNA isolated from the hybridoma of interest. The V region gene fragments are linked to exons encoding human antibody constant domains, and the resultant construct is expressed in suitable mammalian host cells (e.g., myeloma or CHO cells).

To achieve an even greater level of humanization, only those portions of the variable region gene fragments that encode antigen-binding complementarity determining regions ("CDR") of the non-human monoclonal antibody genes are cloned into human antibody sequences. [See, e.g., Jones et al., *Nature*, 321:522–525 (1986); Riechmann et al., *Nature*, 332:323–327 (1988); Verhoeyen et al., *Science*, 239:1534–36 (1988); and Tempest et al., *Bio/Technology*, 9:266–71 (1991). If necessary, the β-sheet framework of the human antibody surrounding the CDR3 regions also is modified to more closely mirror the three dimensional structure of the antigen-binding domain of the original monoclonal antibody. (See Kettleborough et al., *Protein Engin.*, 4:773–783 (1991); and Foote et al., *J. Mol. Biol.*, 224:487–499 (1992).)

In an alternative approach, the surface of a non-human monoclonal antibody of interest is humanized by altering selected surface residues of the non-human antibody, e.g., by site-directed mutagenesis, while retaining all of the interior and contacting residues of the non-human antibody. See Padlan, *Molecular Immunol.*, 28(4/5):489–98 (1991).

The foregoing approaches are employed using MDC-neutralizing anti-MDC monoclonal antibodies and the hybridomas that produce them, such as antibodies 252Y and 252Z, to generate humanized MDC-neutralizing antibodies useful as therapeutics to treat or palliate conditions wherein MDC expression is detrimental.

G. Human MDC-Neutralizing Antibodies from Phage Display

Human MDC-neutralizing antibodies are generated by phage display techniques such as those described in Aujame et al., *Human Antibodies*, 8(4):155–168 (1997); Hoogenboom, *TIBTECH*, 15:62–70 (1997); and Rader et al., *Curr. Opin. Biotechnol.*, 8:503–508 (1997), all of which are incorporated by reference. For example, antibody variable regions in the form of Fab fragments or linked single chain Fv fragments are fused to the amino terminus of filamentous phage minor coat protein pIII. Expression of the fusion protein and incorporation thereof into the mature phage coat results in phage particles that present an antibody on their surface and contain the genetic material encoding the antibody. A phage library comprising such constructs is expressed in bacteria, and the library is panned (screened) for MDC-specific phage-antibodies using labelled or immobilized MDC as antigen-probe.

H. Human MDC-Neutralizing Antibodies from Transgenic Mice

Human MDC-neutralizing antibodies are generated in transgenic mice essentially as described in Bruggemann and Neuberger, *Immunol. Today*, 17(8):391–97 (1996) and Bruggemann and Taussig, *Curr. Opin. Biotechnol.*, 8:455–58 (1997). Transgenic mice carrying human V-gene segments in germline configuration and that express these transgenes in their lymphoid tissue are immunized with an MDC composition using conventional immunization protocols. Hybridomas are generated using B cells from the immunized mice using conventional protocols and screened to identify hybridomas secreting anti-MDC human antibodies (e.g., as described above).

I. ELISA for Detecting and Monitoring Serum Concentrations of MDC

The measurement of endogenous levels of MDC is useful to monitor the immune state of a patient, especially a patient who is immunocompromised, in a hyperimmune state, or undergoing treatment with MDC neutralizing antibodies or other MDC antagonists.

A sensitive ELISA to measure MDC in biological fluids, for example serum, can be established using monoclonal antibodies, polyclonal antibodies, immuno-conjugates containing MDC ligands (for example heparin conjugates), or combinations thereof. For example, monoclonal antibodies 272D, 252Y and 252Z were employed in an MDC detection assay as described below.

Aliquots of the antibodies 252Y and 252Z were biotinylated using NHS-LC-Biotin (Pierce) according to manufacturer's instructions. Immulon 4 ELISA plates were coated with antibody 272D overnight at 4° C. The next day, the plates were blocked with 0.5% fish skin for 30 minutes at 37° C. Known quantities of MDC(1–69) were loaded onto the plate for 30 minutes at 37° C. The plates were washed and coated with either 252Y or 252Z (biotinylated) for 30 minutes at 37° C. The plates were washed and loaded with streptavidin-HRP for 30 minutes at 37° C. The plates were then developed and read on a Dynatech MR5000 plate reader. Preliminary results indicate that MDC is detectable in the concentration range of low nanograms per milliliter in this ELISA format. It is expected that use of polyclonal antibodies for the capture antibody will lead to a still more sensitive ELISA assay.

EXAMPLE 19

Calcium Flux Assay

Changes in intracellular calcium concentrations, indicative of cellular activation by chemokines, were monitored in several cell lines by an art-recognized calcium flux assay. Cells were incubated in 1 ml complete media containing 1 µM Fura-2/AM (Molecular Probes, Eugene, Oreg.) for 30 minutes at room temperature, washed once, and resuspended in D-PBS at ~$10^6$ cells/ml.

Two ml of suspended cells were placed in a continuously stirred cuvette at 37° C. in a fluorimeter (AMINCO-Bowman Series 2, Rochester, N.Y.). The concentration of intracellular calcium was indicated by fluorescence, which was monitored at 510 nm emission wavelength while switching between excitation wavelengths of 340 nm and 380 nm every 0.5 seconds. The ratio of the emissions from the 340 nm relative to the 380 nm excitation wavelengths corresponds to the level of intracellular calcium.

Cell lines measured by this assay included the following: the human embryonic kidney cell line HEK-293 stably transfected with the putative chemokine receptor gene V28 [Raport et al., *Gene*, 163:295–299 (1995)]; HEK-293 cells stably transfected with the chemokine receptor gene CCR5 [Samson et al., *Biochemistry*, 35:3362–3367 (1996); see also co-owned, co-pending U.S. patent application Ser. No. 08/575,967, filed Dec. 20, 1995, incorporated herein by reference, disclosing chemokine receptor materials and methods, including CCR5 (identified therein as "88C")], the human monocytic cell line THP-1, the human lung epithelial cell line A-549; and the human fibroblast cell line IMR-90. None of these cell lines fluxed calcium in response to the recombinant MDC protein. As positive controls, the HEK-293 transfectants responded strongly to thrombin, indicating that the assay was valid. In addition, the THP-1 cells responded strongly to the commercially available chemokines MCP-1 and MCP-3 (Peprotech, Rocky Hill, N.J.) at a final concentration of 25 ng/ml. No additional stimuli were tested on the A-549 or IMR-90 cell lines.

EXAMPLE 20

Inhibition of HIV Proliferation

Several CC chemokines have been implicated in suppressing the proliferation of Human Immunodeficiency Virus (HIV), the causative agent of human Acquired Immune Deficiency Syndrome (AIDS). See Cocchi et al., *Science*, 270:1811 (1995); Winkler et al., *Science*, 279: 389–393 (1998). The HIV antiproliferative activity of MDC is measured by means such as those described by Cocchi et al., in which a CD4$^+$ T cell line is acutely infected with an HIV strain and cultured in the presence of various concentrations of MDC. After three days, a fresh dilution of MDC in the culture medium is added to the cells. At 5 to 7 days following infection, the level of HIV is measured by testing the culture supernatants for the presence of HIV p24 antigen by a commercial ELISA test (Coulter, Miami, Fla.).

One technical report teaches that MDC possesses an HIV antiproliferative activity. See Pal et al., *Science*, 278: 695–698 (1997). The agent used in the study consisted of purified polypeptides that had been secreted from an immortalized cell line derived from CD8$^+$ T cells from an HIV-1-infected individual. Pal et al. reported that the purified "native MDC" from this cell line possessed an NH$_2$-terminus corresponding to the tyrosine at position 3 of SEQ ID NO: 1. A "minor" sequence beginning with the proline at position 2 of SEQ ID NO: 1 also was detected. The authors did not detect a peptide beginning with the glycine at position 1 of SEQ ID NO: 1 in their "native MDC" composition. According to Pal et al., a reversed-phase HPLC fraction containing the "native MDC" suppressed the acute infection of CD8$^+$ cell-depleted PBMCs by HIV-1$_{IIIB}$ and various NSI HIV isolates in a concentration-dependent fashion. Similar HIV suppressor activity was not observed in supernatants from other cell lines that appeared (from Northern blot studies) to demonstrate equivalent MDC gene expression.

A. Use of MDC Antagonists to Inhibit HIV Proliferation

An acute HIV-1$_{Bal}$ infectivity assay reported in Pal et al. was repeated (100 TCID$_{50}$ units/well) using the macrophage cell line PM-1 (1×$10^5$ cells/well) and using purified mature MDC recombinantly expressed in CHO cells and having an amino acid sequence beginning at position 1 of SEQ ID NO: 1 (see Example 10). Interestingly, mature MDC was found to have no HIV suppressive activity. The same assay was performed with MDC(0–69) (See Example 11), an analog that exhibits properties of a partial MDC antagonist (see Example 19) in that it binds CCR4 with wild-type affinity, but exhibits substantially reduced capacity to induce a calcium flux or induce chemotaxis. At a concentration of 1 µg/ml, MDC(0–69) conferred a 58% and 67% reduction in the production of infectious particles (TCID$_{50}$ units measured on days 5 and 7). The positive control RANTES produced greater than 95% inhibition at 5 ng/ml. Without intending to be limited to a particular theory, one explanation for these results is that mature MDC (1–69) induces HIV proliferation, and that the anti-proliferative effects of MDC(0–69) results from this species competitively inhibiting the capacity of endogenous mature MDC (1–69) to stimulate HIV-1 production.

The effects of mature MDC and of MDC-neutralizing antibodies were analyzed in Pal et al's acute HIV-1$_{BaL}$ (0.01 MOI/well) infectivity assay using peripheral blood mononuclear cells (PBMC, 1×$10^6$ cells/well) depleted of CD8$^+$ cells. The mature MDC (1–69) failed to inhibit p24 production, as compared to a control murine IgG1 antibody. However, the murine monoclonal anti-MDC neutralizing antibodies 252Y (IgG1) and 252Z each inhibited p24 production when tested separately at a concentration of 2 µg/ml (37% and 28% inhibition, respectively). Again, one explanation for these data is that PBMC contain and produce endogenous MDC (1–69) that acts to stimulate HIV-1 functions, and that MDC antagonists inhibit this effect.

To confirm the apparent role of MDC as an HIV-1 agonist, an infectivity assay (such as that described in Pal et al.) is repeated using MDC neutralizing antibody and titrating exogenous mature MDC(1–69) into the assay wells. If native MDC(1–69) exerts an agonistic effect on HIV-1 infectivity and/or proliferation, then it is expected that the antiviral effect of the neutralizing antibody will be reduced with increasing amounts of mature MDC, and will be overwhelmed with the addition of a molar excess of MDC.

Collectively, these results provide a therapeutic indication for MDC antagonists for inhibiting proliferation of infectious retroviruses, especially HIV retroviruses. Such therapeutic methods and uses are intended as an aspect of the invention. For use in this context, the term "MDC antagonist" includes any compound capable of inhibiting HIV-1 proliferation in a manner analogous to MDC neutralizing antibodies, or MDC(0–69), or MDC(3–69). For example, anti-MDC antibodies (especially neutralizing antibodies, and preferably humanized antibodies) are highly preferred MDC antagonists. Similarly, polypeptides that are capable of binding to MDC that comprise an antigen-binding fragment of an anti-MDC antibody are contemplated. Effective MDC analogs also are contemplated as MDC antagonists. For example, N-terminal deletion analogs of MDC are contemplated, especially deletion analogs having an amino acid sequence consisting of a portion of the amino acid sequence set forth in SEQ ID NO: 2 that is sufficient to bind to the chemokine receptor CCR4, the portion having an amino-terminus between residues 3 and 12 of SEQ ID NO: 2. Likewise, analogs comprising a chemical addition to the amino terminus to render said polypeptide antagonistic to MDC are contemplated. The chemical addition may be added to the amino terminus of MDC(1–69) to form the analog, or to the amino terminus of an MDC analog that has had amino acids deleted from its amino terminus (e.g., 1, 2, 3, 4, 5, 6, 7, 8, 9, 10, or 11 residues deleted).

Additional classes of MDC antagonists useful in anti-HIV therapeutic methods include antagonists derived from CCR4 or from other MDC receptors. For example, a solubilized, MDC-binding version of CCR4 or CCR4 fragment is contemplated. Similarly, humanized antibodies that block but do not signal through CCR4 are contemplated as useful as anti-HIV therapeutics. Such antibodies are made using techniques described herein for making anti-MDC antibodies and/or techniques that have been described in the art for generating antibodies to other seven transmembrane receptor proteins (e.g., using as an antigen CCR4-transfected cells that express CCR4 on their surface). See Wu et al., *J. Exp. Med.*, 185:1681–1691 (1997).

Yet another class of MDC antagonists useful in anti-HIV therapeutic methods of the invention include agents that have the effect of transforming mature MDC(1–69) to antagonist forms in vivo, e.g., by modifying the amino terminus of MDC. For example, administration of a therapeutically effective amount of the dipeptidyl aminopeptidase CD26 is contemplated.

Therapeutically effective amounts of MDC antagonists (i.e., for inhibiting HIV infectivity and/or proliferation) are readily determined using standard dose-response studies. Moreover, determination of proper dose and dosing is facilitated by anti-MDC antibodies of the invention (Example 18), which can be used in an ELISA or other standard assays to monitor serum MDC levels in subjects receiving treatment. A therapeutic MDC neutralizing antibody should be administered in sufficient quantity and with sufficient frequency so as to maintain serum concentrations of MDC below detectable levels. Doses of an MDC neutralizing antibody on the order of 0.1 to 100 mg antibody per kilogram body weight, and more preferably 1 to 10 mg/kg, are specifically contemplated. For humanized antibodies, which typically exhibit a long circulating half-life, dosing at intervals ranging from daily to every other month, and more preferably every week, or every other week, or every third week, are specifically contemplated. Use of an IgG4 type humanized MDC-neutralizing antibody is highly preferred, to minimize or eliminate the possibility of inducing a complement reaction.

Moreover, determination of therapeutically effective MDC antagonists, doses, and dosing schedules is facilitated by dose-response studies in art-recognized in vivo models for HIV infection and proliferation, such as studies in appropriate mice [Pettoello-Mantovani et al., *J. Infect. Diseases*, 177:337 (1998); J. M. McCune et al., "The Hematophtology of HIV-1 Disease: Experimental Analysis in vivo," in *Human Hematopoiesis in SCID Mice*, M. Roncarolo et al. (eds.), Landes Publishing Co., New York, N.Y., pp. 129–156 (1995); and McCune et al., "The SCID-hu mouse: a small animal model for HIV infection and antiviral testing," in *Progress in Immunol., Vol. VII*, Melchers et al. (eds.), Springer-Verlag Berlin-Heidelberg, pp. 1046–1049 (1989)] or primate models.

B. Use of TARC Antagonists to Inhibit HIV Proliferation

The foregoing experiments also suggest further analysis wherein an HIV-1 infectivity assay is repeated using neutralizing antibodies directed against other beta chemokines. For those β-chemokines lacking an activity towards $T_H2$ cells (analogous to MDC's activity toward such cells), it is expected that chemokine-specific neutralizing antibodies will behave much like the murine control IgG1 antibody above. However, for those β chemokines that possess an activity toward $T_H2$ cells that is comparable to that of MDC (i.e., TARC), it is expected that chemokine-specific neutralizing antibodies will behave much like MDC-neutralizing antibodies and inhibit HIV-1 infectivity and/or proliferation. The use of TARC-neutralizing antibodies and/or other TARC inhibitors to suppress the infectivity and/or proliferation of immunodeficiency viruses is specifically contemplated as an aspect of the invention.

The nucleotide and deduced amino acid sequences of TARC have been reported in the literature and are set forth herein in SEQ ID NOs: 42 and 43. See Imai et al., *J. Biol. Chem.* 271: 21514–21521 (1996); GENBANK ACCESSION NO. D43767. TARC polypeptides and anti-TARC antibodies are synthesized using procedures essentially as described herein for making MDC and anti-MDC antibodies, or using procedures described in the literature for TARC. [See Imai et al., *J. Biol. Chem.*, 272: 15036–15042 (1997); and Imai et al., *J. Biol. Chem.*, 271: 21514–21521 (1996).] The HIV-proliferative/anti-proliferative effects of TARC polypeptides (e.g., native mature TARC and TARC analogs, especially amino-terminal deletion and addition analogs) and TARC-neutralizing antibodies are assayed essentially as described in Pal et al. or Cocchi et al.

Based on the theory that the HIV antiproliferative efficacy of MDC antagonists is mediated by blocking the signaling of MDC through CCR4 in target cells that express CCR4, it is further contemplated that antibodies to any other chemokine that is known or is discovered to signal through CCR4 will be useful as anti-HIV therapeutics of the invention.

EXAMPLE 21

Effects of MDC on Fibroblast Proliferation

In addition to their ability to attract and activate leukocytes, some chemokines, such as IL-8, have been shown to be capable of affecting the proliferation of non-leukocytic cells [see Tuschil, *J. Invest. Dermatol.*, 99:294–298 (1992)]. Fibroblasts throughout the body are important to the structural integrity of most tissues. The proliferation of fibroblasts is essential to wound healing and response to injury but can be deleterious as well, as in the case of chronic inflammatory diseases, such as pulmonary fibrosis [Phan, in: *Immunology of Inflammation*, Elsevier (1983), pp. 121–162].

In vitro cell proliferation assays were utilized to assess the effects of MDC on the proliferation of fibroblasts. Human fibroblasts (CRL-1635) were obtained from ATCC and maintained in culture in DMEM with 10% FBS and 1% antibiotics. Proliferation assays were performed and quantitated as previously described in the art by Denholm and Phan, *Amer. J. Pathol.*, 134:355–363 (1989). Briefly, on day 1, $2.5 \times 10^3$ cells/well were plated into 96 well plates in DMEM with 10% FBS. Day 2: twenty-four hours after plating, medium on cells was changed to serum-free DMEM. Day 3: medium was removed from cells and replaced with MDC diluted in DMEM containing 0.4% FBS. Day 5: one microCurie of $^3$H-thymidine was added per well and incubation continued for an additional 5 hours. Cells were harvested onto glass fiber filters. Cell proliferation was expressed as cpm of $^3$H-thymidine incorporated into fibroblasts. Controls for this assay included the basal medium for this assay, DMEM with 0.4% FBS as the negative control, and DMEM with 10% FBS as the positive control.

Figure 7:
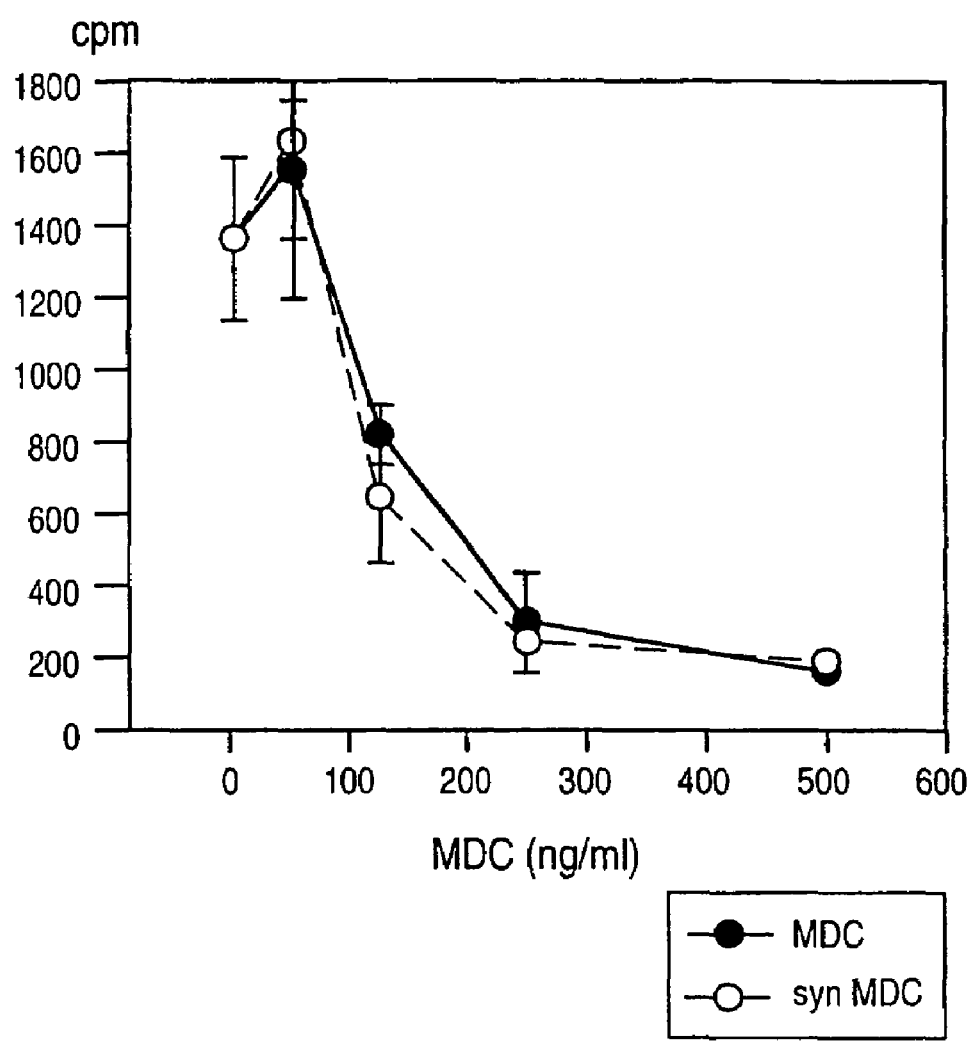

As shown in FIG. 7, MDC treatment decreased the proliferation of fibroblasts in a dose dependent manner. Similar inhibition of fibroblast proliferation was observed with both MDC purified from CHO cells (closed circles) and chemically synthesized MDC (open circles). The fibroblast-antiproliferative effect of MDC indicates a therapeutic utility for MDC in the treatment of diseases such as pulmonary fibrosis and tumors, in which enhanced or uncontrolled cell proliferation is a major feature.

EXAMPLE 22

Cell Proliferation Assays

The effects of MDC upon the proliferation of epithelial cells, T cells, fibroblasts, endothelial cells, macrophages, and tumor cells are assayed by methods known in the art, such as those described in Denholm et al., *Amer. J. Pathol.*, 134:355–363 (1989), and "In Vitro Assays of Lymphocyte Functions," in: *Current Protocols Immunology*, Sections 3–4, Wiley and Sons (1992), for the assay of growth factor activities. In these methods, enhancement or inhibition of cell growth and the release of growth factors are measured.

MDC effects on the proliferation of epithelial cells and endothelial cells are assayed using the same procedures as those described above for fibroblasts (Example 21).

The effects on the proliferation of T cells are determined using peripheral blood lymphocytes. Mononuclear cells are isolated from peripheral blood as described in Denholm et al., *Amer. J. Pathol.*, 135:571–580 (1989); cells are resuspended in RPMI with 10% FBS and incubated overnight in plastic tissue culture flasks. Lymphocytes remain in suspension in these cultures and are obtained by centrifugation of culture medium. One hundred thousand lymphocytes are plated into each well of a 96 well plate and incubated for three days in medium (RPMI plus 10% FBS) containing 1 μg/ml PHA with or without 50, 125, 250 or 500 ng/ml of MDC. One microCurie of $^3$H-thymidine is added during the last 18 hours of incubation. Cells are harvested and proliferations expressed as described for fibroblasts in Example 21.

The effects of MDC on macrophage proliferation are determined using elicited guinea pig peritoneal macrophages, obtained as described above in Example 13. Macrophages are plated into 96 well plates at a density of one hundred thousand cells per well in RPMI with 10% FBS, and incubated 2 hours to allow cells to adhere. Medium is then removed and replaced with fresh medium with or without 50, 125, 250 or 500 ng/ml of MDC. Cells with MDC are incubated three days, and proliferation is determined as described above for lymphocytes.

Chemokine-mediated control of the proliferation of these cell types has therapeutic implications in enhancing tissue repair following injury, and in limiting the proliferation of these cells in chronic inflammatory reactions such as psoriasis, fibrosis, and atherosclerosis, and in neoplastic conditions.

EXAMPLE 23

In Vivo Fibroblast Proliferation Assay

The anti-proliferative effects of MDC upon fibroblasts are determined in vivo by the methods known in the art, such as those reported by Phan and Fantone, *Amer. J. Pathol.*, 50:587–591 (1984), which utilize a rat model of pulmonary fibrosis in which the disease is induced by bleomycin. This model is well-characterized and allows for the assessment of fibroblast proliferation and collagen synthesis during all stages of this disease.

Briefly, rats are divided into four treatment groups: 1) controls, given intratracheal injections of normal saline; 2) saline-injected rats which also receive a daily intraperitoneal injection of 500 ng of MDC in saline; 3) bleomycin-treated, given an intratracheal injection of 1.5 mg/kg bleomycin (Calbiochem, Palo Alto, Calif.); and 4) bleomycin-treated rats which also are given a daily intraperitoneal injection of 500 ng of MDC.

Three rats per group are sacrificed at 4, 7, 14, 21, and 28 days after the initial intratracheal injections. Lungs are removed and samples of each lobe taken for histological examination and assays of collagen content.

EXAMPLE 24

MDC Chromosomal Localization

A 20 kb genomic fragment containing the human MDC gene was labelled with digoxigenin by nick translation and used as a probe for fluorescence in situ hybridization of human chromosomes (Genome Systems, Inc., St. Louis, Mo.). The labelled probe was hybridized to normal metaphase chromosomes derived from PHA-stimulated peripheral blood lymphocytes. Reactions were carried out in the presence of sheared human DNA in 50% formamide, 10% dextran sulfate, 30 mM sodium chloride, 3 mM sodium citrate, and 0.1% sodium dodecyl sulphate. Hybridization signals were detected by treating slides with fluoresceinated anti-digoxigenin antibodies, followed by counter-staining with 4,6-diamidino-2-phenylindole. An initial hybridization experiment localized the gene to the q terminus of a group E chromosome.

A genomic probe that specifically hybridizes to the short arm of chromosome 16 was used to demonstrate co-hybridization of chromosome 16 with the MDC probe. A total of 80 metaphase cells were analyzed with 61 exhibiting specific labeling. The MDC probe hybridized to a region immediately adjacent to the heterochromatic/euchromatic boundary, corresponding to band 16q13. The gene encoding TARC also is localized in this region. See Nomiyama et al., *Genomics*, 40: 211–213 (1997).

These chromosomal mapping data indicate a utility of MDC-encoding polynucleotides as a chromosomal marker. Contiguous fragments of SEQ ID NO: 1 of at least 15 nucleotides, and more preferably at least 20, 25, 50, 75, 100, 150, 200, 500, or more nucleotides, and the complements of such fragments, are specifically contemplated as probes of the invention. Moreover, probes having partial degeneracy from SEQ ID NO: 1 are contemplated as being useful as well. Probes having preferably at least 90%, and more preferably 95%, 96%, 97%, 98%, 99%, or more similarity to SEQ ID NO: 1 are preferred as probes of the invention.

EXAMPLE 25

MDC is a High-Affinity Ligand for CCR4

The chemokine receptor designated CCR4 has been characterized previously [Power et al., *J. Biol. Chem.,* 270: 19495–19500 (1995)], and shown to bind the CC chemokine TARC (Thymus and Activation-Regulated Chemokine, Genbank Accession No. D43767). See Imai et al., *J. Biol. Chem.,* 272: 15036–15042 (1997); and Imai et al., *J. Biol. Chem.,* 271: 21514–21521 (1996). The cDNA and deduced amino acid sequences of human CCR4 are set forth in SEQ ID NOs: 33 and 34, and are deposited with Genbank (Accession No. X85740). The following experiments were performed that demonstrate that MDC is a high affinity ligand for CCR4.

A. Preparation of CCR4-Transfected Cells

The murine pre-B cell line L1.2 [See, e.g., Gallatin et al., *Nature,* 304:30–34 (1983)] maintained in RPMI 1640 media supplemented with 10% fetal calf serum, was selected for transformation with the CCR4 expression vector described in Imai et al., *J. Biol. Chem.,* 272: 15036–15042 (1997), incorporated herein by reference. L1.2 cells were stably transfected as described previously by electroporation with 10 μg linearized plasmid at 260 V, 960 microfarads using a Gene Pulser (BioRad). See Imai et al., *J. Biol. Chem.,* 272: 15036–15042 (1997). It will be apparent that other cell lines in the art are suitable for CCR4 transfection for the following assays. For example, 293 cell lines have been transfected with CCR4 cDNA and employed effectively in calcium Flux assays.

B. Preparation of Recombinant Chemokines

The mature sequences of both MDC and TARC were chemically synthesized by Gryphon Sciences (South San Francisco Calif.) using t-butyl-oxycarbonyl chemistries on a peptide synthesizer (430A; Applied Biosystems). Lyophilized protein was dissolved at 10 mg/ml in 4 mM HCl and immediately diluted to 0.1 mg/ml in phosphate-buffered saline plus 0.1% bovine serum albumin (BSA) for storage at −80° C.

Recombinant MDC also was expressed as a fusion protein with the secreted form of placental alkaline phosphatase (SEAP) in the expression vector pcDNA3 (Clontech, Palo Alto Calif.). A similar TARC-SEAP fusion protein is described in Imai et al. (1997). Briefly, the coding region of MDC, followed by a sequence encoding a five amino acid linker (Ser-Arg-Ser-Ser-Gly), was fused in-frame to a sequence encoding mature SEAP, followed by a sequence encoding a (His)$_6$ tag. The MDC-SEAP expression plasmid was transfected into COS cells by the DEAE Dextran method. See Sambrook et al., *Molecular Cloning: A Laboratory Manual,* Cold Spring Harbor Laboratory, Cold Spring Harbor, N.Y. (1989). The transfected cells were cultured in Dulbecco's modified Eagle's medium supplemented with 10% fetal calf serum. Twenty-four hours after transfection, the serum levels were reduced from 10% to 1%. After 3–4 days, the culture supernatants were collected, centrifuged, filtered through a 0.45 micron membrane, and stored at 4° C. The concentration of MDC-SEAP in the filtered supernatant was determined by comparison with the reported specific activity of secreted placental alkaline phosphatase [Berger et al., *Gene,* 66: 1–10 (1988)], and confirmed using known concentrations of TARC-SEAP [Imai et al., (1997)] as an internal reference standard.

C. CCR4 Binding Assays

The MDC-SEAP was used as a probe to examine MDC binding to CCR4-transfected L1.2 cells. For displacement and saturation experiments, transfected L1.2 cells (approx. 3×10$^5$) were incubated for one hour at 16° C. in the presence of 0.5 nM MDC-SEAP in the presence or absence of various concentrations of unlabeled chemokines in 200 μl binding buffer (RPMI 1640 media containing 25 mM HEPES, pH 7.4, 1% BSA, and 0.02% sodium azide). Following incubation, the cells were washed four times in binding buffer and lysed in 50 μl of 10 mM Tris-HCl, pH 8.0, and 1% Triton X-100. Samples were heated at 65° C. for 15 minutes to inactivate cellular phosphatases, centrifuged, and stored at −20° C. until assayed.

Alkaline phosphatase activity in 10 μl of sample was determined by a chemiluminescence assay using the Great Escape Detection kit (Clontech, Palo Alto, Calif.) according to the manufacturer's instructions. The saturation binding curve was fitted (Table Curve™) using the Hill equation $y=a(x^c)/(x^c+b^c)$, where y is the amount of ligand bound, a is the maximum amount of ligand bound, x is the concentration of ligand, b is the concentration of ligand at which 50% of receptor sites are occupied ($K_D$), and c is the Hill coefficient. Binding competition curves were fitted (TableCurve™) using a three-parameter logistic model described by the equation $y=a/[1+(x/b)^c]$, where y is the amount of labelled ligand bound, a is the maximum amount of labelled ligand bound, x is the concentration of the competitive chemokine, b is the IC$_{50}$, and c is a parameter that determines the slope of the curve at the IC$_{50}$.

These binding assays demonstrated that MDC-SEAP bound to CCR4-expressing cells. This binding was to a single high affinity site with a $K_d$ of 0.18 nM, as demonstrated by Scatchard analysis. Binding of MDC-SEAP was competitively inhibited with increasing concentrations of unlabeled MDC or TARC. The IC$_{50}$ for MDC was 0.65 nM, while the IC$_{50}$ for TARC was 2.1 nM. These data suggest that both MDC and TARC recognize a common binding site on CCR4, and that MDC has more than three-fold higher affinity than TARC for CCR4.

To examine the specificity of MDC binding to CCR4, six additional chemokines (MCP-1, MCP-3, MCP-4, RANTES, MIP-1α, and MIP-1β) were tested for competition of MDC-SEAP binding. A 200-fold molar excess of each chemokine was tested for competition with a constant quantity of MDC-SEAP (0.5 nM). The additional chemokines did not compete for binding of MDC-SEAP to CCR4. In contrast, unlabeled MDC and TARC both blocked binding of MDC-SEAP to CCR4 transfectants.

D. Calcium Mobilization Assay

Imai et al. (1997) showed that TARC signals through CCR4 by inducing calcium mobilization. To determine the ability of MDC to cause signaling through chemokine receptors, we examined calcium mobilization in L1.2 cells recombinantly expressing CCR1, CCR2B, CCR3, CCR4, CCR5, CCR6, or CCR7.

Transfected L1.2 cells were suspended at a concentration of 3×10$^6$ cells/ml in Hank's balanced salt solution supplemented with 1 mg/ml BSA and 10 mM HEPES, pH 7.4. Cells were incubated with 1 μM fura-PE3-AM (Texas Fluorescence Labs) at room temperature for 1 hour in the dark. After washing twice, cells were resuspended at a concentration of 2.5×10$^6$ cells/ml. To measure intracellular calcium, 2 ml of cells were placed in a quartz cuvette in a Perkin- Elmer LS 50B spectrofluorimeter. Fluorescence was monitored at 340 nm (excitation wavelength 1), 380 nm (excitation wavelength 2), and 510 nm (emission wavelength) every 200 ms.

In these experiments, MDC did not cause calcium flux in L1.2 cells transfected with CCR1, CCR2B, CCR3, CCR5, CCR6, or CCR7, whereas each of these transfected cell lines responded to its known cognate ligand. In contrast, L1.2 cells transfected with CCR4 produced a strong calcium flux when stimulated with 10 nM MDC. Similar to other G protein-coupled receptors, CCR4 was refractory to subsequent stimulation with the same concentration of MDC. Ten nanomolar MDC also completely desensitized CCR4 transfectants to subsequent 10 nM TARC treatment. However, pre-treatment of CCR4-transfected L1.2 cells with TARC did not desensitize the receptor to subsequent stimulation with MDC. The signal produced by initial TARC stimulation was of lower intensity than both the primary MDC signal and the MDC signal secondary to TARC stimulation. These results further confirm that MDC is a ligand for CCR4.

E. Chemotaxis Assay

We next examined the ability of MDC and TARC to induce migration of CCR4-transfected L1.2 cells. Approximately $10^6$ CCR4-transfected L1.2 cells, resuspended in 0.1 ml RPMI 1640 media with 0.5% BSA, were loaded in the upper wells of a transwell chamber (3 μm pore size, Costar). Untransfected L1.2 cells were used as a control. Test chemokines were added to the lower wells at a concentration of 0–100 nM in a volume of 0.6 ml. After 4 hours at 37° C., cells in the lower chamber were collected and counted by FACS.

Both MDC and TARC induced migration of CCR4-transfected L1.2 cells. Both chemokines produced classic bell-shaped migration responses with maximal migration at about 10 nM. The migration observed with MDC was significantly higher than that for TARC, with MDC inducing migration of greater than 7% of input cells versus less than 3% migration for TARC. Untransfected L1.2 cells failed to migrate when treated with MDC. These chemotaxis results further confirm that both MDC and TARC are functional ligands for CCR4.

F. Conclusion

Collectively, the foregoing experiments provide compelling evidence that MDC acts as a high affinity ligand for the chemokine receptor CCR4.

As described below in Example 32, CCR4 has been found to be abundantly and nearly exclusively expressed on antigen-specific $T_H2$ helper T cells. Such cells are particularly susceptible to HIV-1 infection. (See Maggi et al., *Science*, 265:244–252 (1994).) The identification herein of a high affinity MDC receptor on HIV-susceptible T cells indicates a putative mechanism/pathway through which MDC(1–69) exerts its agonistic activity relating to enhanced HIV-1 infectivity and or viral production in infected cells (see Example 20), and likewise indicates a target for therapeutic intervention. Without intending to be limited to a particular theory, MDC-mediated activation of $T_H2$ cells, through the CCR4 receptor, is postulated to enhance infectivity and/or production of HIV-1 virus, in a manner analogous to the increased infectivity that has previously been observed for activated target cells. See Woods et al., *Blood*, 89:1635–1641 (1997); and Roederer et al., *J. Clin. Invest.*, 99(7): 1555–1564 (1997).

EXAMPLE 26

MDC Modulator Assays

Modulators of MDC activity may be useful for the treatment of diseases or symptoms of diseases wherein MDC plays a role. Such modulators may be either agonists or antagonists of MDC binding. The following receptor binding assays provide procedures for identifying such MDC modulators.

MDC is labelled with a detectable label such as $^{125}$I, $^3$H, $^{14}$C, biotin, or Europium. A preparation of cell membranes containing MDC receptors is prepared from natural cells that respond to MDC, such as human macrophages, phorbol ester-stimulated THP-1 cells, human fibroblasts, human fibroblast cell lines, or guinea pig macrophages. (Alternatively, a recombinant receptor preparation is made from cells transfected with an MDC receptor cDNA, such as a mammalian cell line transfected with a cDNA encoding CCR4 and expressing CCR4 on its surface.) The membrane preparation is exposed to $^{125}$I-labelled MDC, for example, and incubated under suitable conditions (e.g., ten minutes at 37° C.). The membranes, with any bound $^{125}$I-MDC, are then collected on a filter by vacuum filtration and washed to remove unbound $^{125}$I-MDC. The radioactivity associated with the bound MDC is then quantitated by subjecting the filters to liquid scintillation spectrophotometry.

The specificity of MDC binding may be confirmed by repeating the foregoing assay in the presence of increasing quantities of unlabeled MDC, and measuring the level of competition for binding to the receptor. These binding assays also can be employed to identify modulators of MDC receptor binding.

The foregoing receptor binding assay also may be performed with the following modification: in addition to labelled MDC, a potential MDC modulator is exposed to the membrane preparation. In this assay variation, an increased level (quantity) of membrane-associated label indicates the potential modulator is an activator of MDC binding; a decreased level (quantity) of membrane-associated label indicates the potential modulator is an inhibitor of MDC receptor binding. This assay can be utilized to identify specific activators and inhibitors of MDC binding from large libraries of chemical compounds or natural products. Rapid screening of multiple modulator candidate compounds simultaneously is specifically contemplated.

EXAMPLE 27

Assay to Identify Modulators of the MDC/CCR4 Interaction

The discovery that CCR4 acts as an MDC receptor prompted the development of the following additional assays to identify modulators of the interaction between MDC and CCR4. Such assays are intended as aspects of the present invention.

A. Direct Assay

In one embodiment, the invention comprehends a direct assay for modulation (potentiation or inhibition) of MDC-receptor binding. In one direct assay, membrane preparations presenting the chemokine receptor CCR4 in a functional conformation are exposed to either MDC alone or MDC in combination with potential modulators.

For suitable membrane preparations, tissue culture cells, such as 293 or K-562 cells (ATCC CRL-1573 and CCL-243, respectively), are transfected with an expression vehicle encoding the MDC receptor CCR4. Cells that express the receptor are selected and cultured, and a membrane preparation is made from the transfected cells expressing the chemokine receptor. By way of example, suitable membrane preparations are made by homogenizing cells in TEM buffer (25 mM Tris-HCl, pH 7.4, 1 mM EDTA, 6 mM $MgCl_2$, 10 µM PMSF, 1 µg/ml leupeptin). The homogenate is centrifuged at 800×g for 10 minutes. The resulting pellet is homogenized again in TEM and re-pelleted. The combined supernatants are then centrifuged at 100,000×g for one hour. The pellets containing the membrane preparations are resuspended in TEM at 1.5 mg/ml.

Membrane preparations are exposed to labelled MDC (e.g., MDC labelled with $I^{125}$ or other isotope, MDC prepared as an MDC-secreted alkaline phosphatase fusion protein, or MDC labelled in some other manner) either in the presence (experimental) or absence (control) of one or more compounds to be tested for the ability to modulate MDC-receptor binding activity. To practice the assay in standard 96-well plates, an exemplary reaction would include 2 µg of the membrane preparation, 0.06 nM of radio-labelled MDC, and 0.01 to 100 µM of one or more test compounds, in a reaction buffer comprising 50 mM HEPES, pH 7.4, 1 mM $CaCl_2$, 5 mM $MgCl_2$, and 0.1% BSA. The reactions are then incubated under suitable conditions (e.g., for 1–120 minutes, or more preferably 10–60 minutes, at a temperature from about room temperature to about 37° C.).

After incubation, the membranes, with any bound MDC and test compounds, are collected on a filter by vacuum filtration and washed to remove any unbound ligand and test compound. Thereafter, the amount of labelled MDC associated with the washed membrane preparation is quantified. In an embodiment wherein the label is a radioisotope, then bound MDC preferably is quantified by subjecting the filters to liquid scintillation spectrophotometry. In an embodiment wherein an MDC-alkaline phosphatase fusion protein is employed, alkaline phosphatase activity is measured using, for example, the "Great Escape" detection kit (Clontech, Palo Alto, Calif.) according to the manufacturer's instructions. The amount of label (e.g., scintillation counts or alkaline phosphatase activity) associated with the membranes is proportional to the amount of labelled MDC bound thereto. If the quantity of bound, labelled MDC observed in an experimental reaction is greater than the amount observed in the corresponding control, then the experimental reaction is scored as containing one or more putative agonists (i.e., activators, potentiators) of MDC receptor binding. If the quantity of bound, labelled MDC observed in an experimental reaction is less than the amount observed in the corresponding control, then the experimental reaction is scored as containing one or more putative antagonists (inhibitors) of MDC receptor binding.

The specificity of modulator binding may be confirmed by repeating the foregoing assay in the presence of increasing quantities of unlabeled test compound and noting the level of competition for binding to the receptor. The assay may also be repeated using labelled modulator compounds, to determine whether the modulator compound operates by binding with the MDC receptor.

B. Indirect GDP Assay

In another embodiment, the invention comprehends indirect assays for identifying modulations of MDC receptor binding that exploit the coupling of chemokine receptors to G proteins. As reviewed in Linder et al., *Sci. Am.*, 267: 56–65 (1992), during signal transduction, an activated receptor interacts with and activates a G protein. The G protein is activated by exchanging GDP for GTP. Subsequent hydrolysis of the G protein-bound GTP deactivates the G protein. Therefore, one can indirectly assay for G protein activity by monitoring the release of $^{32}P_i$ from $[\gamma-^{32}P]$-GTP.

For example, approximately $5\times10^7$ HEK-293 cells that have been transformed or transfected (e.g., with a CCR4 expression vector) to express CCR4 are grown in MEM+ 10% fetal calf serum (FCS). The growth medium is supplemented with 5 mCi/ml $[^{32}P]$-sodium phosphate for 2 hours to uniformly label nucleotide pools. The cells are subsequently washed in a low-phosphate isotonic buffer.

An experimental aliquot of washed cells is exposed to MDC in the presence of one or more test compounds, while a control aliquot of cells is exposed to MDC, but without exposure to the test compound. Following an incubation period (e.g., 10 minutes, 37° C.), cells are pelleted and lysed, and nucleotide compounds are fractionated using, e.g., thin layer chromatography (TLC) developed with 1 M LiCl. Labelled GTP and GDP are identified in the TLC by developing known GTP and GDP standards in parallel. The labelled GTP and GDP are then quantified by autoradiographic techniques that are standard in the art.

In this assay, the extent of MDC interaction with its receptor is proportional to the levels of $^{32}P$-labelled GDP that are observed, thereby permitting the identification of modulators of MDC-CCR4 binding. An intensified signal resulting from a relative increase in GTP hydrolysis, producing $^{32}P$-labelled GDP, indicates a relative increase in receptor activity. The intensified signal therefore identifies the potential modulator as an activator of MDC-CCR4 activity, or possibly as an MDC mimetic. Conversely, a diminished relative signal for $^{32}P$-labelled GDP, indicative of decreased receptor activity, identifies the potential modulator as an inhibitor of MDC receptor binding or an inhibitor of MDC-induced CCR4 signal transduction.

C. cAMP Assay

The activities of G protein effector molecules (e.g., adenylyl cyclase, phospholipase C, ion channels, and phosphodiesterases) are also amenable to assay. Assays for the activities of these effector molecules have been previously described. For example, adenylyl cyclase, which catalyzes the synthesis of cyclic adenosine monophosphate (cAMP), is activated by G proteins. Therefore, MDC binding and activation of CCR4 that activates a G protein, which in turn activates adenylyl cyclase, can be detected by monitoring cAMP levels in a host cell that recombinantly expresses CCR4.

Host cells that recombinantly express CCR4 are preferred for use in the assay. The host cells are incubated in the presence of either MDC alone or MDC plus one or more test compounds as described above. The cells are lysed, and the concentration of cAMP is measured by a suitable assay, such as a commercial enzyme immunoassay. For example, the BioTrak Kit (Amersham, Inc., Arlington Heights, Ill.) provides reagents for a suitable competitive immunoassay for cAMP.

An elevated level of intracellular cAMP in a test reaction relative to a control reaction is attributed to the presence of one or more test compounds that increase or mimic MDC-induced CCR4 activity, thereby identifying a potential activator compound. A relative reduction in the concentration of cAMP would indirectly identify an inhibitor of MDC-induced CCR4 activity.

It will be apparent to those in the art that the foregoing assays may be performed using MDC analogs described herein. Moreover, variations of the foregoing assays will be apparent to those in the art. Any variations that utilize both MDC and CCR4, and especially those variations which utilize MDC and cells that recombinantly express CCR4, are intended as aspects of the invention.

While the use of human MDC and CCR4 comprises a highly preferred embodiment, it will be apparent that the source organism for MDC and CCR4 is not a limiting factor, and the foregoing assays may be practiced effectively with MDC and/or with CCR4 that are derived from non-human organisms. By way of example, rat and mouse MDC are taught herein; and a *Mus musculus* chemokine receptor 4 sequence has been reported in the art. See Hoogewerf et al., *Biochem. Biophys. Res. Comm.,* 218(1): 337–343, and GenBank Accession No. X90862. Moreover, the methods used herein to obtain rat and mouse MDC are employable to obtain MDC or CCR4 from other organisms.

Moreover, evidence exists that there is at least one additional receptor that recognizes MDC. For example, MDC stimulates migration of dendritic cells and IL-2 activated natural killer cells. Godiska et al., *J. Exp. Med.,* 185: 1595–1604 (1997), incorporated herein by reference. This migration is not likely to be mediated by CCR4, since CCR4 appears to be expressed primarily on T cells, but not on monocytes or NK cells. See Imai et al. (1997). Consistent with this, CCR4 clones were represented very rarely in a human macrophage cDNA library (less than one in a million clones). Variations of the assays reported herein that utilize MDC with other MDC receptors also are intended as aspects of the invention.

Additionally, it will be apparent that the protocols described in preceding examples for assaying MDC biological activities (in vivo or with respect to specific cell types in vitro) are useful as assays for MDC modulators. In a highly preferred embodiment, a compound is first identified as a candidate MDC modulator using any of the assays described in Examples 26 and 27. Compounds that modulate MDC-receptor activity in one or more of these initial assays are further screened in any of the protocols described in preceding examples, to determine the ability of the compounds to modulate the MDC biological activities to which those examples specifically relate.

EXAMPLE 28

Non-Human Vertebrate MDC cDNAs and Proteins

A. Isolation of cDNA Encoding Rat and Mouse MDC Proteins

Knowledge of the human MDC gene sequence described herein was used as described below to isolate and clone putative rat and mouse MDC cDNAs, which are intended as aspects of the invention.

To clone a rat MDC cDNA, a labelled probe was prepared using standard random primer extension techniques. A fragment of the human MDC cDNA was generated by PCR, which fragment includes the MDC coding region plus approximately 300 bases of 3' untranslated sequence. This fragment was labelled with $^{32}$P-deoxyribonucleotides using the Random Primed DNA Labeling kit (Boehringer Mannhein, Indianapolis, Ind.). The labelled MDC probe was used to screen approximately $10^6$ bacteriophage lambda clones from a commercially-available rat thymus cDNA library (Stratagene, La Jolla, Calif., Cat. No. 936502). Three positive clones were obtained. Sequencing of one of the positive clones, designated RT3, provided an approximately 958 base pair sequence (SEQ ID NO: 37) that included an MDC open reading frame (SEQ ID NO: 38) and about 0.5 kb of 3' untranslated sequence. The open reading frame included sequence encoding the putative mature MDC protein (SEQ ID NO: 38, residues 1 to 69) plus 13 amino acids of the putative signal peptide sequence; it lacked the initiator methionine codon and sequence encoding the amino terminus of the signal peptide. A complete rat MDC cDNA or genomic clone is obtainable using all or a portion of the RT3 sequence as a labelled probe to re-probe the Stratagene rat cDNA library, and/or other rat cDNA libraries, and/or a rat genomic DNA library.

To clone a mouse MDC cDNA, approximately $10^6$ bacteriophage lambda clones of a commercially-available mouse thymus cDNA library (Stratagene, Cat. No. 935303) were screened with a radiolabeled fragment of the above-described rat MDC cDNA. The probe was generated using overlapping primers in a primer extension reaction. The primer extension reaction comprised: partially overlapping primers corresponding to nucleotides 41 to 164 of SEQ ID NO: 37 (and to nucleotides 92-215 of SEQ ID NO: 1); $^{32}$P-labelled deoxyribonucleotides; and the Klenow fragment of *E. coli* DNA polymerase. Twelve positive clones were isolated.

One positive clone, designated MT3, was sequenced and found to contain a 1.8 kb cDNA insert that included the entire putative murine MDC coding region and about 1507 bases of 3' untranslated sequence. The cDNA and deduced amino acid sequences for this murine MDC clone are set forth in SEQ ID NOs: 35 and 36, respectively. The mouse MDC has a putative 24 amino acid signal sequence followed by a 68 amino acid MDC sequence.

Comparisons of the human, rat, and mouse MDC protein and DNA (coding region) sequences reveal the following levels of similarity:

| | |
|---|---|
| Human vs. rat protein: | 65% identity; |
| Human vs. rat DNA: | 74% identity; |
| Human vs. mouse protein: | 64% identity; |
| Human vs. mouse DNA: | 72% identity; |
| Rat vs. mouse protein: | 88% identity; |
| Rat vs. mouse DNA: | 92% identity. |

The four cysteines characteristic of C—C chemokines are conserved in all three MDC proteins.

It is contemplated that the encoded rat and mouse MDC polypeptides corresponding to SEQ ID NOs: 38 and 36 are processed into mature mouse MDC proteins, in a manner analogous to the processing of the human MDC precursor, by cleavage of a signal peptide. The signal peptides for both human and murine MDC are 24 amino acids. The exact length of the rat MDC signal peptide will be readily apparent upon isolation of a full length rat MDC cDNA. It will be appreciated that these proteins can be synthesized recombinantly or synthetically and assayed for MDC biological activities as described herein for human MDC. Likewise, it will be appreciated that any analogs described herein for human MDC can be similarly prepared for these other mammalian MDC proteins.

The foregoing results demonstrate the utility of polynucleotides of the invention for identifying and isolating polynucleotides encoding other vertebrate MDC proteins, especially other mammalian or avian MDC proteins. Such identified and isolated polynucleotides, in turn, can be expressed (using procedures similar to those described in preceding examples) to produce recombinant polypeptides corresponding to other vertebrate forms of MDC, which proteins would be useful in the same manners that human MDC is useful, including therapeutic veterinary applications. Polynucleotides encoding vertebrate (and especially mammalian or avian) MDC proteins, the proteins themselves, and analogs thereof are all contemplated to be aspects of the present invention.

B. Synthesis of Murine MDC and Demonstration of Biological Activity

The interaction between murine MDC and human CCR4 was demonstrated using synthetic murine MDC in a chemotaxis assay. Murine L1.2 cells transfected with human CCR4 (Example 25) were tested to determine if such cells would migrate towards synthetic full-length mature murine MDC (SEQ ID NO: 36, residues 1 to 68) (Gryphon Sciences and Ian Clark-Lewis), and/or toward a synthetic murine MDC analog designated "Leu-MDC" which consists of a leucine residue attached to the amino terminus of mature murine MDC. (Murine Leu-MDC is thus analogous to "MDC(n+1)" described in Example 11. Costar Transwells with 3 µm filters were used for the assay.

Varying amounts of the synthetic MDC polypeptides (ten-fold dilutions from 10000 to 1 ng/ml final concentrations) were added to 600 µl RPMI/0.5% BSA (endotoxin-free) in the lower wells and $10^6$ cells in 100 µl RPMI/0.5% BSA (endotoxin-free) were added to the upper chambers. After incubating the transwells at 37° C. for 4 hours, the upper chambers were transferred to 500 µl ice-cold PBS/0.5 mM EDTA to release any migrated cells still clinging to the underside of the filter. Cells which had migrated to the lower chambers were harvested by combining the 600 µl medium from the lower chamber with the 500 µl PBS/EDTA for each well. Cells were centrifuged, resuspended in 200 µl of 1% formaldehyde, and then counted for 30 seconds on the FACSCAN (Becton-Dickinson).

The number of L1.2/huCCR4 cells that were observed to have migrated toward full-length mature murine MDC showed a characteristic dose-response curve, with chemotaxis observed at 1 ng/ml MDC and with peak chemotaxis occurring at 100 ng/ml murine MDC. The same number of cells migrated towards the 100 ng/ml full-lenght mature murine MDC from Gryphon Sciences and Ian Clark-Lewis, indicating that the two preparations had equivalent activity. The responses of L1.2/huCCR4 cells to murine Leu-MDC were approximately 20% lower than to full-length MDC.

C. Murine MDC Competes with Human MDC for Binding to Human CCR4.

In duplicate, $5 \times 10^5$ L1.2/huCCR4 cells were incubated with 0.1 nM $^{125}$I-labeled human mature MDC, alone or with unlabeled human mature MDC (10 nM or 100 nM), murine mature MDC (100 nM), or the the chemokine LARC (100 nM, control), for one hour in 200 µl binding buffer (50 mM HEPES, pH 7.5, 1 mM CaCl$_2$, 5 mM MgCl$_2$, 0.5% BSA, and 0.05% azide). Cells were spun down at slow speed and washed twice with binding buffer plus 0.5 M NaCl. Fifty microliters of scintillant fluid was added and samples were counted with a beta-counter. Unlabeled human and murine MDC both substantially reduced the amount of labeled MDC that bound to the CCR4-expressing cells (approx. 4000 cpm versus less than 500 cpm), with 100 nM murine MDC displaying a level of competition intermediate to that of 10 nM and 100 nM human MDC. The contol chemokine LARC (which specifically binds CCR6) diplayed substantially no competitive binding ability (approx. 3800 cpm).

The foregoing assay results demonstrate that a nonhuman form of MDC (murine MDC) is capable of binding and stimulating cells expressing a human MDC receptor. This data demonstrates an indication for vertebrate MDC, MDC fragments and analogs, and MDC modulators for human treatments and treatment formulations, as described elsewhere herein for human MDC, MDC fragments and analogs, and MDC modulators.

D. Macaque MDC cDNA and Polypeptide Sequences.

Polymerase chain reaction (PCR), using oligonucleotides designed from the human MDC cDNA as primers, was performed in order to amplify and isolate a cDNA encoding macaque MDC from a macaque thymus cDNA library. The macaque MDC amino acid sequence with secretory signal sequence is 93 amino acids and shares about 94% amino acid identity with human MDC. Referring to SEQ ID NO: 2, the macaque MDC amino acid sequence is identical to that of the human sequence, with the following variations: valine at position –18; phenylalanine at position –17; glycine at position –15; isoleucine at position –12; methionine at position 21; and serine at position 46. The macaque cDNA and deduced amino acid sequences are set forth in SEQ ID NOs: 45 and 46.

E. Use of Multiple Vertebrate MDC Sequences to Design MDC Analogs

The amino acid sequences for human, macaque, mouse, rat and/or other animals can be aligned using any alignment algorithm known in the art. Such an alignment will identify positions and regions within the MDC sequences that are highly conserved (e.g., that are identical in different species), moderately conserved (e.g., identical in some species with substitutions in other species of amino acids of similar character (e.g., acidic, basic, aliphatic, aromatic)), or variable (e.g., different in most or all species, including substitutions of amino acids of different character). Such an alignment provides significant guidance for the design of MDC analogs that will act as MDC mimetics as well as analogs that may act as MDC inhibitors. Substitution or deletion of variable residues is more likely to result in analogs that retain MDC biological activities, whereas highly conserved residues are targets for alteration or deletion to design analogs having different activities or having MDC inhibitory activity.

EXAMPLE 29

Receptor Binding and Stimulation Assays

Using procedures essentially as described in Example 25, selected MDC analogs described in Example 11 were screened for the ability to bind CCR4 and/or induce calcium (Ca$^{++}$) flux and chemotaxis in L1.2 cells transfected with CCR4.

The analog MDC(n+1) bound CCR4 with similar affinity to MDC, but induced calcium flux and chemotaxis in L1.2/CCR4 cells with a slightly lower potency than MDC. For example, in chemotaxis, the peak activity for MDC(n+1) was observed at 100 ng/ml rather than 10 ng/ml, and the maximum number of cells migrating was 5000, compared to 9000 for MDC.

MDC(9–69) bound CCR4 with reduced affinity relative to that of MDC (0–69). MDC(9–69) did not induce calcium flux in L1.2/CCR4 cells, and it was much less potent in chemotaxis. The fact that MDC(9–69) binds CCR4 but does not signal through CCR4 indicates a utility of MDC(9–69) as an MDC inhibitor.

Collectively, the activities of MDC (n+1) and MDC (9–69) indicate that amino-terminal additions and deletions and other modifications may result in useful MDC inhibitors.

The analog "MDC-wvas" bound CCR4 with ~500-fold less affinity than MDC, induced only a very small calcium flux, and did not induce any chemotaxis. The analog "MDC-eyfy" acted similar to MDC in CCR4-binding, chemotaxis, and calcium flux assays.

EXAMPLE 30

Monoclonal Antibodies 252Y & 252Z Inhibit CCR4-Mediated Cellular Responses to MDC Using procedures similar to those described in Example 25, the monoclonal antibodies 252Y and 252Z described in Example 18 were screened for the ability to modulate MDC-CCR4 binding and modulate the CCR4-mediated biological activities of MDC.

A. Antibodies 252Y and 252Z Inhibit MDC Binding to CCR4

Figure 11:
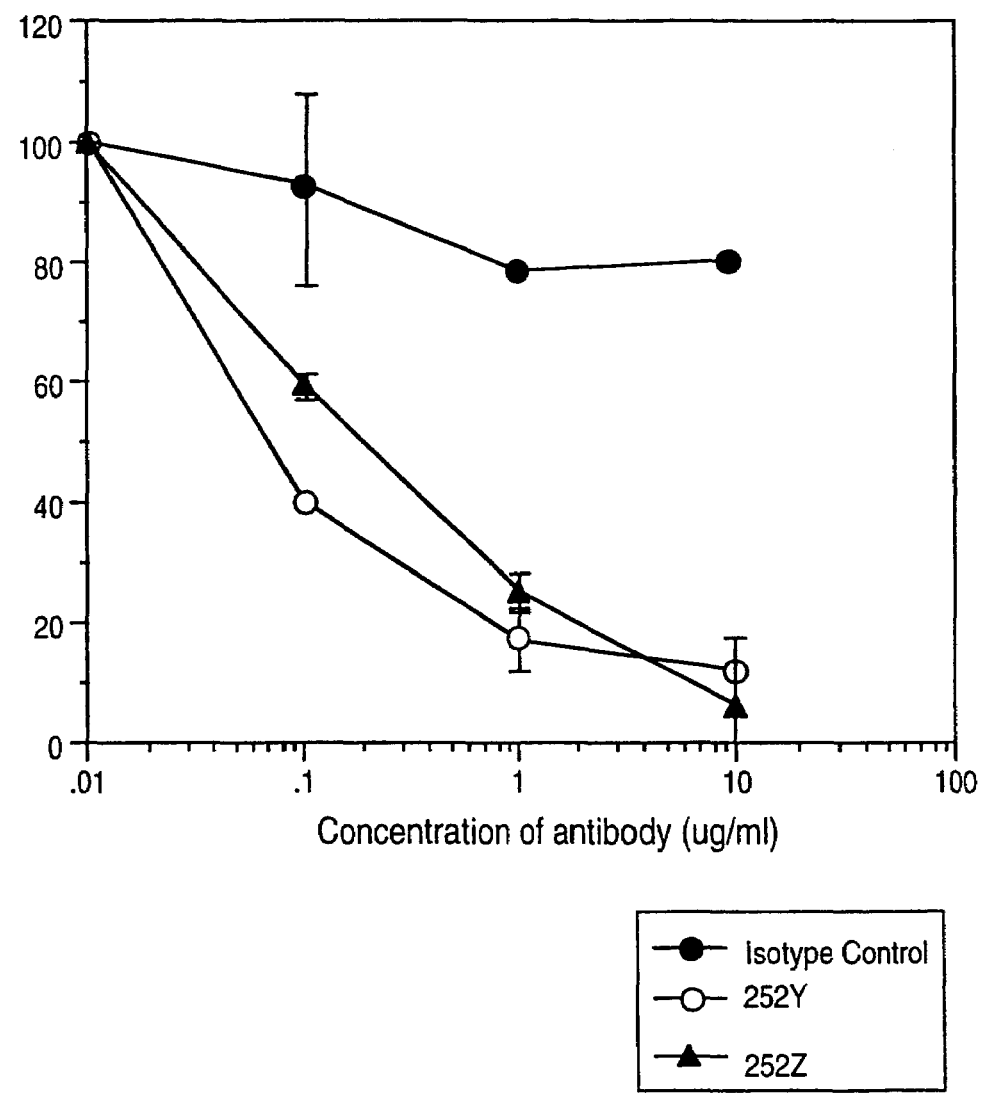
FIG. 11 depicts the inhibitory effects of the anti-MDC antibodies 252Y and 252Z on the binding of the fusion protein MDC-SEAP to the MDC receptor designated CCR4. Binding (depicted as percent of maximal binding) is plotted as a function of increased concentrations of antibody.

The fusion protein MDC-SEAP (Example 25) was employed to evaluate the ability of the antibodies to inhibit MDC binding to its receptor CCR4. MDC-SEAP at a concentration of 0.5 nM was incubated for fifteen minutes at room temperature with varying concentrations (0.01–10 μg/ml, shown in FIG. 11) of antibody 252Y, antibody 252Z, or an isotype control (final reaction volume 100 μl). Thereafter, the mixtures were added to CCR4-expressing L1.2 cells (100 μl, 4000 cells per μl), and incubated at 4° C. for an additional 60 minutes. The extent of MDC-SEAP binding to the CCR4-expressing cells was determined by alkaline phosphatase chemiluminescent assay as described in Example 25. A baseline level of non-specific binding (defined as the amount of binding that could not be competed by a 200-fold molar excess of native MDC) was determined and subtracted from experimental measurements. FIG. 11 presents the experimental results in graphical form, wherein each data point represents a percentage of maximum binding. (Maximum binding was defined as the amount of MDC-SEAP bound to the cells in the absence of antibody, minus non-specific binding.) As shown in FIG. 11, both antibody 252Y and antibody 252Z (but not the isotype control) inhibited MDC-SEAP binding to CCR4-infected cells in a dose-dependent manner. Fifty percent inhibition of binding was observed for both antibodies at an antibody concentration of about 2 μg/ml.

B. Antibodies 252Y and 252Z Inhibit MDC-Induced Chemotaxis

To confirm that antibodies 252Y and 252Z also were capable of inhibiting CCR4-mediated cellular responses to MDC, both calcium flux and chemotaxis assays were performed using the CCR4-transfected L1.2 cells.

For the calcium flux assay, the transfected L1.2 cells were labelled with Fura-2/AM (see Example 19) and monitored for $Ca^{++}$-induced fluorescence changes using an AMINCO-Bowman Series 2 fluorimeter. Addition of 75 nM MDC to the cells induced a rapid, transient increase in intracellular $Ca^{++}$ levels. This $Ca^{++}$ flux response was completely inhibited when either antibody 252Y or antibody 252Z were added to the cells at a concentration of 10 μg/ml one minute before contacting the cells with the MDC solution. An isotype-matched control antibody had no effect on the MDC-induced $Ca^{++}$ flux. Thus, both antibodies blocked the calcium flux response to MDC in CCR4-transfected L1.2 cells.

Figure 12:
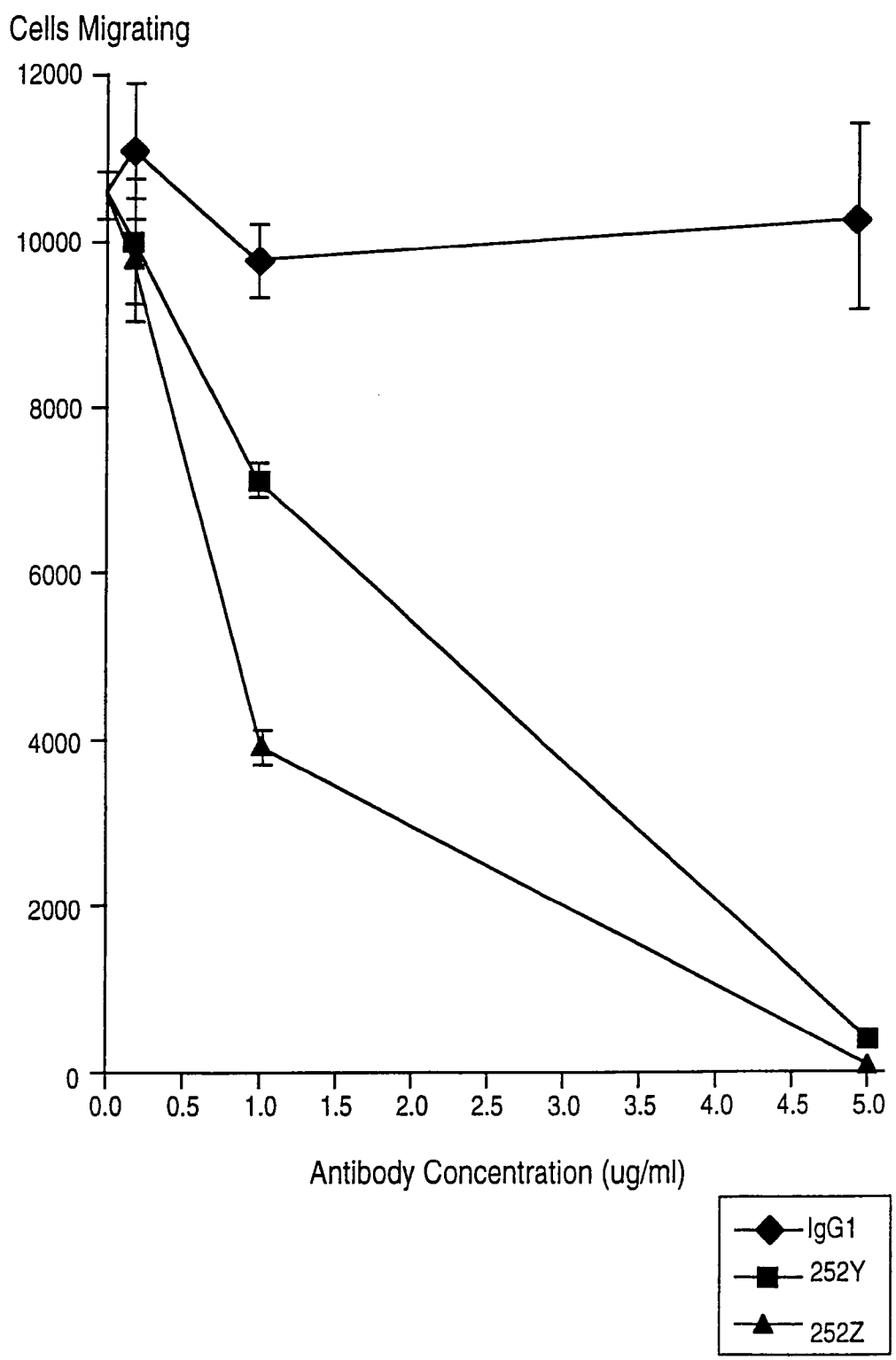
FIG. 12 depicts the inhibitory effects of the anti-MDC antibodies 252Y and 252Z on the MDC-induced chemotaxis of CCR4-transfected L1.2 cells. The number of cells observed migrating toward MDC in a standard chemotaxis assay are plotted as a function of increased concentrations of antibody.

For the chemotaxis assay, CCR4-transfected L1.2 cells (approx. 10 million cells/ml in a volume of 0.1 ml) were preincubated with antibody 252Y, antibody 252Z, or an isotype-matched control in RPMI-1640 media (Gibco) at various concentrations ranging from 0.5 to 50 μg/ml for 30 minutes at room temperature. Thereafter, the cells were exposed to 100 ng/ml MDC (i.e., the peak concentration for maximum chemotaxis) for 4 hours in a Costar Transwell apparatus. The number of cells migrating toward MDC was counted using a Becton-Dickinson FACScan apparatus. As shown in FIG. 12, MDC-induced chemotaxis of these cells was totally inhibited by either antibody 252Y or antibody 252Z at concentrations of 2–5 μg/ml, but not by the isotype-matched control. The $IC_{50}$ antibody concentration (required to inhibit 50% migration) was 1 μg/ml. The same antibodies did not inhibit chemotaxis of the CCR4/L1.2 cells toward the C—C chemokine TARC, indicating that the inhibitory effect was specific for MDC.

In a similar set of experiments, antibody 272D was screened for its ability to inhibit MDC stimulated chemotaxis. Ten μg/ml of antibody 272D was required to inhibit chemotaxis toward recombinant MDC (30 ng/ml) by greater than 90%. Only 2 μg/ml of antibody 252Z was required to achieve a similar level of inhibition, indicating that antibody 252Z is a more potent inhibitor of MDC induced chemotaxis.

EXAMPLE 31

MDC Induces Chemotaxis of $T_H2$ Helper T Cells

A transendothelial migration assay was performed essentially as described in the art [Ponath, et al., *J. Clin. Invest.*, 97: 604–612 (1996); Ponath et al., *J. Exp. Med.*, 183: 2437–2448 (1996); and Imai, et al., *Cell*, 91: 521–530 (1997)] to determine the presence and the phenotype of T cells that migrate toward the chemokines TARC and MDC. Briefly, about $2 \times 10^5$ cells of the endothelial cell line ECV304 (ATCC CRL-1998 or European Cell Culture Collection, Portions Down, UK) were added to Transwell inserts (Coaster) with a 5 μm pore size and cultured at 37° C. for 48–96 hours in M199 medium (GIBCO/BRL) supplemented with 10% FCS. Chemokines were diluted (serial dilutions of 0.1 to 100 nM) in a migration medium (a 1:1 mixture of RPMI-1640:M199, supplemented with 0.5% BSA, 20 mM HEPES, pH 7.4) and added to 24-well tissue culture plates in a final volume of 600 μl. Endothelial cell-coated inserts were placed in each well and $10^6$ peripheral blood mononuclear cells (PBMC) or T cell lines in 100 μl were added to the upper chambers. The cells were allowed to migrate through the endothelial cells into the lower chambers at 37° C. for 4 hours (PBMC) or 90 minutes (T cell lines). The migrated cells in the lower chambers were stained with FITC- or PE-conjugated monoclonal antibodies (mAb) for indicated cell surface makers and counted by flow cytometry.

In the transendothelial cell migration assay, both TARC and MDC induced dose-dependent vigorous migration of $CD14^-$ lymphocytes but not of $CD14^+$ monocytes, with MDC consistently inducing cell migration about 2 times more efficiently than TARC. Migration activity was detected with chemokine concentrations as low as 1 nM. Significant migration occurred with 10 nM TARC and 10 nM MDC. Analysis of the migrating lymphocytes revealed that 10 nM of either TARC or MDC attracted predominantly $CD4^+$ T cells. Neither TARC nor MDC induced migration of $CD19^+$ B cells or $CD16^+$ NK cells. Furthermore, TARC and MDC attracted almost exclusively $CD45RA^-/CD45RO^+$ effector/memory T cells. This observation was consistent with the observation that a murine (IgG) monoclonal antibody to CCR4 stained highly selectively a fraction (~20%) of $CD45RO^+CD4^+$ memory helper T cells.

Effector/memory helper T cells represent a population of cells that have encountered cognate antigens in vivo and have differentiated into $T_H1$ or $T_H2$ cells. Since CCR4 is expressed on about 20% of effector/memory helper T cells, additional experiments were conducted to determine whether CCR4 is selectively expressed on certain subsets of helper T cells.

First, $CD4^+CD45RO^+$ T cells (obtained from PBMC by negative selection with Dynabeads (Dynal) after incubation with anti-CD 16, anti-CD 14, anti-CD20, anti-CD8, and anti-CD45RA antibodies) were fractionated into $CCR4^+$ and $CCR4^-$ subpopulations by staining with the anti-CCR4 mAb and cell sorting. The cell subpopulations were expanded as polyclonal cell lines by culturing for 9–14 days at 37° C. in RPMI medium supplemented with PHA (diluted 1:100) and 100 U/ml IL-2. Expanded cells were subjected to a second round of enrichment by staining with anti-CCR4 monoclonal antibody and sorting. Sorted cells were immediately activated with 50 ng/ml PMA (Sigma) and 1000 ng/ml ionomycin (Sigma) for 24 hours, at which time the culture medium was analyzed by ELISA (R&D) to determine each population's pattern of cytokine production. Since helper T cells are classified into $T_H1$ and $T_H2$ subsets based on their profiles of cytokine production [Mosmann et al., *Immunol. Today*, 17: 138–146 (1996)], this analysis permitted determination of whether CCR4 is selectively expressed in one or the other subpopulation.

Analysis of the culture medium revealed that the $CCR4^+$ T cells produced significantly larger amounts of IL-4 and IL-5 than the cultured $CCR4^-$T cells (>12 ng/ml for $CCR4^+$ T cells versus <2.5 ng/ml for $CCR4^-$T cells for each cytokine). Conversely, $CCR4^-$ T cells produced IFN-γ at levels much higher than $CCR4^+$ T cells (>300 ng/ml vs. <25 ng/ml). These cytokine expression patterns indicate that the $CCR4^+$ population of cells contained almost exclusively $T_H2$ cells, whereas $CCR4^-$ cells were enriched for $T_H1$ cells.

To support the conclusion that $CCR4^+$ T cells are predominantly $T_H2$ cells, the $CD4^+CD45RO^+$ T cells that had been attracted by TARC or MDC in the transendothelial migration assay were expanded by culturing in PHA and IL-2 and then examined for their pattern of cytokine production as described above. Compared to total $CD4^+$ $CD45RO^+$ T cells, the cells attracted by TARC or MDC were enriched for producers of IL4 and IL-5 and depleted of producers of IFN-γ.

To further confirm the observed selective expression of CCR4 on $T_H2$ cells, experiments were performed to polarize $CD4^+CD45RA^+$ naive T cells in vitro, and the artificially polarized cell populations were examined for CCR4 expression. The naive T cells (obtained from PBMC by negative selection with Dynabeads after incubation with anti-CD 16, anti-CD 14, anti-CD 20, anti-CD8, and anti-CD45RO antibodies) were polarized into $T_H1$ cells by culturing in the presence of PHA (1:100), 2 ng/ml IL-12, and 200 ng/ml anti-IL-4 monoclonal antibodies (Pharmingen); or into $T_H2$ cells by culturing with PHA (1:100), 10 ng/ml IL-4, and 2 µg/ml anti-IL-12 monoclonal antibodies. After 3–4 days, 100 U/ml IL-2 was added to the cultures. CCR4 expression and transmigration were analyzed at day 9–14.

Analysis of the cultured cells with an anti-CCR4 monoclonal antibody revealed that 60% of cells polarized into $T_H2$ cells expressed CCR4, compared to only 4% of cells polarized into $T_H1$ cells. Northern blot analysis of the RNA isolated from these cell populations also demonstrated that $T_H2$ cells expressed CCR4 mRNA at levels much higher than $T_H1$ cells. As controls, CCR7 mRNA was expressed in both types of cells whereas CCR3 mRNA was not detected in either type of cell.

In the endothelial transmigration assay, the artificially polarized $T_H2$ cells, but not those polarized into $T_H1$, migrated vigorously toward TARC and MDC, whereas both types of cells migrated toward SLC. (See Nagira, et al., "Molecular cloning of a novel human CC chemokine secondary lymphoid-tissue chemokine that is a potent chemoattractant for lymphocytes and mapped to chromosome 9p13," *J. Biol. Chem.*, 272: 19518–19524 (1997).) Neither population of cells migrated toward eotaxin, a ligand for CCR3.

Collectively, the foregoing experiments demonstrate that a significant population of $T_H2$ cells express the chemokine receptor CCR4, and that the chemokines TARC and MDC represent selective chemoattractants of $T_H2$ cells, an effect that presumably is mediated at least in part through CCR4. Tissues of allergic inflammation are infiltrated by $T_H2$ cells, as well as by eosinophils, another cell type selectively attracted by MDC (see Example 12). Furthermore, T cells migrating into tissues after antigen challenge have been reported to be involved in localized production of the $T_H2$ cytokines, IL4 and IL-5, and in accumulation of eosinophils. (See Garlisi et al., *Clin. Immunol. Immunopathol.*, 75: 75–83 (1995).) Additionally, TARC and MDC are abundantly produced by dendritic cells whose close interactions with migrating lymphocytes constitute essential parts in initiation and promotion of immune responses. (See Steinman, R. M., *Annu. Rev. Immunol.*, 9: 271–296 (1991).) Enhanced TARC and MDC production from antigen presenting cells in $T_H2$ responses would be expected to lead to further recruitment of $T_H2$ cells via CCR4. Thus, the discoveries herein relating to the biological effects of MDC indicate that the effects may be deeply intertwined and involved in multiple aspects of an immunological or allergic cascade, a factor of direct clinical importance. For example, agents that interfere with the interactions of TARC or MDC with the receptor CCR4 (and/or that interfere with the interactions of TARC or MDC with $T_H2$ cells or eosinophils in cell-based assays) have therapeutic indications for reducing allergic inflammatory responses. The use of such agents in the treatment of asthma, a conditions characterized by eosinophilic infiltration and probable involvement of presentation of sensitizing antigen by mucosal dendritic cells to $T_H2$ T cells, is specifically contemplated.

EXAMPLE 32

Use of MDC and MDC Antagonists to Modulate Platelet Aggregation

The following experimental data indicates that MDC promotes platelet aggregation, and suggests a therapeutic indication for MDC and MDC antagonists to modulate platelet aggregation.

Female Lewis rats, six to eight weeks old, were administered 0.5 µg of synthetic mature human MDC(1–69) intravenously in a saline solution, via the tail vein. At various time points, the animals (4) were anesthetized with 100 µl ACE cocktail (Ketamine, ACE promazine and Rompon) and blood samples were collected into Microcontainers containing EDTA (Beckton Dickinson). Samples (300–400 µl) were stored overnight at 4–8° C. A CBC with Differential analysis was conducted to identify changes in cell number in the rats compared to control rats that had been administered only phosphate-buffered saline. In all four animals treated, marked platelet aggregation was observed. This aggregation was most pronounced at the time of MDC administration and dissipated with time after the bolus. A similar phenomenon was observed in mice using an analogous protocol.

Receptor analyses have indicated that platelets express detectable levels of the MDC receptor CCR4. These experiments suggest a receptor through which MDC may exert its platelet-aggregating effects.

The foregoing observations suggest that mature MDC stimulates platelet aggregation, and suggests that MDC antagonists are useful for inhibiting coagulation. Such use is indicated, e.g., in myocardial infarction patients to prevent further inappropriate blood clotting, and in patients for the therapeutic or prophylactic treatment of stroke.

The concentrations at which MDC induces platelet aggregation and at which MDC antagonists prevent platelet aggregation are determined in vitro using purified platelets and serial dilutions of MDC and MDC antagonists and procedures that are well known in the art. See, e.g., Jeske et al., *Thromb. Res.*, 88(3):271–281 (1997); Herault et al., *Thromb. Haemost.*, 79(2):383–388 (1998); and Furakawa et al., *Jpn. J. Pharmacol.*, 75(3):295–298 (1997). Putative MDC antagonists for screening in such assays include all of the putative MDC antagonists identified above, e.g., in Example 20. Those MDC analogs that inhibit platelet aggregation and those that promote aggregation are determined by such dose response studies and/or by mouse studies as described above.

Similarly, since TARC also signals through CCR4, the use of TARC and TARC antagonists to modulate platelet aggregation also is intended as an aspect of the invention.

EXAMPLE 33

Use of an MDC Antagonist to Modulate an Immune Response in a Mammalian Host

The following procedures are performed to demonstrate that MDC antagonists, such as MDC neutralizing antibodies, are capable of modulating an immune respone in a mammalian host.

A. Antigen-Induced Asthma Model

Laboratory animals (e.g., Balb/C mice) are challenged with ovalbumin using the following regimen: Day 0: 100 μg ovalbumin (Sigma), 4.5 mg alum (Imject®, Pierce), administered by 200 μl intraperitoneal injection; Day 14: 100 μg ovalbumin, 4.5 mg alum administered by 200 μl intraperitoneal injection, plus 100 μg ovalbumin in 50 μl saline, administered intra-nasally; days 25, 26, and 27: 50 μg ovalbumin in 50 μl saline, administered intra-nasally. As a contol, saline is administered to animals in lieu of ovalbumin. To test the effect of a putative MDC modulator (such as an MDC-neutralizing antibody) on the animal's allergic-type response to the ovalbumin, the modulator (or a control, e.g., saline) is administered to test animals intraperitoneally on days 25, 26, and 27, one hour prior to challenge with ovalbumin. Exemplary dosing of an anti-MDC antibody is 0.1 to 5 mg/kg body weight.

On day 28, the mice are sacrificed, blood is collected, and bronchioalveolar lavage is performed. Cells from the lavage fluid are collected and counted, and a white blood cell differential is performed. Reduction in eosinophils and/or neutrophils in the lavage fluid of treated animal versus contol animals is indicative of the therapeutic efficacy of the MDC antagonist treatment. Reduction in anti-ovalbumin antibodies (especially IgE antibodies) in the blood (assayed by ELISA, for example) is further indicative of the therapeutic efficacy of the MDC antagonist.

B. Modulation of a $T_H2$ Response

To demonstrate the ability of an MDC antagonist to suppress an immune response, laboratory animals are immunized subcutaneously or intraperitoneally with a suitable antigen, such as ovalbumin or tetanus toxoid, or with a saline control. Aluminum hydroxide (alum), which preferentially promotes a $T_H2$ response, or Freund's complete adjuvant, which tends to drive a $T_H1$ response, are used as adjuvants in some of the animals. Animals are immunized on day 0 (e.g., with 100 μg ovalbumin+4.5 mg alum), followed by booster immunizations at, e.g., days 14 and 28. The antibody titer against the selected antigen is permitted to drop to normal levels in the animals, e.g., for 1–2 months, monitored via ELISA.

After antibody levels have dropped to normal, the animals are re-challenged with the selected antigen. An MDC antagonist, such as an MDC-neutralizing antibody, is administered contemporaneously with the antigen, two, six, and/or twenty-four hours later. One week later, blood from the animals is drawn, white blood cells are analyzed, and antibodies to the antigen are titered and isotyped. Reduced levels of $IgG_1$ antibody, IgE antibody, and $T_H2$ cells in the treated animals versus the control animals is indicative of a therapeutically effective MDC antagonist, where immunosuppression is desired. A more pronounced the therapeutic effect in the alum-administered animals than the animals injected with Freund's aduvant is expected.

C. Murine Lupus Model The therapeutic efficacy of an MDC antagonist for the treatment of lupus erythematosus is demonstrated in animal models, such as NZB/NZW F1 mice, that are known in the art and have been described in the literature. See, e.g., Wofsy, D. et al., *J. Immunol.*, 138(10): 3247–3253 (May, 1987); and Daikh et al., *J. Immunol.*, 159(7): 3104–3108 (October, 1997).

D. Use of an MDC Antagonist to Treat Human Lupus Erythematosus

An MDC antagonist such as a humanized or human anti-MDC antibody or anti-CCR4 antibody is employed in a standard dose-escalation study to demonstrate efficacy in the treatment of lupus erythematosus in affected human individuals. Exemplary dosing regimens for an antibody range from 0.01 to 50 mg/kg body weight, and preferably 0.1 to 5 mg/kg, administered weekly, or bi-weekly, or monthly. Treatment efficacy is determined by monitoring standard indices. See, e.g., Bombardier et al., "Derivation of the SLEDAI: a disease activity index for lupus patients," *Arthritis Rheum*, 35: 630–640 (1992); Liang et al., "Measurement of systemic lupus erythematosus activity in clinical research," *Arthritis Rheum.*, 31: 817–825 (1988). Optimal dosing is determined by standard dose-response studies after efficacy is demonstrated.

E. Use of an MDC Antagonist to Treat Human Multiple Sclerosis

An MDC antagonist such as a humanized or human anti-MDC antibody or anti-CCR4 antibody is employed in a standard dose-escalation study to demonstrate efficacy in the treatment of multiple sclerosis in affected human individuals. Exemplary dosing regimens for an antibody-based therapeutic are as set forth in Seciton D, above. Treatment efficacy is determined by monitoring standard MS indices. See, e.g., Kurtzke, J. F., "Rating neurologic impairment in multiple sclerosis: An expanded disability status scale (EDSS)," *Neurology*, 33: 1444 (1983).

The biological functions of MDC, elucidated as described above, suggest several clinical applications.

Chemokines in general attract and activate monocytes and macrophages (Baggiolini et al., supra), and MDC in particular attracts macrophages and inhibits monocyte chemotaxis. Thus, MDC expression in a pathogenic inflammatory setting may exacerbate disease states by recruiting additional macrophages or other leukocytes to the disease site, by activating the leukocytes that are already there, or by inducing leukocytes to remain at the site. Thus, inhibiting the chemoattractant activity of MDC may be expected to alleviate deleterious inflammatory processes. Significantly, the potential benefits of such an approach have been directly demonstrated in experiments involving IL-8, a C-X-C chemokine that attracts and activates neutrophils. Antibodies directed against IL-8 have a profound ability to inhibit inflammatory disease mediated by neutrophils [Harada et al., J. Leukoc. Biol., 56:559 (1994)]. Inhibition of MDC is expected to have a similar effect in diseases in which macrophages are presumed to play a role, e.g., Crohn's disease, rheumatoid arthritis, or atherosclerosis.

Alternatively, augmenting the effect of MDC may have a beneficial role in such diseases, as chemokines have also been shown to have a positive effect in wound healing and angiogenesis. Thus, exogenous MDC or MDC agonists may be beneficial in promoting recovery from such diseases.

In addition, the myelosuppressive effect demonstrated for the C—C chemokine MIP-1α (Maze et al., supra) suggests that MDC may have a similar activity. Such activity, provided by MDC or MDC agonists, may yield substantial benefits for patients receiving chemotherapy or radiation therapy, reducing the deleterious effects of the therapy on the patient's myeloid progenitor cells.

MDC or MDC agonists may also prove to be clinically important in the treatment of tumors, as suggested by the ability of the C—C chemokine TCA3 to inhibit tumor formation in mice (see Laning et al., supra). MDC may act directly or indirectly to inhibit tumor formation, e.g., by attracting and activating various non-specific effector cells to the tumor site or by stimulating a specific anti-tumor immunity. The fibroblast-antiproliferative effect of MDC indicates a therapeutic utility for MDC in the treatment of diseases such as pulmonary fibrosis and tumors, in which enhanced or uncontrolled cell proliferation is a major feature.

While the present invention has been described in terms of specific embodiments, it is understood that variations and modifications will occur to those skilled in the art. Accordingly, only such limitations as appear in the appended claims should be placed on the invention.

The invention claimed is:

1. A method of palliating an allergic reaction in a mammalian subject, comprising the steps of:

identifying a mammalian subject in need of treatment for an allergic reaction that is characterized by eosinophil accumulation, and administering to said mammalian subject a composition comprising an MDC antagonist in an amount effective to palliate the allergic reaction; wherein the MDC antagonist comprises an antibody or antigen-binding fragment thereof that specifically binds to a mammalian MDC polypeptide.

2. The method according to claim 1 wherein the MDC antagonist is selected from the group consisting of:

(a) an antibody that specifically binds to a mammalian MDC polypeptide;

(b) a polypeptide that specifically binds to a mammalian MDC polypeptide and comprises an antigen-binding fragment of an anti-MDC antibody of (a); and (c) combinations of (a) and (b).

3. The method according to claim 1 wherein said antibody or antigen-binding fragment thereof is selected from the group consisting of monoclonal antibodies, polyclonal antibodies, single chain antibodies, chimeric antibodies, and humanized antibodies.

4. The method according to claim 1 wherein the MDC antagonist is a monoclonal antibody.

5. The method according to claim 1, wherein the MDC antagonist is a polypeptide that specifically binds to a mammalian MDC polypeptide and comprises an antigen-binding fragment of an antibody that specifically binds to a mammalian MDC polypeptide.

6. The method according to claim 4, wherein the monoclonal antibody is selected from the group consisting of 191D (produced by a hybridoma with ATCC Accession No. HB-12122), 252Y (produced by a hybridoma with ATCC Accession No. HB-12433), 252Z (produced by a hybridoma with ATCC Accession No. HB-12434), and 272D (produced by a hybridoma with ATCC Accession No. HB-12498).

7. The method according to claim 1, wherein the antibody or antigen-binding fragment thereof specifically binds to a human MDC polypeptide.

8. The method according to claim 1, wherein the antibody or antigen-binding fragment thereof is a humanized antibody or humanized antibody fragment.

* * * * *

SEQUENCE LISTING

```
<160> NUMBER OF SEQ ID NOS: 46

<210> SEQ ID NO 1
<211> LENGTH: 2923
<212> TYPE: DNA
<213> ORGANISM: Homo sapiens - human MDC cDNA
<220> FEATURE:
<221> NAME/KEY: CDS
<222> LOCATION: (20)..(298)
<221> NAME/KEY: mat_peptide
<222> LOCATION: (92)..(298)

<400> SEQUENCE: 1
gagacataca ggacagagc atg gct cgc cta cag act gca ctc ctg gtt gtc      52
                    Met Ala Arg Leu Gln Thr Ala Leu Leu Val Val
                                   -20                    -15 ctc gtc ctc ctt gct gtg gcg ctt caa gca act gag gca ggc ccc tac     100
Leu Val Leu Leu Ala Val Ala Leu Gln Ala Thr Glu Ala Gly Pro Tyr
            -10                  -5                    1 ggc gcc aac atg gaa gac agc gtc tgc tgc cgt gat tac gtc cgt tac     148
Gly Ala Asn Met Glu Asp Ser Val Cys Cys Arg Asp Tyr Val Arg Tyr
     5                   10                      15 cgt ctg ccc ctg cgc gtg gtg aaa cac ttc tac tgg acc tca gac tcc     196
Arg Leu Pro Leu Arg Val Val Lys His Phe Tyr Trp Thr Ser Asp Ser
 20                  25                      30                  35 tgc ccg agg cct ggc gtg gtg ttg cta acc ttc agg gat aag gag atc     244
Cys Pro Arg Pro Gly Val Val Leu Leu Thr Phe Arg Asp Lys Glu Ile
                 40                  45                  50 tgt gcc gat ccc aga gtg ccc tgg gtg aag atg att ctc aat aag ctg     292
Cys Ala Asp Pro Arg Val Pro Trp Val Lys Met Ile Leu Asn Lys Leu
             55                  60                  65 agc caa tgaagagcct actctgatga ccgtggcctt ggctcctcca ggaaggctca      348
Ser Gln ggagccctac ctccctgcca ttatagctgc tccccgccag aagcctgtgc caactctctg   408
cattccctga tctccatccc tgtggctgtc acccttggtc acctccgtgc tgtcactgcc   468
```

```
atctccccc  tgaccctct   aacccatcct  ctgcctccct  ccctgcagtc  agagggtcct   528
gttcccatca  gcgattcccc  tgcttaaacc  cttccatgac  tccccactgc  cctaagctga   588
ggtcagtctc  ccaagcctgg  catgtggccc  tctggatctg  ggttccatct  ctgtctccag   648
cctgcccact  tcccttcatg  aatgttgggt  tctagctccc  tgttctccaa  acccatacta   708
cacatcccac  ttctgggtct  tgcctggga   tgttgctgac  actcagaaag  tcccaccacc   768
tgcacatgtg  tagccccacc  agccctccaa  ggcattgctc  cccaagcag   ctggtaattc   828 catttcatgt  attagatgtc  ccctggcccct  ctgtcccctc  ttaataaccc  tagtcacagt   888
ctccgcagat  tcttgggatt  tgggggtttt  ctcccccacc  tctccactag  ttggaccaag   948
gtttctagct  aagttactct  agtctccaag  cctctagcat  agagcactgc  agacaggccc  1008
tggctcagaa  tcagagccca  gaaagtggct  gcagacaaaa  tcaataaaac  taatgtccct  1068
cccctctccc  tgccaaaagg  cagttacata  tcaatacaga  gactcaaggt  cactagaaat  1128
gggccagctg  ggtcaatgtg  aagccccaaa  tttgcccaga  ttcacctttc  ttcccccact  1188
cccttttttt  ttttttttt   tttgagatgg  agtttcgctc  ttgtcaccca  cgctggagtg  1248
caatggtgtg  gtcttggctt  attgaagcct  ctgcctcctg  ggttcaagtg  attctcttgc  1308
ctcagcctcc  tgagtagctg  ggattacagg  ttcctgctac  cacgcccagc  taatttttgt  1368 attttagta   gagacgaggc  ttcaccatgt  tggccaggct  ggtctcgaac  tcctgtcctc  1428
aggtaatccg  cccacctcag  cctcccaaag  tgctgggatt  acaggcgtga  gccacagtgc  1488
ctggcctctt  ccctctcccc  actgccccc   ccaacttttt  tttttttttt  atggcagggt  1548
ctcactctgt  cgcccaggct  ggagtgcagt  ggcgtgatct  cggctcacta  caacctcgac  1608
ctcctgggtt  caagtgattc  tcccaccca   gcctcccaag  tagctgggat  tacaggtgtg  1668
tgccactacg  gctggctaat  ttttgtattt  ttagtagaga  caggtttcac  catattggcc  1728
aggctggtct  tgaactcctg  acctcaagtg  atccaccttc  cttgtgctcc  caaagtgctg  1788
agattacagg  cgtgagctat  cacacccagc  ctcccccttt  ttttcctaat  aggagactcc  1848
tgtacctttc  ttcgttttac  ctatgtgtcg  tgtctgctta  catttccttc  tcccctcagg  1908 cttttttttgg  gtggtcctcc  aacctccaat  acccaggcct  ggcctcttca  gagtacccc   1968 cattccactt  tccctgcctc  cttccttaaa  tagctgacaa  tcaaattcat  gctatggtgt  2028
gaaagactac  ctttgacttg  gtattataag  ctggagttat  atatgtattt  gaaacagag   2088 taaatactta  agaggccaaa  tagatgaatg  gaagaatttt  aggaactgtg  agaggggac   2148 aaggtgaagc  tttcctggcc  ctgggaggaa  gctggctgtg  gtagcgtagc  gctctctctc  2208
tctgtctgtg  gcaggagcca  aagagtaggg  tgtaattgag  tgaaggaatc  ctgggtagag  2268
accattctca  ggtggttggg  ccaggctaaa  gactgggagt  tgggtctatc  tatgcctttc  2328
tggctgattt  ttgtagagac  ggggttttgc  catgttaccc  aggctggtct  caaactcctg  2388
ggctcaagcg  atcctcctgg  ctcagcctcc  caaagtgctg  ggattacagg  cgtgaatcac  2448
tgcgcctggc  ttcctcttcc  tcttgagaaa  tattctttc   atacagcaag  tatgggacag  2508
cagtgtccca  ggtaaaggac  ataaatgtta  caagtgtctg  gtcctttctg  agggaggctg  2568
gtgccgctct  gcagggtatt  tgaacctgtg  gaattggagg  aggccatttc  actccctgaa  2628
cccagcctga  caaatcacag  tgagaatgtt  caccttatag  gcttgctgtg  gggctcaggt  2688
tgaaagtgtg  gggagtgaca  ctgcctaggc  atccagctca  gtgtcatcca  gggcctgtgt  2748
ccctcccgaa  cccagggtca  acctgcctgc  cacaggcact  agaaggacga  atctgcctac  2808
tgcccatgaa  cggggccctc  aagcgtcctg  ggatctcctt  ctccctcctg  tcctgtcctt  2868
```

-continued gcccctcagg actgctggaa aataaatcct ttaaaatagt aaaaaaaaaa aaaaa        2923

<210> SEQ ID NO 2
<211> LENGTH: 93
<212> TYPE: PRT
<213> ORGANISM: Homo sapiens - human MDC

<400> SEQUENCE: 2

Met Ala Arg Leu Gln Thr Ala Leu Leu Val Val Leu Val Leu Leu Ala
                -20                 -15                 -10

Val Ala Leu Gln Ala Thr Glu Ala Gly Pro Tyr Gly Ala Asn Met Glu
             -5                  -1   1                   5

Asp Ser Val Cys Cys Arg Asp Tyr Val Arg Tyr Arg Leu Pro Leu Arg
         10                  15                  20

Val Val Lys His Phe Tyr Trp Thr Ser Asp Ser Cys Pro Arg Pro Gly
     25                  30                  35                  40

Val Val Leu Leu Thr Phe Arg Asp Lys Glu Ile Cys Ala Asp Pro Arg
                 45                  50                  55

Val Pro Trp Val Lys Met Ile Leu Asn Lys Leu Ser Gln
             60                  65

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Primer
      JHSP6

<400> SEQUENCE: 3
gacactatag aatagggc                                                     18

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Primer M13

<400> SEQUENCE: 4
gtaaaacgac ggccagt                                                      17

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer T3.1

<400> SEQUENCE: 5
aattaaccct cactaaaggg                                                   20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Primer T7.1

<400> SEQUENCE: 6
gtaatacgac tcactatagg gc                                                22

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Primer
      390-1F

<400> SEQUENCE: 7
tctatctaga ggcccctacg gcgccaacat ggaag                          35

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Primer
      390-2R

<400> SEQUENCE: 8
caccggatcc tcattggctc agcttattga gaa                            33

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Primer
      390-4R

<400> SEQUENCE: 9
aatggatcca cagcacggag gtgaccaag                                 29

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Primer
      390-3R

<400> SEQUENCE: 10
agtcaagctt agggcactct gggatcggca c                              31

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Primer
      390-FX2

<400> SEQUENCE: 11
tatcggatcc tggttccgcg tggcccctac ggcgccaaca tggaa               45

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer GEX5

<400> SEQUENCE: 12
gaaatccagc aagtatatag ca                                        22

<210> SEQ ID NO 13
<211> LENGTH: 36

```
<212> TYPE: DNA
<213> ORGANISM: Artificial Sequence
<220> FEATURE:
<223> OTHER INFORMATION: Description of Artificial Sequence: Primer
      390-Pe1

<400> SEQUENCE: 13
attgccatgg ccggccccta cggcgccaac atggaa                          36

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Primer
      390RcH

<400> SEQUENCE: 14
gaccaagctt gagacataca ggacagagca                                 30

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Primer
      390RcX

<400> SEQUENCE: 15
tggatctaga agttggcaca ggcttctgg                                  29

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer DC03

<400> SEQUENCE: 16
cgaaattaat acgactcact                                            20

<210> SEQ ID NO 17
<211> LENGTH: 67
<212> TYPE: DNA
<213> ORGANISM: Artificial Sequence
<220> FEATURE:
<223> OTHER INFORMATION: Description of Artificial Sequence: Primer
      390mycRX

<400> SEQUENCE: 17
tggatctaga tcaattcaag tcctcctcgc tgatcagctt ctgctcttgg ctcagcttat  60
tgagaat                                                          67

<210> SEQ ID NO 18
<211> LENGTH: 99
<212> TYPE: PRT
<213> ORGANISM: Homo sapiens - Hu MCP-3

<400> SEQUENCE: 18

Met Lys Ala Ser Ala Ala Leu Leu Cys Leu Leu Leu Thr Ala Ala Ala
            -20                 -15                 -10

Phe Ser Pro Gln Gly Leu Ala Gln Pro Val Gly Ile Asn Thr Ser Thr
        -5                   1               5

Thr Cys Cys Tyr Arg Phe Ile Asn Lys Lys Ile Pro Lys Gln Arg Leu
 10                  15                  20                  25
```

-continued

```
Glu Ser Tyr Arg Arg Thr Thr Ser Ser His Cys Pro Arg Glu Ala Val
                30                  35                  40

Ile Phe Lys Thr Lys Leu Asp Lys Glu Ile Cys Ala Asp Pro Thr Gln
             45                  50                  55

Lys Trp Val Gln Asp Phe Met Lys His Leu Asp Lys Lys Thr Gln Thr
             60                  65                  70

Pro Lys Leu
         75

<210> SEQ ID NO 19
<211> LENGTH: 99
<212> TYPE: PRT
<213> ORGANISM: Homo sapiens - Hu MCP-1

<400> SEQUENCE: 19

Met Lys Val Ser Ala Ala Leu Leu Cys Leu Leu Leu Ile Ala Ala Thr
            -20                 -15                 -10

Phe Ile Pro Gln Gly Leu Ala Gln Pro Asp Ala Ile Asn Ala Pro Val
         -5                   1                   5

Thr Cys Cys Tyr Asn Phe Thr Asn Arg Lys Ile Ser Val Gln Arg Leu
 10                  15                  20                  25

Ala Ser Tyr Arg Arg Ile Thr Ser Ser Lys Cys Pro Lys Glu Ala Val
                 30                  35                  40

Ile Phe Lys Thr Ile Val Ala Lys Glu Ile Cys Ala Asp Pro Lys Gln
             45                  50                  55

Lys Trp Val Gln Asp Ser Met Asp His Leu Asp Lys Gln Thr Gln Thr
             60                  65                  70

Pro Lys Thr
         75

<210> SEQ ID NO 20
<211> LENGTH: 76
<212> TYPE: PRT
<213> ORGANISM: Homo sapiens - Hu MCP-2

<400> SEQUENCE: 20

Gln Pro Asp Ser Val Ser Ile Pro Ile Thr Cys Cys Phe Asn Val Ile
 1               5                  10                  15

Asn Arg Lys Ile Pro Ile Gln Arg Leu Glu Ser Tyr Thr Arg Ile Thr
             20                  25                  30

Asn Ile Gln Cys Pro Lys Glu Ala Val Ile Phe Lys Thr Lys Arg Gly
         35                  40                  45

Lys Glu Val Cys Ala Asp Pro Lys Glu Arg Trp Val Arg Asp Ser Met
     50                  55                  60

Lys His Leu Asp Gln Ile Phe Gln Asn Leu Lys Pro
 65                  70                  75

<210> SEQ ID NO 21
<211> LENGTH: 91
<212> TYPE: PRT
<213> ORGANISM: Homo sapiens - RANTES

<400> SEQUENCE: 21

Met Lys Val Ser Ala Ala Ala Leu Ala Val Ile Leu Ile Ala Thr Ala
            -20                 -15                 -10

Leu Cys Ala Pro Ala Ser Ala Ser Pro Tyr Ser Ser Asp Thr Thr Pro
         -5                   1                   5
```

```
Cys Cys Phe Ala Tyr Ile Ala Arg Pro Leu Pro Arg Ala His Ile Lys
 10              15              20              25

Glu Tyr Phe Tyr Thr Ser Gly Lys Cys Ser Asn Pro Ala Val Val Phe
             30              35              40

Val Thr Arg Lys Asn Arg Gln Val Cys Ala Asn Pro Glu Lys Lys Trp
         45              50              55

Val Arg Glu Tyr Ile Asn Ser Leu Glu Met Ser
         60              65

<210> SEQ ID NO 22
<211> LENGTH: 91
<212> TYPE: PRT
<213> ORGANISM: Homo sapiens - MIP-1 beta

<400> SEQUENCE: 22

Met Lys Leu Cys Val Thr Val Leu Ser Leu Leu Met Leu Val Ala Ala
             -20             -15             -10

Phe Cys Ser Pro Ala Leu Ser Ala Pro Met Gly Ser Asp Pro Pro Thr
         -5               1               5

Ala Cys Cys Phe Ser Tyr Thr Arg Glu Ala Ser Ser Asn Phe Val Val
 10              15              20              25

Asp Tyr Tyr Glu Thr Ser Ser Leu Cys Ser Gln Pro Ala Val Val Phe
             30              35              40

Gln Thr Lys Arg Ser Lys Gln Val Cys Ala Asp Pro Ser Glu Ser Trp
         45              50              55

Val Gln Glu Tyr Val Tyr Asp Leu Glu Leu Asn
         60              65

<210> SEQ ID NO 23
<211> LENGTH: 92
<212> TYPE: PRT
<213> ORGANISM: Homo sapiens - MIP-1 alpha

<400> SEQUENCE: 23

Met Gln Val Ser Thr Ala Ala Leu Ala Val Leu Leu Cys Thr Met Ala
             -20             -15             -10

Leu Cys Asn Gln Phe Ser Ala Ser Leu Ala Ala Asp Thr Pro Thr Ala
 -5               1               5                              10

Cys Cys Phe Ser Tyr Thr Ser Arg Gln Ile Pro Gln Asn Phe Ile Ala
             15              20              25

Asp Tyr Phe Glu Thr Ser Ser Gln Cys Ser Lys Pro Gly Val Ile Phe
         30              35              40

Leu Thr Lys Arg Ser Arg Gln Val Cys Ala Asp Pro Ser Glu Glu Trp
         45              50              55

Val Gln Lys Tyr Val Ser Asp Leu Glu Leu Ser Ala
         60              65              70

<210> SEQ ID NO 24
<211> LENGTH: 96
<212> TYPE: PRT
<213> ORGANISM: Homo sapiens - I-309

<400> SEQUENCE: 24

Met Gln Ile Ile Thr Thr Ala Leu Val Cys Leu Leu Leu Ala Gly Met
             -20             -15             -10

Trp Pro Glu Asp Val Asp Ser Lys Ser Met Gln Val Pro Phe Ser Arg
 -5               1               5                              10

Cys Cys Phe Ser Phe Ala Glu Gln Glu Ile Pro Leu Arg Ala Ile Leu
```

```
                   15                  20                  25
Cys Tyr Arg Asn Thr Ser Ser Ile Cys Ser Asn Glu Gly Leu Ile Phe
                30                  35                  40

Lys Leu Lys Arg Gly Lys Glu Ala Cys Ala Leu Asp Thr Val Gly Trp
                45                  50                  55

Val Gln Arg His Arg Lys Met Leu Arg His Cys Pro Ser Lys Arg Lys
    60                  65                  70

<210> SEQ ID NO 25
<211> LENGTH: 93
<212> TYPE: PRT
<213> ORGANISM: Artificial Sequence
<220> FEATURE:
<223> OTHER INFORMATION: Description of Artificial Sequence: Human MDC
      Analog
<221> NAME/KEY: misc_feature
<222> LOCATION: (24)
<223> OTHER INFORMATION: Xaa = arg, gly, ala, val, leu, ile,
      pro, ser, thr, phe, tyr, trp,  aspartate,
      glutamate, asn, gln, cys, or met
<221> NAME/KEY: misc_feature
<222> LOCATION: (27)
<223> OTHER INFORMATION: Xaa = lys, gly,ala, val, leu, ile, pro, ser,
      thr, phe, tyr, trp, aspartate, glutamate, asn, gln, cys, or met
<221> NAME/KEY: misc_feature
<222> LOCATION: (30)
<223> OTHER INFORMATION: Xaa = tyr, ser, lys, arg, his, aspartate,
      glutamate, asn, gln, or cys
<221> NAME/KEY: misc_feature
<222> LOCATION: (50)
<223> OTHER INFORMATION: Xaa = glu, lys, arg, his, gly, or ala
<221> NAME/KEY: misc_feature
<222> LOCATION: (59)
<223> OTHER INFORMATION: Xaa =  trp, ser, lys, arg, his, aspartate,
      glutamate, asn, gln, or cys
<221> NAME/KEY: misc_feature
<222> LOCATION: (60)
<223> OTHER INFORMATION: Xaa = val, ser, lys, arg, his, aspartate,
      glutamate, asn, gln, or cys

<400> SEQUENCE: 25

Met Ala Arg Leu Gln Thr Ala Leu Leu Val Val Leu Val Leu Leu Ala
            -20                 -15                 -10

Val Ala Leu Gln Ala Thr Glu Ala Gly Pro Tyr Gly Ala Asn Met Glu
         -5                   1                   5

Asp Ser Val Cys Cys Arg Asp Tyr Val Arg Tyr Arg Leu Pro Leu Xaa
    10                  15                  20

Val Val Xaa His Phe Xaa Trp Thr Ser Asp Ser Cys Pro Arg Pro Gly
25                  30                  35                  40

Val Val Leu Leu Thr Phe Arg Asp Lys Xaa Ile Cys Ala Asp Pro Arg
                45                  50                  55

Val Pro Xaa Xaa Lys Met Ile Leu Asn Lys Leu Ser Gln
            60                  65

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Primer
      390-7F

<400> SEQUENCE: 26
tattggatcc gttctagctc cctgttctcc                                  30

<210> SEQ ID NO 27
```

```
<211> LENGTH: 31
<212> TYPE: DNA
<213> ORGANISM: Artificial Sequence
<220> FEATURE:
<223> OTHER INFORMATION: Description of Artificial Sequence: Primer
      390-8R

<400> SEQUENCE: 27
ccaagaattc ctgcagccac tttctgggct c                                      31

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Primer ARA1

<400> SEQUENCE: 28
gcgactctct actgtttctc                                                   20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Primer ARA2

<400> SEQUENCE: 29
cacaggaaac agctatgacc                                                   20

<210> SEQ ID NO 30
<211> LENGTH: 70
<212> TYPE: PRT
<213> ORGANISM: Artificial Sequence
<220> FEATURE:
<223> OTHER INFORMATION: Description of Artificial Sequence: Human MDC
      analog

<400> SEQUENCE: 30

Leu Gly Pro Tyr Gly Ala Asn Met Glu Asp Ser Val Cys Cys Arg Asp
1               5                   10                  15

Tyr Val Arg Tyr Arg Leu Pro Leu Arg Val Val Lys His Phe Tyr Trp
                20                  25                  30

Thr Ser Asp Ser Cys Pro Arg Pro Gly Val Val Leu Leu Thr Phe Arg
            35                  40                  45

Asp Lys Glu Ile Cys Ala Asp Pro Arg Val Pro Trp Val Lys Met Ile
    50                  55                  60

Leu Asn Lys Leu Ser Gln
65                  70

<210> SEQ ID NO 31
<211> LENGTH: 69
<212> TYPE: PRT
<213> ORGANISM: Artificial Sequence
<220> FEATURE:
<223> OTHER INFORMATION: Description of Artificial Sequence: Human MDC
      analog

<400> SEQUENCE: 31

Gly Pro Tyr Gly Ala Asn Met Glu Asp Ser Val Cys Cys Arg Asp Tyr
1               5                   10                  15

Val Arg Tyr Arg Leu Pro Leu Arg Val Val Lys His Phe Tyr Trp Thr
                20                  25                  30

Ser Asp Ser Cys Pro Arg Pro Gly Val Val Leu Leu Thr Phe Arg Asp
```

-continued

```
                35                  40                  45
Lys Glu Ile Cys Ala Asp Pro Arg Val Pro Tyr Leu Lys Met Ile Leu
 50                  55                  60

Asn Lys Leu Ser Gln
 65

<210> SEQ ID NO 32
<211> LENGTH: 69
<212> TYPE: PRT
<213> ORGANISM: Artificial Sequence
<220> FEATURE:
<223> OTHER INFORMATION: Description of Artificial Sequence: Human MDC
      analog

<400> SEQUENCE: 32

Gly Pro Tyr Gly Ala Asn Met Glu Asp Ser Val Cys Cys Arg Asp Tyr
  1               5                  10                  15

Val Arg Tyr Arg Leu Pro Leu Arg Val Val Lys Glu Tyr Phe Tyr Thr
                 20                  25                  30

Ser Asp Ser Cys Pro Arg Pro Gly Val Val Leu Leu Thr Phe Arg Asp
             35                  40                  45

Lys Glu Ile Cys Ala Asp Pro Arg Val Pro Trp Val Lys Met Ile Leu
 50                  55                  60

Asn Lys Leu Ser Gln
 65

<210> SEQ ID NO 33
<211> LENGTH: 1677
<212> TYPE: DNA
<213> ORGANISM: Homo sapiens - human CCR4 cDNA
<220> FEATURE:
<221> NAME/KEY: CDS
<222> LOCATION: (183)..(1262)

<400> SEQUENCE: 33
cgggggtttt gatcttcttc cccttctttt cttcccctto ttctttcctt cctccctccc      60
tctctcattt cccttctcct tctccctcag tctccacatt caacattgac aagtccattc     120
agaaaagcaa gctgcttctg gttgggccca gacctgcctt gaggagcctg tagagttaaa     180 aa atg aac ccc acg gat ata gca gat acc acc ctc gat gaa agc ata        227
   Met Asn Pro Thr Asp Ile Ala Asp Thr Thr Leu Asp Glu Ser Ile
    1               5                  10                  15 tac agc aat tac tat ctg tat gaa agt atc ccc aag cct tgc acc aaa       275
Tyr Ser Asn Tyr Tyr Leu Tyr Glu Ser Ile Pro Lys Pro Cys Thr Lys
                 20                  25                  30 gaa ggc atc aag gca ttt ggg gag ctc ttc ctg ccc cca ctg tat tcc       323
Glu Gly Ile Lys Ala Phe Gly Glu Leu Phe Leu Pro Pro Leu Tyr Ser
             35                  40                  45 ttg gtt ttt gta ttt ggt ctg ctt gga aat tct gtg gtg gtt ctg gtc       371
Leu Val Phe Val Phe Gly Leu Leu Gly Asn Ser Val Val Val Leu Val
 50                  55                  60 ctg ttc aaa tac aag cgg ctc agg tcc atg act gat gtg tac ctg ctc       419
Leu Phe Lys Tyr Lys Arg Leu Arg Ser Met Thr Asp Val Tyr Leu Leu
 65                  70                  75 aac ctt gcc atc tcg gat ctg ctc ttc gtg ttt tcc ctc cct ttt tgg       467
Asn Leu Ala Ile Ser Asp Leu Leu Phe Val Phe Ser Leu Pro Phe Trp
 80                  85                  90                  95 ggc tac tat gca gca gac cag tgg gtt ttt ggg cta ggt ctg tgc aag       515
Gly Tyr Tyr Ala Ala Asp Gln Trp Val Phe Gly Leu Gly Leu Cys Lys
                100                 105                 110
```

```
atg att tcc tgg atg tac ttg gtg ggc ttt tac agt ggc ata ttc ttt        563
Met Ile Ser Trp Met Tyr Leu Val Gly Phe Tyr Ser Gly Ile Phe Phe
        115                 120                 125 gtc atg ctc atg agc att gat aga tac ctg gcg ata gtg cac gcg gtg        611
Val Met Leu Met Ser Ile Asp Arg Tyr Leu Ala Ile Val His Ala Val
        130                 135                 140 ttt tcc ttg agg gca agg acc ttg act tat ggg gtc atc acc agt ttg        659
Phe Ser Leu Arg Ala Arg Thr Leu Thr Tyr Gly Val Ile Thr Ser Leu
145                 150                 155 gct aca tgg tca gtg gct gtg ttc gcc tcc ctt cct ggc ttt ctg ttc        707
Ala Thr Trp Ser Val Ala Val Phe Ala Ser Leu Pro Gly Phe Leu Phe
160                 165                 170                 175 agc act tgt tat act gag cgc aac cat acc tac tgc aaa acc aag tac        755
Ser Thr Cys Tyr Thr Glu Arg Asn His Thr Tyr Cys Lys Thr Lys Tyr
            180                 185                 190 tct ctc aac tcc acg acg tgg aag gtt ctc agc tcc ctg gaa atc aac        803
Ser Leu Asn Ser Thr Thr Trp Lys Val Leu Ser Ser Leu Glu Ile Asn
        195                 200                 205 att ctc gga ttg gtg atc ccc tta ggg atc atg ctg ttt tgc tac tcc        851
Ile Leu Gly Leu Val Ile Pro Leu Gly Ile Met Leu Phe Cys Tyr Ser
    210                 215                 220 atg atc atc agg acc ttg cag cat tgt aaa aat gag aag aag aac aag        899
Met Ile Ile Arg Thr Leu Gln His Cys Lys Asn Glu Lys Lys Asn Lys
225                 230                 235 gcg gtg aag atg atc ttt gcc gtg gtg gtc ctc ttc ctt ggg ttc tgg        947
Ala Val Lys Met Ile Phe Ala Val Val Val Leu Phe Leu Gly Phe Trp
240                 245                 250                 255 aca cct tac aac ata gtg ctc ttc cta gag acc ctg gtg gag cta gaa        995
Thr Pro Tyr Asn Ile Val Leu Phe Leu Glu Thr Leu Val Glu Leu Glu
                260                 265                 270 gtc ctt cag gac tgc acc ttt gaa aga tac ttg gac tat gcc atc cag       1043
Val Leu Gln Asp Cys Thr Phe Glu Arg Tyr Leu Asp Tyr Ala Ile Gln
            275                 280                 285 gcc aca gaa act ctg gct ttt gtt cac tgc tgc ctt aat ccc atc atc       1091
Ala Thr Glu Thr Leu Ala Phe Val His Cys Cys Leu Asn Pro Ile Ile
        290                 295                 300 tac ttt ttt ctg ggg gag aaa ttt cgc aag tac atc cta cag ctc ttc       1139
Tyr Phe Phe Leu Gly Glu Lys Phe Arg Lys Tyr Ile Leu Gln Leu Phe
305                 310                 315 aaa acc tgc agg ggc ctt ttt gtg ctc tgc caa tac tgt ggg ctc ctc       1187
Lys Thr Cys Arg Gly Leu Phe Val Leu Cys Gln Tyr Cys Gly Leu Leu
320                 325                 330                 335 caa att tac tct gct gac acc ccc agc tca tct tac acg cag tcc acc       1235
Gln Ile Tyr Ser Ala Asp Thr Pro Ser Ser Ser Tyr Thr Gln Ser Thr
                340                 345                 350 atg gat cat gat ctt cat gat gct ctg taggaaaaat gaatggtga              1282
Met Asp His Asp Leu His Asp Ala Leu
            355                 360 aatgcagagt caatgaactt ttccacattc agagcttact ttaaaattgg tattttagg      1342 taagagatcc ctgagccagt gtcaggagga aggcttacac ccacagtgga agacagctt      1402 ctcatcctgc aggcagcttt ttctctccca ctagacaagt ccagcctggc aagggttcac     1462
ctgggctgag gcatccttcc tcacaccagg cttgcctgca ggcatgagtc agtctgatga     1522
gaactctgag cagtgcttga atgaagttgt aggtaatatt gcaaggcaaa gactattccc     1582
ttctaacctg aactgatggg tttctccaga gggaattgca gagtactggc tgatggagta     1642
aatcgctacc ttttgctgtg gcaaatgggc ccccg                                1677
```

```
<210> SEQ ID NO 34
<211> LENGTH: 360
<212> TYPE: PRT
<213> ORGANISM: Homo sapiens - human CCR4

<400> SEQUENCE: 34

Met Asn Pro Thr Asp Ile Ala Asp Thr Thr Leu Asp Glu Ser Ile Tyr
  1               5                  10                  15

Ser Asn Tyr Tyr Leu Tyr Glu Ser Ile Pro Lys Pro Cys Thr Lys Glu
                 20                  25                  30

Gly Ile Lys Ala Phe Gly Glu Leu Phe Leu Pro Pro Leu Tyr Ser Leu
             35                  40                  45

Val Phe Val Phe Gly Leu Leu Gly Asn Ser Val Val Val Leu Val Leu
         50                  55                  60

Phe Lys Tyr Lys Arg Leu Arg Ser Met Thr Asp Val Tyr Leu Leu Asn
 65                  70                  75                  80

Leu Ala Ile Ser Asp Leu Leu Phe Val Phe Ser Leu Pro Phe Trp Gly
                 85                  90                  95

Tyr Tyr Ala Ala Asp Gln Trp Val Phe Gly Leu Gly Leu Cys Lys Met
            100                 105                 110

Ile Ser Trp Met Tyr Leu Val Gly Phe Tyr Ser Gly Ile Phe Phe Val
            115                 120                 125

Met Leu Met Ser Ile Asp Arg Tyr Leu Ala Ile Val His Ala Val Phe
        130                 135                 140

Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
            180                 185                 190

Leu Asn Ser Thr Thr Trp Lys Val Leu Ser Ser Leu Glu Ile Asn Ile
        195                 200                 205

Leu Gly Leu Val Ile Pro Leu Gly Ile Met Leu Phe Cys Tyr Ser Met
    210                 215                 220

Ile Ile Arg Thr Leu Gln His Cys Lys Asn Glu Lys Lys Asn Lys Ala
225                 230                 235                 240

Val Lys Met Ile Phe Ala Val Val Val Leu Phe Leu Gly Phe Trp Thr
                245                 250                 255

Pro Tyr Asn Ile Val Leu Phe Leu Glu Thr Leu Val Glu Leu Glu Val
            260                 265                 270

Leu Gln Asp Cys Thr Phe Glu Arg Tyr Leu Asp Tyr Ala Ile Gln Ala
        275                 280                 285

Thr Glu Thr Leu Ala Phe Val His Cys Cys Leu Asn Pro Ile Ile Tyr
    290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Ser Tyr Thr Gln Ser Thr Met
            340                 345                 350

Asp His Asp Leu His Asp Ala Leu
        355                 360

<210> SEQ ID NO 35
<211> LENGTH: 1784
```

<212> TYPE: DNA
<213> ORGANISM: murine MDC cDNA
<220> FEATURE:
<221> NAME/KEY: CDS
<222> LOCATION: (1)..(276)
<221> NAME/KEY: mat_peptide
<222> LOCATION: (73)..(276)

<400> SEQUENCE: 35

```
atg tct aat ctg cgt gtc cca ctc ctg gtg gct ctc gtc ctt ctt gct      48
Met Ser Asn Leu Arg Val Pro Leu Leu Val Ala Leu Val Leu Leu Ala
            -20                 -15                 -10 gtg gca att cag acc tct gat gca ggt ccc tat ggt gcc aat gtg gaa      96
Val Ala Ile Gln Thr Ser Asp Ala Gly Pro Tyr Gly Ala Asn Val Glu
         -5                   1                   5 gac agt atc tgc tgc cag gac tac atc cgt cac cct ctg cca tca cgt     144
Asp Ser Ile Cys Cys Gln Asp Tyr Ile Arg His Pro Leu Pro Ser Arg
         10                  15                  20 tta gtg aag gag ttc ttc tgg acc tca aaa tcc tgc cgc aag cct ggc     192
Leu Val Lys Glu Phe Phe Trp Thr Ser Lys Ser Cys Arg Lys Pro Gly
 25                  30                  35                  40 gtt gtt ttg ata acc gtc aag aac cga gat atc tgt gcc gat ccc agg     240
Val Val Leu Ile Thr Val Lys Asn Arg Asp Ile Cys Ala Asp Pro Arg
                 45                  50                  55 cag gtc tgg gtg aag aag cta ctc cat aaa ctg tcc tagggaggag          286
Gln Val Trp Val Lys Lys Leu Leu His Lys Leu Ser
             60                  65 gacctgatga ccatgggtct ggtgtggtcc agggaggctc agcaagccct attcttctgc   346
cattccagca agagccttgc caacgacgcc acctttactc acctccatcc cctgggctgt   406
cactctgtca ggctctggtc cctctacctc ccctctatcc cttccagctt atccccttc    466
aatgtggcag ctgggaaaca cattcaggcc agccttaccc aatgcctact ccccactgct   526
ttagatgaga ccagcgtcct tgttttgatg ccctgatcct atgatgcctt ccccatcccc   586
agccttggcc cccttctctt cttgcatgta gggaaggccc ataggtttca aatatgtgct   646
acctacttcc ctttctgggg ggttctaata cccagcatgt ttttcctgct gcaggcacct   706
atccagtgcc acacacctcc caagtttcta tcagtcccag tgggcatcca ccaagcccca   766
aacttcagac ttccttggcc tccacctact ctcagtagaa ttctgggagt ttcaggctgg   826
tccaccaggc cccccagggt taggccaagg tccccaccag agctcctcct gtttcttggt   886
ctgcagcacg gggcagggag caaggagcag gctcagaatc agatttctta aaggagctgc   946
agactccatc agtaaaagga atctttctcc catccctgaa tataaggcag ttttctgtca  1006
acacagagac tcaggttgtt agaaatggcc acatagatca actgtgaaac cctaaattta  1066
ccaagaatca acttccaccc ctcttcaacc acatgctagg gtcttttact ttctctgccc  1126
cacacctttg actccttgcc tgtgtagctg atagtcgaag ttatgctatg gtgtcagtga  1186
ctgccacagt ttgtttggta ttataagcta tagttatatt tatataggaa agaggataaa  1246
tatatgtggg ccaaatagac gaactggaga gttttaggat ctgggggcag gaagggccat  1306
acaaagtgat acctcagaaa atagatggtt gtgggagctg ctgccagtgg cagagttaac  1366
ttaaagaact taattgaaat tattcttgag tggctgaggc caagacaaga atatagaacc  1426
cattcttgct tccctggaga caacagtggt cccaggggaa ggaataaacc ttcttgctcc  1486
tctggaggga gcatggcctg rcttagccga gtgactggac tgtgtgagat tggggcatc   1546
gcttttccty tctgagcctc agctgacagc atatgggacc acaaagggct tgatccaaac  1606
cacagggatt gacagtgcca gccacagctg tgtccagggc tcgtgttctg ccagaaggag  1666
```

```
cacctggacg accagggcca ccactagtgc tactttgctc actgcccatg catgtcctga        1726
aggtccctcc ccctcctctc ctacttctgg gaaaataaat gctcgccaat aatacctg          1784
```

<210> SEQ ID NO 36
<211> LENGTH: 92
<212> TYPE: PRT
<213> ORGANISM: murine MDC

<400> SEQUENCE: 36

```
Met Ser Asn Leu Arg Val Pro Leu Leu Val Ala Leu Val Leu Ala
                -20              -15             -10

Val Ala Ile Gln Thr Ser Asp Ala Gly Pro Tyr Gly Ala Asn Val Glu
            -5               1               5

Asp Ser Ile Cys Cys Gln Asp Tyr Ile Arg His Pro Leu Pro Ser Arg
            10              15              20

Leu Val Lys Glu Phe Phe Trp Thr Ser Lys Ser Cys Arg Lys Pro Gly
25              30              35              40

Val Val Leu Ile Thr Val Lys Asn Arg Asp Ile Cys Ala Asp Pro Arg
                45              50              55

Gln Val Trp Val Lys Lys Leu Leu His Lys Leu Ser
            60              65
```

<210> SEQ ID NO 37
<211> LENGTH: 958
<212> TYPE: DNA
<213> ORGANISM: rat MDC cDNA
<220> FEATURE:
<221> NAME/KEY: CDS
<222> LOCATION: (1)..(243)
<221> NAME/KEY: mat_peptide
<222> LOCATION: (40)..(243)
<221> NAME/KEY: misc_feature
<222> LOCATION: (206)
<223> OTHER INFORMATION: n = A or G or T or C
<221> NAME/KEY: misc_feature
<222> LOCATION: (785)
<223> OTHER INFORMATION: n = A or G or T or C
<221> NAME/KEY: misc_feature
<222> LOCATION: (827)
<223> OTHER INFORMATION: n = A or G or T or C
<221> NAME/KEY: misc_feature
<222> LOCATION: (836)
<223> OTHER INFORMATION: n = A or G or T or C
<221> NAME/KEY: misc_feature
<222> LOCATION: (861)
<223> OTHER INFORMATION: n = A or G or T or C
<221> NAME/KEY: misc_feature
<222> LOCATION: (864)
<223> OTHER INFORMATION: n = A or G or T or C
<221> NAME/KEY: misc_feature
<222> LOCATION: (871)
<223> OTHER INFORMATION: n = A or G or T or C
<221> NAME/KEY: misc_feature
<222> LOCATION: (878)
<223> OTHER INFORMATION: n = A or G or T or C
<221> NAME/KEY: misc_feature
<222> LOCATION: (206)
<223> OTHER INFORMATION: n = A or G or T or C
<221> NAME/KEY: misc_feature
<222> LOCATION: (882)
<223> OTHER INFORMATION: n = A or G or T or C
<221> NAME/KEY: misc_feature
<222> LOCATION: (900)
<223> OTHER INFORMATION: n = A or G or T or C
<221> NAME/KEY: misc_feature
<222> LOCATION: (902)
<223> OTHER INFORMATION: n = A or G or T or C
<221> NAME/KEY: misc_feature
<222> LOCATION: (206)

```
<223> OTHER INFORMATION: n = A or G or T or C
<221> NAME/KEY: misc_feature
<222> LOCATION: (907)
<223> OTHER INFORMATION: n = A or G or T or C
<221> NAME/KEY: misc_feature
<222> LOCATION: (206)
<223> OTHER INFORMATION: n = A or G or T or C
<221> NAME/KEY: misc_feature
<222> LOCATION: (916)
<223> OTHER INFORMATION: n = A or G or T or C
<221> NAME/KEY: misc_feature
<222> LOCATION: (921)
<223> OTHER INFORMATION: n = A or G or T or C
<221> NAME/KEY: misc_feature
<222> LOCATION: (951)
<223> OTHER INFORMATION: n = A or G or T or C
<221> NAME/KEY: misc_feature
<222> LOCATION: (958)
<223> OTHER INFORMATION: n = A or G or T or C

<400> SEQUENCE: 37
```

| | | | | | | | | | | | | | | | | |
|---|---|---|---|---|---|---|---|---|---|---|---|---|---|---|---|---|
| ctc | gtc | ctt | ctt | gct | gtg | gca | ctt | cag | acc | tcc | gat | gca | ggt | ccc | tat | 48 |
| Leu | Val | Leu | Leu | Ala | Val | Ala | Leu | Gln | Thr | Ser | Asp | Ala | Gly | Pro | Tyr | |
| | | -10 | | | | | -5 | | | | | 1 | | | | |
| ggt | gcc | aat | gtg | gaa | gac | agt | atc | tgc | tgc | cag | gac | tac | atc | cgt | cac | 96 |
| Gly | Ala | Asn | Val | Glu | Asp | Ser | Ile | Cys | Cys | Gln | Asp | Tyr | Ile | Arg | His | |
| | 5 | | | | | 10 | | | | | 15 | | | | | |
| cct | ctg | cca | cca | cgt | ttc | gtg | aag | gag | ttc | tac | tgg | acc | tca | aag | tcc | 144 |
| Pro | Leu | Pro | Pro | Arg | Phe | Val | Lys | Glu | Phe | Tyr | Trp | Thr | Ser | Lys | Ser | |
| 20 | | | | | 25 | | | | | 30 | | | | | 35 | |
| tgc | cgc | aag | cct | ggc | gtc | gtt | ttg | ata | acc | atc | aag | aac | cga | gat | atc | 192 |
| Cys | Arg | Lys | Pro | Gly | Val | Val | Leu | Ile | Thr | Ile | Lys | Asn | Arg | Asp | Ile | |
| | | | | 40 | | | | | 45 | | | | | 50 | | |
| tgt | gct | gac | ccc | ang | atg | ctc | tgg | gtg | aag | aag | ata | ctc | cac | aag | ttg | 240 |
| Cys | Ala | Asp | Pro | Xaa | Met | Leu | Trp | Val | Lys | Lys | Ile | Leu | His | Lys | Leu | |
| | | 55 | | | | | 60 | | | | | 65 | | | | |

```
gcc tagggagaag ggcctgatga ccacgggtct ggtgtctcca caaggctcag      293
Ala caaaccctat ccttctgcca tccagcaaga gccttgccaa caactccacc tttgctcacc   353
tccatcccct gggttgtcac tctgtgaagc ctcgggtccc tgtacttcct gtccgtcccc   413
tccagctcat tctcttccaa cgtggcagcc gggaagcact tctggctagc cttacccaat   473
actactcccc actgctttaa atgagaccag ggtccttgtt ttggtgcctt tggatccta    533 gatgccttcc cagtctccag ccttggcccc cttctcttct tacatgtagg gaacaccaat   593
atctttcaag tatgtgctac ccaattcctc ttcctcggag gctgctggga cccggaatat   653
tatcccctgc tgcaggcctc tccaagcacc actcacctcc caggctttcc atccgtccca   713
gtcccaagcc ccatgcttca gaacttccct tggccccccc ctacactcca caaattctgg   773
ggaagtctca cnaactgggt cccctcaggc ccccacggga aggaaggtcc cccnccaaca   833
acntcctcct gttttcccg gtctcccncc nccgggantt gggcnccna atccccaatt    893 tctgaanang aacngcccat tcntccctt aaaattaacc tttccccccc tccctgangt    953 taggn                                                              958

<210> SEQ ID NO 38
<211> LENGTH: 81
<212> TYPE: PRT
<213> ORGANISM: rat
<220> FEATURE:
<221> NAME/KEY: misc_feature
<222> LOCATION: (56)
<223> OTHER INFORMATION: Xaa = any or unknown amino acid
```

```
<400> SEQUENCE: 38

Leu Val Leu Leu Ala Val Ala Leu Gln Thr Ser Asp Ala Gly Pro Tyr
            -10                 -5                  1
Gly Ala Asn Val Glu Asp Ser Ile Cys Cys Gln Asp Tyr Ile Arg His
      5                  10                 15
Pro Leu Pro Pro Arg Phe Val Lys Glu Phe Tyr Trp Thr Ser Lys Ser
 20                  25                  30                  35
Cys Arg Lys Pro Gly Val Val Leu Ile Thr Ile Lys Asn Arg Asp Ile
                 40                  45                  50
Cys Ala Asp Pro Xaa Met Leu Trp Val Lys Lys Ile Leu His Lys Leu
             55                  60                  65
Ala

<210> SEQ ID NO 39
<211> LENGTH: 506
<212> TYPE: DNA
<213> ORGANISM: Artificial Sequence
<220> FEATURE:
<223> OTHER INFORMATION: Description of Artificial Sequence: S.
      cerevisiae alpha factor pre-pro/human MDC cDNA chimeric construct
<221> NAME/KEY: CDS
<222> LOCATION: (15)..(476)
<221> NAME/KEY: mat_peptide
<222> LOCATION: (270)..(476)

<400> SEQUENCE: 39
atctcgagct cacg atg aga ttt cct tca att ttt act gca gtt tta ttc      50
              Met Arg Phe Pro Ser Ile Phe Thr Ala Val Leu Phe
              -85                 -80                 -75 gca gca tcc tcc gca tta gct gct cca gtc aac act aca aca gaa gat      98
Ala Ala Ser Ser Ala Leu Ala Ala Pro Val Asn Thr Thr Thr Glu Asp
            -70                 -65                 -60 gaa acg gca caa att ccg gct gaa gct gtc atc ggt tac tta gat tta     146
Glu Thr Ala Gln Ile Pro Ala Glu Ala Val Ile Gly Tyr Leu Asp Leu
        -55                 -50                 -45 gaa ggg gat ttc gat gtt gct gtt ttg cca ttt tcc aac agc aca aat     194
Glu Gly Asp Phe Asp Val Ala Val Leu Pro Phe Ser Asn Ser Thr Asn
    -40                 -35                 -30 aac ggg tta ttg ttt ata aat act act att gcc agc att gct gct aaa     242
Asn Gly Leu Leu Phe Ile Asn Thr Thr Ile Ala Ser Ile Ala Ala Lys
-25                 -20                 -15                 -10 gaa gaa ggg gta cct ttg gat aaa aga ggc ccc tac ggc gcc aac atg     290
Glu Glu Gly Val Pro Leu Asp Lys Arg Gly Pro Tyr Gly Ala Asn Met
                 -5                  1                   5 gaa gac agc gtc tgc tgc cgt gat tac gtc cgt tac cgt ctg ccc ctg     338
Glu Asp Ser Val Cys Cys Arg Asp Tyr Val Arg Tyr Arg Leu Pro Leu
             10                  15                  20 cgc gtg gtg aaa cac ttc tac tgg acc tca gac tcc tgc ccg agg cct     386
Arg Val Val Lys His Phe Tyr Trp Thr Ser Asp Ser Cys Pro Arg Pro
 25                  30                  35 ggc gtg gtg ttg cta acc ttc agg gat aag gag atc tgt gcc gat ccc     434
Gly Val Val Leu Leu Thr Phe Arg Asp Lys Glu Ile Cys Ala Asp Pro
 40                  45                  50                  55 aga gtg ccc tgg gtg aag atg att ctc aat aag ctg agc caa              476
Arg Val Pro Trp Val Lys Met Ile Leu Asn Lys Leu Ser Gln
                 60                  65 tgaaggcctt ctagagcggc cgcatcgata                                     506

<210> SEQ ID NO 40
<211> LENGTH: 154
```

-continued

```
<212> TYPE: PRT
<213> ORGANISM: cDNA

<400> SEQUENCE: 40

Met Arg Phe Pro Ser Ile Phe Thr Ala Val Leu Phe Ala Ala Ser Ser
-85                 -80                 -75                 -70

Ala Leu Ala Ala Pro Val Asn Thr Thr Thr Glu Asp Glu Thr Ala Gln
            -65                 -60                 -55

Ile Pro Ala Glu Ala Val Ile Gly Tyr Leu Asp Leu Glu Gly Asp Phe
            -50                 -45                 -40

Asp Val Ala Val Leu Pro Phe Ser Asn Ser Thr Asn Asn Gly Leu Leu
        -35                 -30                 -25

Phe Ile Asn Thr Thr Ile Ala Ser Ile Ala Lys Glu Glu Gly Val
    -20                 -15                 -10

Pro Leu Asp Lys Arg Gly Pro Tyr Gly Ala Asn Met Glu Asp Ser Val
 -5              1               5              10

Cys Cys Arg Asp Tyr Val Arg Tyr Arg Leu Pro Leu Arg Val Val Lys
            15                  20                  25

His Phe Tyr Trp Thr Ser Asp Ser Cys Pro Arg Pro Gly Val Val Leu
            30                  35                  40

Leu Thr Phe Arg Asp Lys Glu Ile Cys Ala Asp Pro Arg Val Pro Trp
        45                  50                  55

Val Lys Met Ile Leu Asn Lys Leu Ser Gln
 60                  65

<210> SEQ ID NO 41
<211> LENGTH: 93
<212> TYPE: PRT
<213> ORGANISM: Artificial Sequence
<220> FEATURE:
<223> OTHER INFORMATION: Description of Artificial Sequence: Human MDC
      Analog
<221> NAME/KEY: misc_feature
<222> LOCATION: (2)
<223> OTHER INFORMATION: Xaa = not proline

<400> SEQUENCE: 41

Met Ala Arg Leu Gln Thr Ala Leu Leu Val Val Leu Val Leu Leu Ala
                -20                 -15                 -10

Val Ala Leu Gln Ala Thr Glu Ala Gly Xaa Tyr Gly Ala Asn Met Glu
             -5                  1                   5

Asp Ser Val Cys Cys Arg Asp Tyr Val Arg Tyr Arg Leu Pro Leu Arg
        10                  15                  20

Val Val Lys His Phe Tyr Trp Thr Ser Asp Ser Cys Pro Arg Pro Gly
 25                  30                  35                  40

Val Val Leu Leu Thr Phe Arg Asp Lys Glu Ile Cys Ala Asp Pro Arg
            45                  50                  55

Val Pro Trp Val Lys Met Ile Leu Asn Lys Leu Ser Gln
             60                  65

<210> SEQ ID NO 42
<211> LENGTH: 538
<212> TYPE: DNA
<213> ORGANISM: Homo sapiens
<220> FEATURE:
<221> NAME/KEY: CDS
<222> LOCATION: (53)..(334)
<221> NAME/KEY: mat_peptide
<222> LOCATION: (122)..(334)

<400> SEQUENCE: 42
```

```
cctgagcag   agggacctgc   acacagagac   tccctcctgg   gctcctggca   cc atg gcc                        58
                                                                  Met Ala cca ctg aag atg ctg gcc ctg gtc acc ctc ctc ctg ggg gct tct ctg                                  106
Pro Leu Lys Met Leu Ala Leu Val Thr Leu Leu Leu Gly Ala Ser Leu
    -20             -15                 -10 cag cac atc cac gca gct cga ggg acc aat gtg ggc cgg gag tgc tgc                                  154
Gln His Ile His Ala Ala Arg Gly Thr Asn Val Gly Arg Glu Cys Cys
-5                  1               5                       10 ctg gag tac ttc aag gga gcc att ccc ctt aga aag ctg aag acg tgg                                  202
Leu Glu Tyr Phe Lys Gly Ala Ile Pro Leu Arg Lys Leu Lys Thr Trp
            15              20              25 tac cag aca tct gag gac tgc tcc agg gat gcc atc gtt ttt gta act                                  250
Tyr Gln Thr Ser Glu Asp Cys Ser Arg Asp Ala Ile Val Phe Val Thr
            30              35              40 gtg cag ggc agg gcc atc tgt tcg gac ccc aac aac aag aga gtg aag                                  298
Val Gln Gly Arg Ala Ile Cys Ser Asp Pro Asn Asn Lys Arg Val Lys
            45              50              55 aat gca gtt aaa tac ctg caa agc ctt gag agg tct tgaagcctcc                                       344
Asn Ala Val Lys Tyr Leu Gln Ser Leu Glu Arg Ser
60              65              70 tcaccccaga ctcctgactg tctcccggga ctacctggga cctccaccgt tggtgttcac                                 404
cgcccccacc ctgagcgcct gggtccaggg gaggccttcc agggacgaag aagagccaca                                 464
gtgagggaga tcccatcccc ttgtctgaac tggagccatg ggcacaaagg gcccagatta                                 524
aagtctttat cctc                                                                                  538

<210> SEQ ID NO 43
<211> LENGTH: 94
<212> TYPE: PRT
<213> ORGANISM: Homo sapiens

<400> SEQUENCE: 43

Met Ala Pro Leu Lys Met Leu Ala Leu Val Thr Leu Leu Leu Gly Ala
            -20                 -15                 -10

Ser Leu Gln His Ile His Ala Ala Arg Gly Thr Asn Val Gly Arg Glu
        -5                  1               5

Cys Cys Leu Glu Tyr Phe Lys Gly Ala Ile Pro Leu Arg Lys Leu Lys
10              15              20              25

Thr Trp Tyr Gln Thr Ser Glu Asp Cys Ser Arg Asp Ala Ile Val Phe
                30              35              40

Val Thr Val Gln Gly Arg Ala Ile Cys Ser Asp Pro Asn Asn Lys Arg
            45              50              55

Val Lys Asn Ala Val Lys Tyr Leu Gln Ser Leu Glu Arg Ser
        60              65              70

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 44
atgggaccat atggagcaaa tatggaagat agt                                                              33

<210> SEQ ID NO 45
<211> LENGTH: 335
<212> TYPE: DNA
<213> ORGANISM: Macaque MDC
```

```
<220> FEATURE:
<221> NAME/KEY: CDS
<222> LOCATION: (19)..(297)

<400> SEQUENCE: 45
agacatacag gacagagc atg gct cgc cta cag act gtg ttc ctg ggt gtc         51
                    Met Ala Arg Leu Gln Thr Val Phe Leu Gly Val
                        -20                         -15 ctc atc ctc ctt gct gtg gcg ctt caa gca act gag gca ggc ccc tat         99
Leu Ile Leu Leu Ala Val Ala Leu Gln Ala Thr Glu Ala Gly Pro Tyr
            -10                 -5                  1 ggc gcc aac atg gaa gac agc gtc tgc tgc cgt gat tac gtc cgt tac        147
Gly Ala Asn Met Glu Asp Ser Val Cys Cys Arg Asp Tyr Val Arg Tyr
    5                   10                  15 cgt atg ccc ctg cgt gtg gtg aaa cac ttc tac tgg acc tca gac tcc        195
Arg Met Pro Leu Arg Val Val Lys His Phe Tyr Trp Thr Ser Asp Ser
20                  25                  30                  35 tgc ccg agg cct ggc gtg gtg ttg cta acc tcc agg gat aag gag atc        243
Cys Pro Arg Pro Gly Val Val Leu Leu Thr Ser Arg Asp Lys Glu Ile
                40                  45                  50 tgt gcc gat ccc aga gtg ccc tgg gtg aag atg att ctc aat aag ctg        291
Cys Ala Asp Pro Arg Val Pro Trp Val Lys Met Ile Leu Asn Lys Leu
                55                  60                  65 agc caa tgaagagcct actatgatga ccgtggccta agcaagcc                      335
Ser Gln <210> SEQ ID NO 46
<211> LENGTH: 93
<212> TYPE: PRT
<213> ORGANISM: Macaque MDC

<400> SEQUENCE: 46

Met Ala Arg Leu Gln Thr Val Phe Leu Gly Val Leu Ile Leu Leu Ala
1               5                   10                  15

Val Ala Leu Gln Ala Thr Glu Ala Gly Pro Tyr Gly Ala Asn Met Glu
            20                  25                  30

Asp Ser Val Cys Cys Arg Asp Tyr Val Arg Tyr Arg Met Pro Leu Arg
        35                  40                  45

Val Val Lys His Phe Tyr Trp Thr Ser Asp Ser Cys Pro Arg Pro Gly
    50                  55                  60

Val Val Leu Leu Thr Ser Arg Asp Lys Glu Ile Cys Ala Asp Pro Arg
65                  70                  75                  80

Val Pro Trp Val Lys Met Ile Leu Asn Lys Leu Ser Gln
                85                  90
```